United States Patent
Beninati et al.

(10) Patent No.: US 8,246,964 B2
(45) Date of Patent: Aug. 21, 2012

(54) **ANTIGENIC PROTEIN FRAGMENTS OF *STREPTOCOCCUS PNEUMONIAE***

(75) Inventors: Concetta Beninati, Messina (IT); Franco Felici, Messina (IT); Marco Oggioni, Siena (IT); Gianni Pozzi, Siena (IT); Susanna Ricci, Siena (IT)

(73) Assignees: Universita' Degli Studi di Siena, Siena (IT); Concetta Beninati, Messina (IT); Franco Felici, Messina (IT)

( * ) Notice: Subject to any disclaimer, the term of this patent is extended or adjusted under 35 U.S.C. 154(b) by 0 days.

(21) Appl. No.: 12/933,214

(22) PCT Filed: Mar. 17, 2009

(86) PCT No.: PCT/EP2009/053121
§ 371 (c)(1),
(2), (4) Date: Nov. 8, 2010

(87) PCT Pub. No.: WO2009/115509
PCT Pub. Date: Sep. 24, 2009

(65) Prior Publication Data
US 2011/0076301 A1  Mar. 31, 2011

(30) Foreign Application Priority Data

Mar. 19, 2008 (EP) .................................. 08425177

(51) Int. Cl.
*A61K 39/09* (2006.01)
*C12P 21/06* (2006.01)
(52) U.S. Cl. .................. 424/244.1; 424/190.1; 435/810; 435/975; 435/69.1; 435/69.3
(58) Field of Classification Search .................. None
See application file for complete search history.

(56) References Cited

U.S. PATENT DOCUMENTS

| 7,122,368 | B1 | 10/2006 | Doucette-Stamm et al. |
| 7,129,339 | B1 * | 10/2006 | Doucette-Stamm et al. ... 536/23.7 |
| 7,424,370 | B2 * | 9/2008 | Sachdeva et al. ............... 702/19 |
| 2005/0020813 | A1 | 1/2005 | Masignani et al. |
| 2006/0263846 | A1 | 11/2006 | Meinke et al. |

OTHER PUBLICATIONS

Accession No. H98105 (Oct. 22, 2001).*
International Search Report for PCT/EP2009/053121, mailed Oct. 20, 2009.
Hoskins, J. et al., "Genome of the Bacterium *Streptococcus pneumoniae* Strain R6", Journal of Bacteriology, vol. 183, No. 19, (Oct. 1, 2001), pp. 5709-5717.
Ministero Dell 'Istruzione, Dell Universita e Della Ricerca, "Caratterizzazione ed applicazioni biotecnologiche di antigeni di *Streptococcus pneumoniae*, identificati mediante librerie di tipo "lambda display" da genoma complete", [Online], Programmi Di Ricerca, (2005), pp. 1-2.
Ng et al., "Regulation of the pspA virulence factor genes by the phosphorylated VicR (YycF) response regulator in *Streptococcus pneumoniae*", Journal of Bacteriology, vol. 187, No. 21, (Nov. 2005), pp. 7444-7459.
Beghetto, E. et al., "Discovery of novel *Streptococcus pneumoniae* antigens by screening a whole-genome lambda-display library", FEMS Microbiology Letters, vol. 262, No. 1, (Sep. 2006), pp. 14-21.

* cited by examiner

*Primary Examiner* — Padma Baskar
(74) *Attorney, Agent, or Firm* — Nixon & Vanderhye P.C.

(57) ABSTRACT

Antigenic protein fragments of *Streptococcus pneumoniae* to be used for the preparation of a medicament for the prevention and the treatment of bacterial infections and a method for the detection thereof, and related compositions using said epitopes, are disclosed.

3 Claims, 19 Drawing Sheets

```
spr1370
D39        MSEKSREEEKLSFKEQILRDLEKVKGYDEVLKEDEAVVRTPANEPSAEELMADSLSTVEE
R6         MSEKSREEEKLSFKEQILRDLEKVKGYDEVLKEDEAVVRTPANEPSAEELMADSLSTVEE
SP6-BS73   MSEKSREEEKLSFKEQILRDLEKVKGYDEVLKEDEAVVRTPANEPSTEELMADSLSTVEE
SP19-BS75  MSEKSREEEKLSFKEQILRDLEKVKGYDEVLKEDEAVVRTPANEPSAEELMADSLSTVEE
TIGR4      MSEKSREEEKLSFKEQILRDLEKVKGYDEVLKEDEAVVRTPANEPSAEELMADSLSTVEE
SP11-BS70  MSEKSREEEKLSFKEQILRDLEKVKGYDEVLKEDEAVVRTPANEPSTEELMADSLSTVEE
SP23-BS72  MSEKSREEEKLSFKEQILRDLEKVKGYDEVLKEDEAVVRTPANEPSTEELMADSLSTVEE
SP9-BS68   MSEKSREEEKLSFKEQILRDLEKVKGYDEVLKEDEAVVRTPANEPSAEELMADSLSTVEE
SP14-BS69  MSEKSREEEKLSFKEQILRDLEKVKGYDEVLKEDEAVVRTPANEPSAEELMTDSLSTVEE
SP3-BS71   MSEKSREEEKLSFKEQILRDLEKVKGYDEVLKEDEAVVRTPANEPSAEELMADSLSTVEE
           ************************************************:.*********

D39        IMRKAPTVPTHPSQGVPASPADEIQRETPGVPSHP---SQDVPSSPAEESGSRPGPGPVR
R6         IMRKAPTVPTHPSQGVPASPADEIQRETPGVPSHP---SQDVPSSPAEESGSRPGPGPVR
SP6-BS73   IMRKAPTVPTHPSQGVPASPADEIQRETPGVPSHP---SQDVPSSPAEESGSRPGPGPVR
SP19-BS75  IMRKAPTVPTHPSQGVPASPADEIQRETPGVPSHP---SQDVPSSPAEESGSRPGPGPVR
TIGR4      IMRKAPTVPTHPSQGVPASPADEIQRETPGVPSHP---SQDVPSSPAEESGSRPGPGPVR
SP11-BS70  IMRKAPTVPTHPSQGVPASPADEIQRETPGVPSHP---SQDVPSSPAEESGSRPGPGPVR
SP23-BS72  IMRKAPTVPTHPSQGVPASPADEIQRETPGVPSHP---SQDVPSSPAEESGSRPGPGPVR
SP9-BS68   IMRKAPTVPTHPSQGVPASPADEIQRETPGVPSHP---SQDVPSSPAEESGSRPGPGPVR
SP14-BS69  IMRKAPTVPTHPSQGVPASPADEIQRETPGVPSHPSQDVPSSPAEESGSRPGPGPVR
SP3-BS71   IMRKAPTVSTHPSQGVPASPADEIQRETPGVPSHP---SQDVPSSPAEESGSRPGPGPVR
           ********.*************************   ***********************
```

FIG 3A

```
D39         PKKLEREYNETPTRVAVSYTTAEKKAEQAGPETPTPATETVDIIRDTSRRSRREGAKPAK
R6          PKKLEREYNETPTRVAVSYTTAEKKAEQAGPETPTPATETVDIIRDTSRRSRREGAKPAK
SP6-BS73    PKKLEREYNETPTRVAVSYTTAEKKAEQAGPETPTPATETVDIIRDTSRRSRREGAKPAK
SP19-BS75   PKKLEREYNETPTRVAVSYTTAEKKAEQAGPETPTPATETVDIIRDTSRRSRREGAKPVK
TIGR4       PKKLEREYNETPTRVAVSYTTAEKKAEQAGPETPTPATETVDIIRDTSRRSRREGAKPVK
SP11-BS70   PKKLEREYNETPTRVAVSYTTAEKKAEQAGPETPTPATETVDIIRDTSRRSRREGAKPVK
SP23-BS72   PKKLEREYNETPTRVAVSYTTAEKKAEQAGPATPTPATETVDIIRDTSRRSRREGAKPVK
SP9-BS68    PKKLEREYNETPTRVAVSYTTAEKKAEQAGPETPTPATETVDIISDTSRRSRREGAKPVK
SP14-BS69   PKKLEREYNETPTRVAVSYTTAEKKAEQAGPETPTPATETVDIISDTSRRSRREGAKPVN
SP3-BS71    PKKLEREYNETPTRVAVSYTTAEKKAEQAGPETPTPATETVDIIRDTSRRSRREGAKPVK
            *********************************** ***************** ****:

D39         PKKEKKSHVKAFVISFLVFLALLSAGGYFGYQYVLDSLLPIDANSKKYVTVGIPEGSNVQ
R6          PKKEKKSHVKAFVISFLVFLALLSAGGYFGYQYVLDSLLPIDANSKKYVTVGIPEGSNVQ
SP6-BS73    PKKEKKSHVKAFVISFLVFLALLSAGGYFGYQYVLDSLLPIDANSKKYVTVGIPEGSNVQ
SP19-BS75   PKKEKKSHVKAFVISFLVFLALLSAGGYFGYQYVLDSLLPIDANSKKYVTVGIPEGSNVQ
TIGR4       PKKEKKSHVKAFVISFLVFLALLSAGGYFGYQYVLDSLLPIDANSKKYVTVGIPEGSNVQ
SP11-BS70   PKKEKKSHVKAFVISFLVFLALLSAGGYFGYQYVLDSLLPIDANSKKYVTVGIPEGSNVQ
SP23-BS72   PKKEKKSHVKAFVISFLVFLALLSAGGYFGYQYVLDSLLPIDANSKKYVTVGIPEGSNVQ
SP9-BS68    PKKEKKSHVKAFVISFLVFLALLSAGGYFGYQYVLDSLLPIDANSKKYVTVGIPEGSNVQ
SP14-BS69   PKKEKKSHVKAFVISFLVFLALLSAGGYFGYQYVLDSLLPIDANSKKYVTVGIPEGSNVQ
SP3-BS71    PKKEKKSHVKAFVISFLVFLALLSAGGYFGYQYVLDSLLPIDANSKKYVTVGIPEGSNVQ
            ************************************************************
```

FIG 3B

```
D39           EIGTTLEKAGLVKHGLIFSFYAKYKNYTDLKAGYYNLQKSMSTEDLLKELQKGGTDEPQE
R6            EIGTTLEKAGLVKHGLIFSFYAKYKNYTDLKAGYYNLQKSMSTEDLLKELQKGGTDEPQE
SP6-BS73      EIGTTLEKAGLVKHGLIFSFYAKYKNYTDLKAGYYNLQKSMSTEDLLKELQKGGTDEPQE
SP19-BS75     EIGTTLEKAGLVKHGLIFSFYAKYKNYTDLKAGYYNLQKSMSTEDLLKELQKGGTDEPQE
TIGR4         EIGTTLEKAGLVKHGLIFSFYAKYKNYTDLKAGYYNLQKSMSTEDLLKELQKGGTDEPQE
SP11-BS70     EIGTTLEKAGLVKHGLIFSFYAKYKNYTDLKAGYYNLQKSMSTEDLLKELQKGGTDEPQE
SP23-BS72     EIGTTLEKAGLVKHGLIFSFYAKYKNYTDLKAGYYNLQKSMSTEDLLKELQKGGTDEPQE
SP9-BS68      EIGTTLEKAGLVKHGLIFSFYAKYKNYTDLKAGYYNLQKSMSTEDLLKELQKGGTDEPQE
SP14-BS69     EIGTTLEKAGLVKHGLIFSFYAKYKNYTDLKAGYYNLQKSMSTEDLLKELQKGGTDEPQE
SP3-BS71      EIGTTLEKAGLIKHGLIFSFYAKYKNYTDLKAGYYNLQKSMSTEDLLKELQKGGTDEPQE
              ***********:************************************************

D39           PVLATLTIPEGYTLDQIAQTVGQLQGDFKESLTAEAFLAKVQDETFISQAVAKYPTLLES
R6            PVLATLTIPEGYTLDQIAQTVGQLQGDFKESLTAEAFLAKVQDETFISQAVAKYPTLLES
SP6-BS73      PVLATLTIPEGYTLDQIAQTVGQLQGDFKESLTAEAFLAKVQDETFISQAVAKYPTLLES
SP19-BS75     PVLATLTIPEGYTLDQIAQTVGQLQGDFKESLTAEAFLAKVQDETFISQAVAKYPTLLES
TIGR4         PVLATLTIPEGYTLDQIAQTVGQLQGDFKESLTAEAFLAKVQDETFISQAVAKYPTLLES
SP11-BS70     PVLATLTIPEGYTLDQIAQAVGQLQGDFKESLTAEAFLAKVQDETFISQAVAKYPTLLES
SP23-BS72     PVLATLTIPEGYTLDQIAQAVGQLQGDFKESLTAEAFLAKVQDETFISQAVAKYPTLLES
SP9-BS68      PVLATLTIPEGYTLDQIAQAVGQLQGDFKESLTAETFLAKVQDETFISQAVAKYPTLLES
SP14-BS69     PVLATLTIPEGYTLDQIAQTVGQLQGDFKESLTAEAFLAKVQDETFISQAVAKYPTLLES
SP3-BS71      PVLATLTIPEGYTLDQIAQTVGQLQGDFKESLTAEAFLAKVQDETFISQAVAKYPTLLES
              *******************:***************:************************
```

FIG 3C

```
D39        LPVKDSGARYRLEGYLFPATYSIKESTTIESLIDEMLAAMDKNLSLYYSTIKSKNLTVNE
R6         LPVKDSGARYRLEGYLFPATYSIKESTTIESLIDEMLAAMDKNLSLYYSTIKSKNLTVNE
SP6-BS73   LPVKDSGARYRLEGYLFPATYSIKESTTIESLIDEMLAAMDKNLSPYYSTIKSKNLTVNE
SP19-BS75  LPVKDSGARYRLEGYLFPATYSIKESTTIESLIDEMLAAMDKNLSPYYSTIKSKNLTVNE
TIGR4      LPVKDSGARYRLEGYLFPATYSIKESTTIESLIDEMLAAMDKNLSPYYSTIKSKNLTVNE
SP11-BS70  LPVKDSGARYRLEGYLFPATYSIKESTTIESLIDEMLAAMDKNLSPYYSTIKSKNLTINE
SP23-BS72  LPVKDSGARYRLEGYLFPATYSIKESTTIESLIDEMLAAMDKNLSPYYSTIKSKNLTVNE
SP9-BS68   LPVKDSGARYRLEGYLFPATYSIKESTTIESLIDEMLAAMDKNLSPYYSTIKSKNLTVNE
SP14-BS69  LPVKDSGARYRLEGYLFPATYSIKESTTIESLIDEMLAAMDKNLSPYYSTIKSKNLTVNE
SP3-BS71   LPVKDSGARYRLEGYLFPATYSIKESTTIESLIDEMLAAMDKNLSPYYSTIKSKNLTVNE
           ********************************************** *********:**

D39        LLTIASLVEKEGAKTEDRKLIAGVFYNRLNRDMPLQSNIAILYAQGKLGQNISLAEDVAI
R6         LLTIASLVEKEGAKTEDRKLIAGVFYNRLNRDMPLQSNIAILYAQGKLGQNISLAEDVAI
SP6-BS73   LLTIASLVEKEGAKTEDRKLIAGVFYNRLNRDMPLQSNIAILYAQGKLGQNISLAEDVAI
SP19-BS75  LLTIASLVEKEGAKTEDRKLIAGVFYNRLNRDMPLQSNIAILYAQGKLGQNISLAEDVAI
TIGR4      LLTIASLVEKEGAKTEDRKLIAGVFYNRLNRDMPLQSNIAILYAQGKLGQNISLAEDVAI
SP11-BS70  LLTIASLVEKEGAKTEDRKLIAGVFYNRLNRDMPLQSNIAILYAQGKLGQNISLAEDVAI
SP23-BS72  LLTIASLVEKEGAKTEDRKLIAGVFYNRLNRDMPLQSNIAILYAQGKLGQNISLAEDVAI
SP9-BS68   LLTIASLVEKEGAKTEDRKLIAGVFYNRLNRDMPLQSNIAILYAQGKLGQNISLAEDVAI
SP14-BS69  LLTIASLVEKEGAKTEDRKLIAGVFYNRLNRDMPLQSNIAILYAQGKLGQNISLAEDVAI
SP3-BS71   LLTIASLVEKEGAKTEDRKLIAGVFYNRLNRDMPLQSNIAILYAQGKLGQNISLAEDVAI
           ************************************************************
```

FIG 3D

```
D39          DTNIDSPYNVYKNVGLMPGPVDSPSLDAIESSINQTKSDNLYFVADVTEGKVYYANNQED
R6           DTNIDSPYNVYKNVGLMPGPVDSPSLDAIESSINQTKSDNLYFVADVTEGKVYYANNQED
SP6-BS73     DTNIDSPYNVYKNVGLMPGPVDSPSLDAIESSINQTKSDNLYFVADVTEGKVYYANNQED
SP19-BS75    DTNIDSPYNVYKNVGLMPGPVDSPSLDAIESSINQTKSDNLYFVADVTEGKVYYANNQED
TIGR4        DTNIDSPYNVYKNVGLMPGPVDSPSLDAIESSINQTKSDNLYFVADVTEGKVYYANNQED
SP11-BS70    DTDIDSPYNVYKNVGLMPGPVDSPSLDAIESSINQTKSDNLYFVADVTEGKVYYANNQED
SP23-BS72    DTNIDSPYNVYKNVGLMPGPVDSPSLDAIESSINQTKSDNLYFVADVTEGKVYYANNQED
SP9-BS68     DTNIDSPYNVYKNVGLMPGPVDSPSLDAIESSINQTKSDNLYFVADVTEGKVYYANNQED
SP14-BS69    DTNIDSPYNVYKNVGLMPGPVDSPSLDAIESSINQTKSDNLYFVADVTEGKVYYANNQED
SP3-BS71     DTNIDSPYNVYKNVGLMPGPVDSPSLDAIESSINQTKSDTLLCSRCHRRQGLLC------
             **:***********************************.*      . :   :

D39          HDRNVAEHVNSKLN
R6           HDRNVAEHVNSKLN
SP6-BS73     HDRNVAEHVNSKLN
SP19-BS75    HDRNVAEHVNSKLN
TIGR4        HDRNVAEHVNSKLN
SP11-BS70    HDRNVAEHVNSKLN
SP23-BS72    HDRNVAEHVNSKLN
SP9-BS68     HDRNVAEHVNSKLN
SP14-BS69    HDRNVAEHVNSKLN
SP3-BS71     --------------
```

FIG 3E

```
sprl875

D39         MKKRMLLASTVALSFAPVLATQAEEVLWTARSVEQIQNDLTKTDNKTSYTVQYGDTLSTI
R6          MKKRMLLASTVALSFAPVLATQAEEVLWTARSVEQIQNDLTKTDNKTSYTVQYGDTLSTI
SP23-BS72   MKKRMLLASTVALSFAPVLATQAEEVLWTARSVEQIQNDLTKTDNKTSYTVQYGDTLSTI
SP14-BS69   MKKRMLLASTVALSFAPVLATQAEEVLWTARSVEQIQNDLTKTDNKTSYTVQYGDTLSTI
SP19-BS75   MKKRMLLASTVALSFAPVLATQAEEVLWTARSVEQIQNDLTKTDNKTSYTVQYGDTLSTI
SP3-BS71    ----MLLASTVALSFAPVLATQAEEVLWTARSVEQIQNDLTKTDNKTSYTVQYGDTLSTI
TIGR4       MKKRMLLASTVALSFAPVLATQAEEVLWTARSVEQIQNDLTKTDNKTSYTVQYGDTLSTI
SP18-BS74   MKKRMLLASTVALSFAPVLATQAEEVLWTARSVEQIQNDLTKTDNKTSYTVQYGDTLSTI
SP11-BS70   MKKRMLLASTVALSFAPVLATQAEEVLWTARSVEQIQNDLTKTDNKTSYTVQYGDTLSTI
SP9-BS68    MKKRMLLASTVALSFAPVLATQAEEVLWTARSVEQIQNDLTKTDNKTSYTVQYGDTLSTI
SP6-BS73    ----MLLASTVALSFAPVLATQAEEVLWTARSVEQIQNDLTKTDNKTSYTVQYGDTLSTI
            *   ********************************************************

D39         AEALGVDVTVLANLNKITNMDLIFPETVLTTTVNEAEEVTEVEIQTPQADSSEEVTTATA
R6          AEALGVDVTVLANLNKITNMDLIFPETVLTTTVNEAEEVTEVEIQTPQADSSEEVTTATA
SP23-BS72   AEALGVDVTVLANLNKITNMDLIFPETVLTTTVNEAEEVTEVEIQTPQADSSEEVTTATA
SP14-BS69   AEALGVDVTVLANLNKITNMDLIFPETVLTTTVNEAEEVTEVEIQTPQADSSEEVTTATA
SP19-BS75   AEALGVDVTVLANLNKITNMDLIFPETVLTTTVNEAEEVTEVEIQTPQADSSEEVTTATA
SP3-BS71    AEALGVDVTVLANLNKITNMDLIFPETVLTTTVNEAEEVTEVEIQTPQADSSEEVTTATA
TIGR4       AEALGVDVTVLANLNKITNMDLIFPETVLTTTVNEAEEVTEVEIQTPQADSSEEVTTATA
SP18-BS74   AEALGVDVTVLANLNKITNMDLIFPETVLTTTVNEAEEVTEVEIQTPQADSSEEVTTATA
SP11-BS70   AEALGVDVTVLANLNKITNMDLIFPETVLTTTVNEAEEVTEVEIQTPQADSSEEVTTATA
SP9-BS68    AEALGVDVTVLANLNKITNMDLIFPETVLTTTVNEAEEVTEVEIQTPQADSSEEVTTATA
SP6-BS73    AEALDVDVTVLANLNKITNMDLIFPETVLTTTVNEAEEVTEVEIQTPQADSSEEVTTATA
            ****.*******************************************************
```

FIG 4A

```
D39         DLTTNQVTVDDQTVQVADLSQPIAEAPKEVASSSEVTKTVIASEEVAPSTGTSVPEEQTA
R6          DLTTNQVTVDDQTVQVADLSQPIAEAPKEVASSSEVTKTVIASEEVAPSTGTSVPEEQTA
SP23-BS72   DLTTNQVTVDDQTVQVADLSQPIAEAPKEVASSSEVTKTVIASEEVAPSTGTSVPEEQTA
SP14-BS69   DLTTNQVTVDDQTVQVADLSQPIAEAPKEVASSSEVTKTVIASEEVAPSTGTSVPEEQTT
SP19-BS75   DLTTNQVTVDDQTVQVADLSQPIAEAPKEVASSSEVTKTVIASEEVAPSTGTSVPEEQTT
SP3-BS71    DLTTNQVTVDDQTVQVADLSQPIAEAPKEVASSSEVTKTVIASEEVAPSTGTSVPEEQTA
TIGR4       DLTTNQVTVDDQTVQVADLSQPIAEV------------TKTVIASEEVAPSTGTSVPEEQTA
SP18-BS74   DLTTNQVTVDDQTVQVADLSQPIAEV------------TKTVIASEEVAPSTGTSVPEEQTT
SP11-BS70   DLTTNQVTVDDQTVQVADLSQPIAEV------------TKTVIASEEVAPSTGTSVPEEQTT
SP9-BS68    DLTTNQVTVDVQTVQVADLSQPIAEAPKEVASSSEVTKTVIASEEVAPSTGTSVPEEQTA
SP6-BS73    DLTTNQVTVDDQTVQVADLSQPIAEAPKEVASNSEVAETVTAAEEVALSTDSTTPEGQPA
            *** * ************ ***********           ** ** .:: **  . :

D39         ETSSAVAEEAPQETTPAEKQETQTSPQAASAVEATTT-----------SSEAKEVASSN
R6          ETSSAVAEEAPQETTPAEKQETQTSPQAASAVEATTT-----------SSEAKEVASSN
SP23-BS72   ETSSAVAEEAPQETTPGEKQETPQAASPQAASAVEATTT-----------SSEAKEVASSN
SP14-BS69   ETTRPVEEATPQETTPAEKQETQAASPQAASAVEVTTT-----------SSEAKEVASSN
SP19-BS75   ETSSAVAEEAPQETTPAEKQETQVSSQTESAVEATTMPVEEKATETTATSSEAKEVASSN
SP3-BS71    ETTRPVEEATPQETTPAEKQETQASPQAALAVEATTT-----------SSEAKEVASSN
TIGR4       ETTRPVEEATPQETTPAEKQETQASPQAASAVEVTTT-----------SSEAKEVASSN
SP18-BS74   ETTRPVEEATPQETTPAEKQETQAASPQAASAVEVTTT-----------SSEAKEVASSN
SP11-BS70   ETTRPVEEATPQETTPAEKQETQASPQAASAVEVTTT-----------SSEAKEVASSN
SP9-BS68    ETTRPVEEATPQETTPAKKQETQVSSQTESAVEATTMPVEEKATETTATSSEAKEVASSN
SP6-BS73    ETSPVEEVAPQATTLAEKQETQVSSQTESAVEATTMPVEEKATETTATSSEAKEVASSN
            ** :  ::  * ** . .::****  .:   *** **           ***********
```

FIG 4B

```
D39         GATAAVSTYQPEETKIISTTYEAPAAPDYAGLAVAKSENAGLQPQTAAFKEEIANLFGIT
R6          GATAAVSTYQPEETKIISTTYEAPAAPDYAGLAVAKSENAGLQPQTAAFKEEIANLFGIT
SP23-BS72   GATAAVSTYQPEETKIISTTYEAPAAPDYAGLAVAKSENAGLQPQTAAFKEEIANLFGIT
SP14-BS69   GATAAVSTYQPEETKIISTTYEAPAAPDYAGLAVAKSENAGLQPQTAAFKEEIANLFGIT
SP19-BS75   GATAAVSTYQPEETKIISTTYEAPAAPDYAGLAVAKSENAGLQPQTAAFKEEIANLFGIT
SP3-BS71    GATAAVSTYQSEETKVISTTYEAPAAPDYAGLAVAKSENAGLQPQTAAFKEEIANLFGIT
TIGR4       GATAAVSTYQPEETKIISTTYEAPAAPDYAGLAVAKSENAGLQPQTAAFKEEIANLFGIT
SP18-BS74   GATAAVSTYQPEETKIISTTYEAPAAPDYAGLAVAKSENAGLQPQTAAFKEEIANLFGIT
SP11-BS70   GATAAVSTYQPEETKVISTTYEAPAAPDYAGLAVAKSENAGLQPQTAAFKEEIANLFGIT
SP9-BS68    GATAAVSTYQPEETKVISTTYEAPAAPDYAGLAVAKSENAGLQPQTAAFKEEIANLFGIT
SP6-BS73    GATAAVSTYQPEETKTISTTYEAPAAPDYAGLAVAKSENAGLQPQTAAFKEEIANLFGIT
            **********:****:********************************************

D39         SFSGYRPGDSGDHGKGLAIDFMVPERSELGDKIAEYAIQNMASRGISYIIWKQRFYAPFD
R6          SFSGYRPGDSGDHGKGLAIDFMVPERSELGDKIAEYAIQNMASRGISYIIWKQRFYAPFD
SP23-BS72   SFSGYRPGDSGDHGKGLAIDFMVPERSELGDKIAEYAIQNMASRGISYIIWKQRFYAPFD
SP14-BS69   SFSGYRPGDSGDHGKGLAIDFMVPESSELGDKIAEYAIQNMASRGISYIIWKQRFYAPFD
SP19-BS75   SFSGYRPGDSGDHGKGLAIDFMVPEHSELGDKIAEYAIQNMASRGISYIIWKQRFYAPFD
SP3-BS71    SFSGYRPGDSGDHGKGLAIDFMVPESSELGDKIAEYAIQNMASRGISYIIWKQRFYAPFD
TIGR4       SFSGYRPGDSGDHGKGLAIDFMVPERSELGDKIAEYAIQNMASRGISYIIWKQRFYAPFD
SP18-BS74   SFSGYRPGDSGDHGKGLAIDFMVPERSELGDKIAEYAIQNMASRGISYIIWKQRFYAPFD
SP11-BS70   SFSGYRPGDSGDHGKGLAIDFMVPERSELGDKIAEYAIQNMASRGISYIIWKQRFYAPFD
SP9-BS68    SFSGYRPGDSGDHGKGLAIDFMVAERSELGDKIAEYAIQNMASRGISYIIWKQRFYAPFD
SP6-BS73    SFSGYRPGDSGDHGKGLAIDFMVPESSELGDKIAEYAIQNMASRGISYIIWKQRFYAPFD
            ***********************.:*:*********************************
```

FIG 4C

```
D39          SKYGPANTWNPMPDRGSVTENHYDHVHVSMNG
R6           SKYGPANTWNPMPDRGSVTENHYDHVHVSMNG
SP23-BS72    SKYGPANTWNPMPDRGSVTENHYDHVHVSMNG
SP14-BS69    SKYGPANTWNPMPDRGSVTENHYDHVHVSMNG
SP19-BS75    SKYGPANTWNPMPDRGSVTENHYDHVHVSMNG
SP3-BS71     SKYGPANTWNPMPDRGSVTENHYDHVHVSMNG
TIGR4        SKYGPANTWNPMPDRGSVTENHYDHVHVSMNG
SP18-BS74    SKYGPANTWNPMPDRGSVTENHYDHVHVSMNG
SP11-BS70    SKYGPANTWNPMPDRGSVTENHYDHVHVSMNG
SP9-BS68     SKYGPANTWNPMPDRGSVTENHYDHVHVSMNG
SP6-BS73     SKYGPANTWNPMPDRGSVTENHYDHVHVSMNG
             ********************************
```

FIG 4D

```
spr1120
D39       MKKKFLAFLLILFPIFSLGIAKAETIKIVSDTAYAPFEFKDSDQTYKGIDVDIINKVAEI
R6        MKKKFLAFLLILFPIFSLGIAKAETIKIVSDTAYAPFEFKDSDQTYKGIDVDIINKVAEI
TIGR4     MKKKFLAFLLILFPIFSLGIAKAETIKIVSDTAYAPFEFKDSDQTYKGIDVDIINKVAEI
SP3-BS71  MKKKFLAFLLILFPIFSLGIAKAETIKIVSDTAYAPFEFKDSDQTYKGIDVDIINKVAEI
SP11-BS70 MKKKFLAFLLILFPIFSLGIAKAETIKIVSDTAYAPFEFKDSDQTYKGIDVDIINKVAEI
SP23-BS72 MKKKFLAFLLILFPIFSLGIAKAETIKIVSDTAYAPFEFKDSDQTYKGIDVDIINKVAEI
SP9-BS68  MKKKFLAFLLILFPIFSLGIAKAETIKIVSDTAYAPFEFKDSDQTYKGIDVDIINKVAEI
SP6-BS73  MKKKFLAFLLILFPIFSLGIAKAETIKIVSDTAYAPFEFKDSDQTYKGIDVDIINKVAEI
          ************************************************************

D39       KGWNIQMSYPGFDAAVNAVQAGQADAIMAGMTKTKEREKVFTMSDTYYDTKVVIATTKSH
R6        KGWNIQMSYPGFDAAVNAVQAGQADAIMAGMTKTKEREKVFTMSDTYYDTKVVIATTKSH
TIGR4     KGWNIQMSYPGFDAAVNAVQAGQADAIMAGMTKTKEREKVFTMSDTYYDTKVVIATTKSH
SP3-BS71  KGWNIQMSYPGFDAAVNAVQAGQADAIMAGMTKTKEREKVFTMSDTYYDTKVVIATTKSH
SP11-BS70 KGWNIQMSYPGFDAAVNAVQAGQADAIMAGMTKTKEREKVFTMSDTYYDTKVVIATTKSH
SP23-BS72 KGWNIQMSYPGFDAAVNAVQAGQADAIMAGMTKTKEREKVFTMSDTYYDTKVVIATTKSH
SP9-BS68  KGWNIQMSYPGFDAAVNAVQAGQADAIMAGMTKTKEREKVFTMSDTYYDTKVVIATTKSH
SP6-BS73  KGWNIQMSYPGFDAAVNAVQAGQADAIMAGMTKTKEREKVFTMSDTYYDTKVVIATTKSH
          ************************************************************
```

FIG 5A

```
D39         KISKYDQLTGKTVGVKNGTAAQRFLETIKDKYGFTIKTFDTGDLMNNSLSAGAIDAMMDD
R6          KISKYDQLTGKTVGVKNGTAAQRFLETIKDKYGFTIKTFDTGDLMNNSLSAGAIDAMMDD
TIGR4       KISKYDQLTGKTVGVKNGTAAQRFLETIKDKYGFTIKTFDTGDLMNNSLSAGAIDAMMDD
SP3-BS71    KISKYDQLTGKTVGVKNGTAAQRFLETIKDKYGFTIKTFDTGDLMNNSLSAGAIDAMMDD
SP11-BS70   KISKYDQLTGKTVGVKNGTAAQRFLETIKDKYGFTIKTFDTGDLMNNSLSAGAIDAMMDD
SP23-BS72   KISKYDQLTGKTVGVKNGTAAQRFLETIKDKYGFTIKTFDTGDLMNNSLSAGAIDAMMDD
SP9-BS68    KISKYDQLTGKTVGVKNGTAAQRFLETIKDKYGFTIKTFDTGDLMNNSLSAGAIDAMMDD
SP6-BS73    KISKYDQLTGKTVGVKNGTAAQRFLETIKDKYGFTIKTFDTGDLMNNSLSAGAIDAMMDD
            ************************************************************

D39         KPVIEYAINQGQDLHIEMDGEAVGSFAFGVKKGSKYEHLVTEFNQALSEMKKDGSLDKII
R6          KPVIEYAINQGQDLHIEMDGEAVGSFAFGVKKGSKYEHLVTEFNQALSEMKKDGSLDKII
TIGR4       KPVIEYAINQGQDLHIEMDGEAVGSFAFGVKKGSKYEHLVTEFNQALSEMKKDGSLDKII
SP3-BS71    KPVIEYAINQGQDLHIEMDGEAVGSFAFGVKKGSKYEHLVTEFNQALSEMKKDGSLDKII
SP11-BS70   KPVIEYAINQGQDLHIEMDGEAVGSFAFGVKKGSKYEHLVTEFNQALAEMKKDGSLDKII
SP23-BS72   KPVIEYAINQGQDLHIEMDGEAVGSFAFGVKKGSKYEHLVTEFNQALAEMKKDGSLDKII
SP9-BS68    KPVIEYAINQGQDLHIEMDGEAVGSFAFGVKKGSKYEHLVTEFNQALAEMKKDGSLDKII
SP6-BS73    KPVIEYAINQGQDLHIEMDGEAVGSFAFGVKKGSKYEHLVTEFNQALAEMKKDGSLDKII
            ***********************************************..**********
```

FIG 5B

|  |  |
|---|---|
| D39 | KKWTASSSSAVPTTTTLAGLKAIPVKAKYIIASDSSFAPFVFQNSSNQYTGIDMELIKAI |
| R6 | KKWTASSSSAVPTTTTLAGLKAIPVKAKYIIASDSSFAPFVFQNSSNQYTGIDMELIKAI |
| TIGR4 | KKWTASSSSAVPTTTTLAGLKAIPVKAKYIIASDSSFAPFVFQNSSNQYTGIDMELIKAI |
| SP3-BS71 | KKWTASSSSAVPTTTTLAGLKAIPVKAKYIIASDSSFAPFVFQNSSNQYTGIDMELIKAI |
| SP11-BS70 | KKWTASSSSAVPTTTTLAGLKAIPVKAKYIIASDSSFAPFVFQNSSNQYTGIDMELIKAI |
| SP23-BS72 | KKWTASSSSAVPTTTTLAGLKAIPVKAKYIIASDSSFAPFVFQNSSNQYTGIDMELIKAI |
| SP9-BS68 | KKWTASSSSAVPTTTTLAGLKAIPVKAKYIIASDSSFAPFVFQNSSNQYTGIDMELIKAI |
| SP6-BS73 | KKWTASSSSAVPTTTTLAGLKAIPVKAKYIIASDSSFAPFVFQNSSNQYTGIDMELIKAI |
|  | ************************************************************ |
| D39 | AKDQGFEIEITNPGFDAAISAVQAGQADGIIAGMSVTDARKATFDFSESYYTANTILGVK |
| R6 | AKDQGFEIEITNPGFDAAISAVQAGQADGIIAGMSVTDARKATFDFSESYYTANTILGVK |
| TIGR4 | AKDQGFEIEITNPGFDAAISAVQAGQADGIIAGMSVTDARKATFDFSESYYTANTILGVK |
| SP3-BS71 | AKDQGFEIEITNPGFDAAISAVQAGQADGIIAGMSVTDARKATFDFSESYYTANTILGVK |
| SP11-BS70 | AKDQGFEIEITNPGFDAAISAVQAGQADGIIAGMSVTDARKATFDFSESYYTANTILGVK |
| SP23-BS72 | AKDQGFEIEITNPGFDAAISAVQAGQADGIIAGMSVTDARKATFDFSESYYTANTILGVK |
| SP9-BS68 | AKDQGFEIEITNPGFDAAISAVQAGQADGIIAGMSVTDARKATFDFSESYYTANTILGVK |
| SP6-BS73 | AKDQGFEIEITNPGFDAAISAVQAGQADGIIAGMSVTDARKATFDFSESYYTANTILGVK |
|  | ************************************************************ |

FIG 5C

```
D39         ESSNIASYEDLKGKTVGVKNGTASQTFLTENQSKYGYKIKTFADGSSMDDSLNTGAIDAV
R6          ESSNIASYEDLKGKTVGVKNGTASQTFLTENQSKYGYKIKTFADGSSMDDSLNTGAIDAV
TIGR4       ESSNIASYEDLKGKTVGVKNGTASQTFLTENQSKYGYKIKTFADGSSMDDSLNTGAIDAV
SP3-BS71    ESSNIASYEDLKGKTVGVKNGTASQTFLTENQSKYGYKIKTFADGSSMYDSLNTGAIDAV
SP11-BS70   ESSNIASYEDLKGKTVGVKNGTASQTFLTENQSKYGYKIKTFADGSSMYDSLNTGAIDAV
SP23-BS72   ESSNIASYEDLKGKTVGVKNGTASQTFLTENQSKYGYKIKTFADGSSMYDSLNTGAIDAV
SP9-BS68    ESSNIASYEDLKGKTVGVKNGTASQTFLTENQSKYGYKIKTFADGSSMYDSLNTGAIDAV
SP6-BS73    ESSNIASYEDLKGKTVGVKNGTASQTFLTENQSKYGYKIKTFADGSSMYDSLNTGAIDAV
            ***************************************** *****************

D39         MDDEPVLKYSISQGQKLKTPISGTPIGETAFAVKKGANPELIEMFNNGLANLKANGEFQK
R6          MDDEPVLKYSISQGQKLKTPISGTPIGETAFAVKKGANPELIEMFNNGLANLKANGEFQK
TIGR4       MDDEPVLKYSISQGQKLKTPISGTPIGETAFAVKKGANPELIEMFNNGLANLKANGEFQK
SP3-BS71    MDDEPVLKYSISQGQKLKTPISGTPIGETAFAVKKGANPELIEMFNNGLANLKANGEFQK
SP11-BS70   MDDEPVLKYSISQGQKLKTPISGTPIGETAFAVKKGANPELIEMFNNGLANLKANGEFQK
SP23-BS72   MDDEPVLKYSISQGQKLKTPISGTPIGETAFAVKKGANPELIEMFNNGLANLKANGEFQK
SP9-BS68    MDDEPVLKYSISQGQKLKTPISGTPIGETAFAVKKGANPELIEMFNNGLANLKANGEFQK
SP6-BS73    MDDEPVLKYSISQGQKLKTPISGTPIGETAFAVKKGANPELIEMFNNGLANLKANGEFQK
            ************************************************************
```

FIG 5D

| | |
|---|---|
| D39 | ILDKYLASESSTASTSTVDETTLWGLLQNNYKQLLSGLGITLALALISFAIAIVIGIIFG |
| R6 | ILDKYLASESSTASTSTVDETTLWGLLQNNYKQLLSGLGITLALALISFAIAIVIGIIFG |
| TIGR4 | ILDKYLASESSTASTSTVDETTLWGLLQNNYKQLLSGLGITLALALISFAIAIVIGIIFG |
| SP3-BS71 | ILDKYLASESSTASTSTVDETTLWGLLQNNYKQLLSGLGITLALALISFAIAIVIGIIFG |
| SP11-BS70 | ILDKYLASESSTASTSTVDETTLWGLLQNNYKQLLSGLGITLALALISFAIAIVIGIIFG |
| SP23-BS72 | ILDKYLASESSTASTSTVDETTLWGLLQNNYKQLLSGLGITLALALISFAIAIVIGIIFG |
| SP9-BS68 | ILDKYLASESSTASTSTVDETTLWGLLQNNYKQLLSGLGITLALALISFAIAIVIGIIFG |
| SP6-BS73 | ILDKYLASESSTASTSTVDETTLWGLLQNNYKQLLSGLGITLALALISFAIAIVIGIIFG |
| | ************************************************************ |
| D39 | MFSVSPYKSLRVISEIFVDVIRGIPLMILAAFIFWGIPNFIESITGQQSPINDFVAGTIA |
| R6 | MFSVSPYKSLRVISEIFVDVIRGIPLMILAAFIFWGIPNFIESITGQQSPINDFVAGTIA |
| TIGR4 | MFSVSPYKSLRVISEIFVDVIRGIPLMILAAFIFWGIPNFIESITGQQSPINDFVAGTIA |
| SP3-BS71 | MFSVSPYKSLRVISEIFVDVIRGIPLMILAAFIFWGIPNFIESITGQQSPINDFVAGTIA |
| SP11-BS70 | MFSVSPYKSLRVISEIFVDVIRGIPLMILAAFIFWGIPNFIESITGQQSPINDFVAGTIA |
| SP23-BS72 | MFSVSPYKSLRVISEIFVDVIRGIPLMILAAFIFWGIPNFIESITGQQSPINDFVAGTIA |
| SP9-BS68 | MFSVSPYKSLRVISEIFVDVIRGIPLMILAAFIFWGIPNFIESITGQQSPINDFVAGTIA |
| SP6-BS73 | MFSVSPYKSLRVISEIFVDVIRGIPLMILAAFIFWGIPNFIESITGQQSPINDFVAGTIA |
| | ************************************************************ |

FIG 5E

```
D39        LSLNAAAYIAEIVRGGIQAVPVGQMEASRSLGISYGKTMRKIILPQVTKLMLPNFVNQFV
R6         LSLNAAAYIAEIVRGGIQAVPVGQMEASRSLGISYGKTMRKIILPQVTKLMLPNFVNQFV
TIGR4      LSLNAAAYIAEIVRGGIQAVPVGQMEASRSLGISYGKTMRKIILPQATKLMLPNFVNQFV
SP3-BS71   LSLNAAAYIAEIVRGGIQAVPVGQMEASRSLGISYGKTMRKIILPQATKLMLPNFVNQFV
SP11-BS70  LSLNAAAYIAEIVRGGIQAVPVGQMEASRSLGISYGKTMRKIILPQATKLMLPNFVNQFV
SP23-BS72  LSLNAAAYIAEIVRGGIQAVPVGQMEASRSLGISYGKTMRKIILPQATKLMLPNFVNQFV
SP9-BS68   LSLNAAAYIAEIVRGGIQAVPVGQMEASRSLGISYGKTMRKIILPQSTKLMLPNFVNQFV
SP6-BS73   LSLNAAAYIAEIVRGGIQAVPVGQMEASRSLGISYGKTMRKIILPQATKLMLPNFVNQFV
           ************************************************************

D39        IALKDTTIVSAIGLVELFQTGKIIIARNYQSFKMYAILAIFYLVIITLLTRLAKRLEKRI
R6         IALKDTTIVSAIGLVELFQTGKIIIARNYQSFKMYAILAIFYLVIITLLTRLAKRLEKRI
TIGR4      IALKDTTIVSAIGLVELFQTGKIIIARNYQSFKMYAILAIFYLVIITLLTRLAKRLEKRI
SP3-BS71   IALKDTTIVSAIGLVELFQTGKIIIARNYQSFKMYAILAIFYLVIITLLTRLAKRLEKRI
SP11-BS70  IALKDTTIVSAIGLVELFQTGKIIIARNYQSFKMYAILAIFYLVIITLLTRLAKRLEKRI
SP23-BS72  IALKDTTIVSAIGLVELFQTGKIIIARNYQSFKMYAILAIFYLVIITLLTRLAKRLEKRI
SP9-BS68   IALKDTTIVSAIGLVELFQTGKIIIARNYQSFKMYAILAIFYLVIITLLTRLAKRLEKRI
SP6-BS73   IALKDTTIVSAIGLVELFQTGKIIIARNYQSFKMYAILAIFYLVIITLLTRLAKRLEKRI
           ************************************************************
```

FIG 5F

| | |
|---|---|
| D39 | R |
| R6 | R |
| TIGR4 | R |
| SP3-BS71 | R |
| SP11-BS70 | R |
| SP23-BS72 | R |
| SP9-BS68 | R |
| SP6-BS73 | S |

FIG 5G

ANTIGENIC PROTEIN FRAGMENTS OF STREPTOCOCCUS PNEUMONIAE

This application is the U.S. national phase of International Application No. PCT/EP2009/053121 filed 17 Mar. 2009, which designated the U.S. and claims priority to EP Application No. 08425177.6 filed 19 Mar. 2008, the entire contents of each of which are hereby incorporated by reference.

The present invention refers to the field of infectious diseases and more in particular it refers to antigenic protein fragments of *Streptococcus pneumoniae* to be used for the preparation of a medicament for the prevention and the treatment of bacterial infections and to a method for the detection thereof, and related compositions using said epitopes.

BACKGROUND OF THE INVENTION

*Streptococcus pneumoniae* is a major cause of invasive diseases such as meningitis, septicaemia and pneumonia. Approximately, one million children under 5 years of age die of pneumococcal disease annually (Jaffar S., et al., Vaccine, 1999; 18(7-8):633-40).

In countries where the incidence of *Neisseria meningitidis* and *Haemophilus influenzae* infections has drastically decreased through the introduction of vaccines against meningococci group C and *H. influenzae* type B, *S. pneumoniae* has become the major cause of meningitis and septicemia in children. In addition, the morbidity by *S. pneumoniae* through respiratory tract infections such as otitis media and sinusitis is enormous. Thirty to 50% of all patients with otitis media and a substantial percentage of cases of sinusitis and pneumonia are caused by pneumococci. Risk groups for serious pneumococcal disease include children under the age of 2 years, elderly and patients with immunodeficiencies (Pichichero M. E., et al., Pediatr. Infect. Dis. J., 1997; 16(1):72-4).

Nasopharyngeal colonization by *S. pneumoniae* is common: probably all humans are colonized with this organism at least once early in life. Especially in circumstances of crowding, as in day-care centers, nursing homes, hospitals and jails, the risk of colonization with pneumococci is high (Kellner J. D., et al., Arch. Pediatr. Adolesc. Med., 1999; 153(5):495-502; Nuorti J. P., et al., N. Engl. J. Med., 1998; 338(26):1861-8; Principi N., et al., Pediatr. Infect. Dis. J., 1999; 18(6):517-23).

Colonization is not usually followed by disease, since this is prevented by the innate and adaptive immune system. However, disturbance of homeostasis between host and pathogen, for example through viral infections, malnutrition or local damage of the mucosa, is associated with the development of invasive diseases (Hament J. M., et al., FEMS Immunol, Med, Microbiol. 1999; 26(3/4):189-95; Mulholland K., Vaccine, 1999; 17(Suppl 1):S79-84; Plotkowski M. C., et al., Am. Rev. Respir. Dis., 1986; 134(5):1040-4).

Despite the availability of various potential control measures, bacterial infections persist as major causes of morbidity and mortality. For example, despite the long-standing use of the 23-valent pneumococcal vaccine in specific at-risk group over the age of 2 years, the pneumococcus (*Streptococcus pneumoniae*) remains the leading cause of community-acquired pneumonia, otitis media and meningitis (Fedson D. S., Vaccine, 1999; 30; 17 Suppl. 1:S85-90. Review; Tuomanen E. I., Vaccine, 2000; 8; 19 Suppl. 1:S38-40. Review).

The recent introduction of the 7-valent conjugate pneumococcal vaccine into the childhood immunization schedules of some countries will likely reduce pneumococcal disease. However, this vaccine covers infections caused by only some pneumococcal serotypes and the replacement over time of these serotypes by resistant ones is a likely possibility. Problems exist also with therapeutic interventions, since many invasive *S. pneumoniae* strains are resistant to beta-lactam and other antibiotics (Neuman M. I., et al., J. Emerg. Med., 2007; 32(4):349-57).

In the last years, many pneumococcal proteins, including pneumolysin, surface protein A (PspA), surface adhesin A (PsaA), surface protein C (PspC), neuraminidase and autolysin, have been proposed as potential vaccine candidates (Briles D. E., et al., Vaccine, 2000; 8; 19 Suppl. 1:S87-95. Review).

In addition, intensive research is aimed towards discovery of novel targets for antibiotic treatment to overcome drug resistance (Bogaert D., et al., Vaccine, 2004; Sep. 28; 22(29-30):4014-20).

In the past years, one of the inventors and colleagues applied the technology of phage display to the identification of antigens of *Toxoplasma gondii* (Beghetto E., et al., Int. J. Parasitol., 2001; 31(14):1659-68; Beghetto E., et al., Int. J. Parasitol., 2003; 33(2):163-73; WO03/080839) and tumors (WO03/010199; WO03/011903).

In 2006 the present inventors focused their attention on the identification of pneumococcal proteins by using the technology of phage display.

The library screening allowed the isolation of phage clones carrying three distinct antigenic regions of a hypothetical pneumococcal protein, encoded by the open reading frame (ORF) spr0075 in the *S. pneumoniae* R6 strain genome sequence. This was the first identified *S. pneumoniae* gene product, having an antigenic function during infection (Beghetto et al., FEMS Microbial Lett., 2006; 262:14-21).

The spr0075 ORF in the R6 genome of *S. pneumoniae* encodes a putative protein of 1161 aa (GenBank accession no. NP357669), having an expected molecular mass of 123 kDa. Analysis of the Spr0075 protein sequence reveals the presence of: (a) a putative signal peptide, located between amino acids 1 and 40 (putative cleavage site aa 41), (b) six adjacent repeated regions (152 aa long) and (c) an LPxTG anchoring motif (Schneewind O Mihaylova-Petkov D & Model P 1993), in the C-terminal region (residues 1148-1152 aa). The spr0075 gene from the R6 strains is well preserved among several strains (type 19F, 6B, 2, 4, 23F), although the number of repeated regions may vary.

The protein Spr0075 is encoded by an spr0075 ORF in the R6 genome sequence (Hoskins J., et al., J. Bacteriol., 2001; 183:5709-5717) located between nucleotides 80186 and 83671.

Antigenic regions of Spr0075 protein reacted with more than 60% of sera, indicating a broad recognition of this protein antigen.

The analysis of virulence was conducted comparing FP242, the isogenic encapsulated mutant strain wherein spr0075 was deleted, with the wild type D 39.

Female CD mice, 5-8 week old were intravenously injected with 100 µl of PBS containing 70,000 CFU of D39 and the percentage of survival was followed up to 10 days. The results in FIG. 1 show that the virulence of the spr0075 deletion mutant was comparable to the wild type.

The efficacy of antipneumococcus capsular polysaccharide-based vaccines has been extensively debated, as the protection elicited by capsule polysaccharides is stringently serotype-specific (Hausdorff et al., 2005) and often unable to induce long-term memory response.

In the last generation of vaccines (Prevnar/Prevenar, 7-valent pneumococcal conjugate vaccine), purified capsular polysaccharides of seven *S. pneumoniae* strains were coupled with a protein carrier, in order to exceed the above limitations. The vaccine is effective in 97% of invasive diseases caused by vaccine serotypes and offers some protection against otitis media and pneumococcal carriage (Bogaert et al., 2004b).

Owing to the limited serotype coverage, risks of serotype replacement and the high cost of pneumococcal glycoconjugated vaccines, great interest in the development of formulations based on pneumococcal protein antigens has emerged in the last decade (Bogaert et al., 2004b).

It is strongly felt the need of vaccine compositions based on new antigen fragments, capable to recognize several serotypes and induce immune response to species with high variability or to different bacterial types.

In view of the prior art and starting from the results obtained on spr0075, the present inventors deeply investigated the genoma of pneumococcus by using the phage display technique, in order to find new antigens with the desired properties.

Surprisingly the inventors identified the sequences defined as spr1370, spr1875 and spr1120.

Said sequences are virulence factors isolated from *Streptococcus pneumoniae* and conserved in other bacteria. A virulence factor is a protein indispensable for bacteria propagation in the host.

Object of the present invention are antigen fragments and/or fragments containing an epitope with the following amino acid sequence:

SEQ SPM4
(SEQ ID NO: 1)
FISQAVAKYPTLLESLPVKDSGARYRLEGYLFPATYSIKESTTIESLI
DEMLAAMDKNLSLYYSTIKSKNLTVNELLTIASLVEKEGAKTEDRKLI
AGVFYNRLNRDMPLQSNIAILYAQGKLGQNISLAEDVAIDTNIDSPYN
VYKNVGLMPGPVDSPSLDAIESSINQTKSDNLYFVADVTEGKVYYANN
QEDHDRN

SEQ Spr1370
(SEQ ID NO: 2)
MSEKSREEEKLSFKEQILRDLEKVKGYDEVLKEDEAVVRTPANEPSAE
ELMADSLSTVEEIMRKAPTVPTHPSQGVPASPADEIQRETPGVPSHPS
QDVPSSPAEESGSRPGPGPVRPKKLEREYNETPTRVAVSYTTAEKKAE
QAGPETPTPATETVDIIRDTSRRSRREGAKPAKPKKEKKSHVKAFVIS
FLVFLALLSAGGYFGYQYVLDSLLPIDANSKKYVTVGIPEGSNVQEIG
TTLEKAGLVKHGLIFSFYAKYKNYTDLKAGYYNLQKSMSTEDLLKELQ
KGGTDEPQEPVLATLTIPEGYTLDQIAQTVGQLQGDFKESLTAEAFLA
KVQDETFISQAVAKYPTLLESLPVKDSGARYRLEGYLFPATYSIKEST
TIESLIDEMLAAMDKNLSLYYSTIKSKNLTVNELLTIASLVEKEGAKT
EDRKLIAGVFYNRLNRDMPLQSNIAILYAQGKLGQNISLAEDVAIDTN
IDSPYNVYKNVGLMPGPVDSPSLDAIESSINQTKSDNLYFVADVTEGK
VYYANNQEDHDRNVAEHVNSKLN

SEQ SPM8
(SEQ ID NO: 3)
GVKESSNIASYEDLKGKTVGVKNGTASQTFLTENQSKYGYKIKTFADG
SSMDDSLNTGAIDAVMDDEPVLKYSISQGQKLKTPISGTPIGETAFAV
KKGANPELIEMF

SEQ Spr1120
(SEQ ID NO: 4)
MKKKFLAFLLILFPIFSLGIAKAETIKIVSDTAYAPFEFKDSDQTYKG
IDVDIINKVAEIKGWNIQMSYPGFDAAVNAVQAGQADAIMAGMTKTKE
REKVFTMSDTYYDTKVVIATTKSHKISKYDQLTGKTVGVKNGTAAQRF
LETIKDKYGFTIKTFDTGDLMNNSLSAGAIDAMMDDKPVIEYAINQGQ
DLHIEMDGEAVGSFAFGVKKGSKYEHLVTEFNQALSEMKKDGSLDKII
KKWTASSSSAVPTTTTLAGLKAIPVKAKYIIASDSSFAPFVFQNSSNQ
YTGIDMELIKAIAKDQGFEIEITNPGFDAAISAVQAGQADGIIAGMSV
TDARKATFDFSESYYTANTILGVKESSNIASYEDLKGKTVGVKNGTAS
QTFLTENQSKYGYKIKTFADGSSMDDSLNTGAIDAVMDDEPVLKYSIS
QGQKLKTPISGTPIGETAFAVKKGANPELIEMFNNGLANLKANGEFQK
ILDKYLASESSTASTSTVDETTLWGLLQNNYKQLLSGLGITLALALIS
FAIAIVIGIIFGMFSVSPYKSLRVISEIFVDVIRGIPLMILAAFIFWG
IPNFIESITGQQSPINDFVAGTIALSLNAAAYIAEIVRGGIQAVPVGQ
MEASRSLGISYGKTMRKIILPQVTKLMLPNFVNQFVIALKDTTIVSAI
GLVELFQTGKIIIARNYQSFKMYAILAIFYLVIITLLTRLAKRLEKR
IR

SEQ R4
(SEQ ID NO: 5)
EQIQNDLTKTDNKTSYTVQYGDTLSTIAEALGVDVTVLANLNKITNMD
LIFPETVLTTTVNEAEEVTEVEIQTPQADSSEEVTTATADLTTNQVTV
DDQTVQVADLSQPIAEAPKEVASSSEVTKTVIASEEVAPSTGTSVPEE
QTAETSSAVAEEAPQET

SEQ Spr1875
(SEQ ID NO: 6)
MKKRMLLASTVALSFAPVLATQAEEVLWTARSVEQIQNDLTKTDNKTS
YTVQYGDTLSTIAEALGVDVTVLANLNKITNMDLIFPETVLTTTVNEA
EEVTEVEIQTPQADSSEEVTTATADLTTNQVTVDDQTVQVADLSQPIA
EAPKEVASSSEVTKTVIASEEVAPSTGTSVPEEQTAETSSAVAEEAPQ
ETTPAEKQETQTSPQAASAVEATTTSSEAKEVASSNGATAAVSTYQPE
ETKIISTTYEAPAAPDYAGLAVAKSENAGLQPQTAAFKEEIANLFGIT
SFSGYRPGDSGDHGKGLAIDFMVPERSELGDKIAEYAIQNMASRGISY
IIWKQRFYAPFDSKYGPANTWNPMPDRGSVTENHYDHVHVSMNG (wherein SEQ SPM4, SEQ SPM8 and SEQ R4 are the amino acid sequences of the fragments identified by using the technology of phage display while SEQ Spr1370, SEQ Spr1120 and SEQ Spr1875 are the amino acid sequences of the corresponding Open Reading Frame)

and the corresponding coding nucleotide sequence:

SEQ SPM4
(SEQ ID NO: 7)
TTTATCAGTCAAGCAGTAGCGAAATATCCTACTTTACTGGAAAGTTTG
CCTGTAAAAGACAGCGGTGCGCGTTATCGTTTGGAAGGATACCTTTTC
CCAGCTACATACTCTATCAAGGAAAGCACAACTATTGAGAGCTTGATT
GATGAGATGTTAGCTGCTATGGATAAGAACCTATCTCTTTACTATAGT
ACTATCAAATCTAAAAACTTGACTGTCAATGAGTTGTTGACCATTGCT
TCCTTGGTCGAAAAAGAAGGTGCCAAGACAGAAGATCGTAAGCTCATT
GCAGGTGTATTCTACAATCGTTTGAATCGTGATATGCCACTTCAAAGT
AATATTGCAATCTTGTATGCCCAAGGAAAACTGGGGCAAAATATCAGT
CTAGCTGAGGATGTTGCGATTGATACCAACATTGATTCACCTTATAAT
GTTTATAAAAATGTAGGTCTCATGCCTGGTCCAGTCGATAGTCCAAGT
CTGGATGCGATTGAGTCAAGCATCAATCAAACTAAGAGCGATAACCTC
TACTTTGTAGCAGATGTCACAGAAGGCAAGGTCTACTATGCTAACAAT
CAAGAAGACCACGACCGCA

SEQ SPM8
(SEQ ID NO: 8)
GGTGTCAAAGAATCAAGTAATATTGCTTCTTATGAAGATCTAAAAGGA
AAGACAGTCGGTGTTAAAAACGGAACTGCTTCTCAAACCTTCCTAACA
GAAAATCAAAGCAAATACGGCTACAAAATCAAAACCTTTGCTGATGGT
TCTTCAATGGATGACAGTTTAAACACTGGTGCCATTGATGCCGTTATG
GATGATGAACCTGTTCTCAAATATTCTATCAGCCAAGGTCAAAAATTG
AAAACTCCAATCTCTGGAACTCCAATCGGTGAAACAGCCTTTGCCGTT
AAAAAAGGAGCAAATCCAGAACTGATTGAAATGTTC

SEQ R4
(SEQ ID NO: 9)
GAGCAAATCCAAAACGATTTGACTAAAACGGACAACAAAACAAGTTAT
ACCGTACAGTATGGTGATACTTTGAGCACCATTGCAGAAGCCTTGGGT
GTAGATGTCACAGTGCTTGCGAATCTGAACAAAATCACTAATATGGAC
TTGATTTTCCCAGAAACTGTTTTGACAACGACTGTCAATGAAGCAGAA
GAAGTAACAGAAGTTGAAATCCAAACACCTCAAGCAGACTCTAGTGAA
GAAGTGACAACTGCGACAGCAGATTTGACCACTAATCAAGTGACCGTT
GATGATCAAACTGTTCAGGTTGCAGACCTTTCTCAACCAATTGCAGAA
GCTCCAAAAGAAGTAGCATCAAGTTCAGAAGTTACAAAGACAGTGATT
GCTTCTGAAGAAGTGGCACCATCTACGGGCACTTCTGTCCCAGAGGAG
CAAACGGCCGAAACAAGCAGTGCAGTTGCAGAAGAAGCTCCTCAGGAA
ACG and the hybridizing nucleotide sequences, also under stringent hybridization, thereof. In this contest the terms "hybridization" and "stringent" refer to the conventional hybridization techniques well known to the person skilled in this field (Buzdin A and Lukyanov S (eds) Nucleic Acids Hybridization Kluwer Academic Publishers Netherlands 2007).

Another object of the present invention is a method for the identification of the amino acid sequences above disclosed comprising the following steps:
a) obtaining a serum pool from subjects immunized with a killed bacterial strain;
b) administering to subjects the serum pool obtained in step a) to give immunized subjects;
c) collecting the sera from said immunized subjects obtained in step b), and
d) undergoing the sera of step c to phage display technique.)

In the context of the above method according to the present invention, a "subject" is for example a laboratory animal, such as a mouse.

Another object of the present invention is a method for the identification of the above antigen fragments and/or fragments containing epitopes by means of selection of libraries of cDNA or DNA fragments of *Streptococcus pneumoniae* with sera of subjects immunized with the killed *Streptococcus pneumoniae*.

A further object of the present invention is the use of said antigen fragments as active agents for the diagnosis of pneumococcal infections, in particular *Streptococcus pneumoniae* infections, *Streptococcus gordonii* infections, *Streptococcus sanguinis* infections, *Streptococcus thermophilus* infections, *Streptococcus suis* infections, *Streptococcus agalactiae* infections, *Streptococcus pyogenes* infections, *Streptococcus mutans* infections, *Enterococcus faecalis* infections, *Enterococcus faecium* infections, *Rhodococcus* sp. infections.

It is also object of the present invention, the use of said antigen fragments for the preparation of a medicament, preferably for the prevention or the treatment of pneumococcal infections, such as the ones listed above.

Are object of the present invention also the specific ligands such as natural host ligands (eg complement and other opsonins) or artificial ligands such as peptides selected with the above antigen using random peptide libraries and any molecules that bind to the above epitopes and the anti-epitope antibodies raised against said epitopes, and the use of at least one of said ligands and/or at least one of said antibodies for the preparation of means for the diagnosis of pneumococcal infections, such as the ones listed above.

Another object of the present invention is a method for the diagnosis of pneumococcal infections comprising the selection of sera of subjects affected by or suspected of being affected by said infection with the above antigen fragments and/or with at least one of the above ligands and/or at least one of the above antibodies and a diagnostic kit for pneumococcal infections.

A further object of the present invention is a pharmaceutical composition, particularly in the form of a vaccine, containing at least one of the above antigen fragments or one of the above sequences. Said composition is suitable for human and/or veterinary use.

These and other objects will be illustrated here below in detail, also by means of examples and figures, wherein:

FIG. 3 shows gene bank database sequence comparison of spr1370 (SEQ ID NOS 16-25 are disclosed respectively in order of appearance).

FIG. 4 shows gene bank database sequence comparison of spr1875 (SEQ ID NOS 26-36 are disclosed respectively in order of appearance).

FIG. 5 shows gene bank database sequence comparison of spr1120 (SEQ ID NOS 37-44 are disclosed respectively in order of appearance).

DETAILED DESCRIPTION OF THE INVENTION

Figure 1:
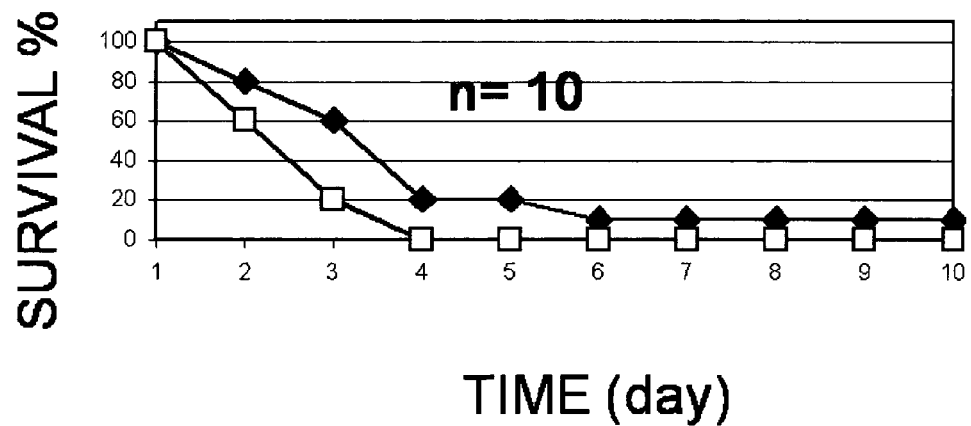
FIG. 1 shows comparative data on the virulence of wild type D39 and FP242.

All the definitions used herein are part of the common knowledge of a person skilled in this art and reference is made to the general scientific literature. Specific reference can be made to WO02/37115, WO03/080839, WO03/010199, WO03/011903 and WO2004/056851, which disclose and refer to the phage display technique The present inventors identified three new pneumococcal gene products by using the phage display technology that can be efficiently used as targets for drug treatment and immune-based measures to control bacterial infections, as well as means to diagnose pneumococcal disease. To reach this objective, they used bacteriophage lambda display library of pneumococcal whole genome for the screening with immune sera. They identified three previously unknown pneumococcal protein fragments encoded by open the reading frames (ORF), hereinafter defined as spr1370, spr1875 and spr1120.

Said protein fragments contained B-cell epitopes, and thus can be used for diagnostic purposes and immuno-based strategies for the prevention and treatment of bacterial infections.

Moreover, they showed that the entire products of the corresponding genes may likely represent important targets for drug therapy and prophylaxis.

Since these gene products are highly conserved among bacterial pathogens, they can be effectively used for controlling a number of different infectious diseases caused by microbes with similar sequences, as identified by homology searches in nucleic acid data bases using servers such as clustalW (www.ebi.ac.uk/clustalw/).

The selection from the desired phage display library is performed as known in the art from the above cited references (WO02/37115, WO03/080839, WO03/010199; WO03/011903 and WO2004/056851).

Briefly, to select the bacterial gene product from a display library, a serum pool is obtained from animals, preferably mice, immunized with the killed strain, resuspended and administered to animals, preferably via subcutaneous injection. Then, the sera from immunized animals are collected and used for the library screening.

The display library is affinity-selected using the immune serum pool and the resulting phage population is analyzed by phage ELISA. At the end of the selection procedures, the phage clones bearing protein sequences that matched with the genome sequence of the bacterial strain are identified.

The genome sequences above identified are then molecularly characterized by comparative analysis with other strains in gene bank databases.

The genome sequences identified, and the sequences that hybridize under stringent conditions, encode for amino acid sequences containing epitopes, generating an antibody response. Such amino acid sequences and fragments can be used for the preparation of pharmaceutical compositions, preferably vaccines.

The preparation of pharmaceutical compositions and vaccines is within the framework of general knowledge; for further reference purposes, the reader is referred to the patent literature cited and incorporated by reference in the present description. See for example WO2007/081583 and WO2007/071786 and the references cited therein.

The diagnostic method for detecting bacterial infections comprises the following steps:
 a) contacting a biological sample of a subject with at least one peptide of the present invention;
 b) detecting antigen-antibody complex formation.

Preferably, the biological sample is collected from the subject before executing step a).

The diagnostic kits which are object of the present invention are known to the expert in the field but, by the way of an example, the reader is referred to U.S. Pat. No. 6,265,176 and WO01/63283.

The following examples further illustrate the present invention.

EXAMPLES

Example 1

Selection from *S. pneumoniae* Lambda Display Library

To select pneumococcal gene products from a display library, a serum pool obtained from five mice (6-week-old CBA/Jico mice) immunized with the killed *S. pneumoniae* D39 strain was used. Briefly, $10^7$ CFU were re-suspended in Freund's adjuvant and administered to animals via subcutaneous injection at days 0 and 21. At day 35, sera from immunized mice were collected and used for library screening. Construction of the pneumococcal library has been previously described (Beghetto E., et al., Int. J. Parasitol., 2003; 33(2):163-73; Minenkova O., et al., Int. J. Cancer, 2003; 10; 106(4):534-44; Beghetto E., et al., FEMS Microbiol. Lett., 2006; 262(1):14-21).

In order to identify encoded protein fragments, the display library was affinity-selected using the immune serum pool. Three rounds of affinity-selection were performed and the resulting phage population was analyzed, after every round of selection, for its immunoreactivity by phage ELISA (Beghetto E., et al., FEMS Microbiol. Lett., 2006; 262(1):14-21). At the end of the selection procedures, phage clones bearing distinct protein regions that matched the genome sequence of *S. pneumoniae* R6 (GenBank accession no. AE007317) were identified.

Example 2

Molecular Characterization of the Gene Products

Three protein fragments named SPM4, R4, SPM8, encoded by regions of ORF spr1370, spr1875, and spr1120 respectively, were identified.
 ORF spr1370 consists of 1653 nucleotides and encodes for a hypothetical protein of 551 aa. The protein has a calculated molecular mass of 60.8 k Da and does not have a secretory signal peptide. Comparative analysis of the R6 strain-spr1370 gene with sequences from different pneumococci reveals that the protein is present in all the investigated strains belonging to different serotypes (19F, 6B, 2, 4, 23F).
 ORF spr1120 matches with the sequence of an ABC transporter membrane-spanning permease-glutamine transport gene. It encodes for a 731 aa-protein with a signal peptide of 67 aa length. The protein has a calculated molecular mass of 78.3 kDa.
 The 1140 nucleotide-long ORF spr1875 encodes for a 380 aa protein with a 25 aa-secretory signal peptide.

Example 3

Construction of the spr1370, spr1875 and spr1120 Gene Knockout Mutants

*S. pneumoniae* mutants were constructed by gene SOEing (Horton R. M., et al., Biotechniques, 1990; 8(5):528-35), as previously described (Iannelli F., et al., J. Bacteriol., 1999 April; 181(8):2652-4). In the mutants, the sprx gene was replaced by an antibiotic-resistance cassette (Pearce B. J., et al., Res Microbiol., 2002; 153(4):243-7), for this purpose, six oligonucleotide primers for each mutant were used. A first pair of primers was used to amplify the 5' flanking region, a second pair was used to amplify the 3' flanking region, and the last pair was used to generate an erythromycin resistance cassette.

The primers used are here listed:

```
1370-1:
                                        (SEQ ID NO: 10)
AAGTCAAGAGAAGAAGAGAA;

1370-2:
                                        (SEQ ID NO: 11)
ATCATCAACAATCACAAATCACTTTAGGCTTAGCGGGTTTTGCT;

1370-3:
                                        (SEQ ID NO: 12)
AGCTTCCAAGGAGCTAAAGAGGTTCTATCAAGGAAAGCACAACT;

1370-4:
                                        (SEQ ID NO: 13)
TTGATTGTTAGCATAGTAGACC;

IF188:
                                        (SEQ ID NO: 14)
AAGTGATTTGTGATTGTTGATG;

IF189:
                                        (SEQ ID NO: 15)
ACCTCTTTAGCTCCTTGGAAG.
```

The whole fragment, assembled by PCR reaction (Horton R., et al., Gene., 1989; 77:61-68), was used to transform *S. pneumoniae* D39 strain cells. The mutant construction was verified by PCR and sequencing. The spr1370, spr1875, and spr1120-deficient strains were named TF137, TF187 and TF112, respectively. Pneumococcal strains were grown in Todd-Hewitt (TH) broth in a 7% $CO_2$-enriched atmosphere at 37° C. Where necessary, streptomycin (500 µgml$^{-1}$) and erythromycin (1 µgml$^{-1}$) were used to select mutants.

Example 4

In Vivo and In Vitro Studies

*Streptococcus pneumoniae* D39 (wild type) and TF137, TF187 and TF112 mutant strains, were grown to mid log phase ($OD_{600}$nm=0.4) in 20 ml of TH broth. Importantly, no differences were found between any of the mutant strains and the parental one in their ability to grow in vitro. Cells were collected and washed twice, and then resuspended in PBS in a final volume of 2 ml. Six to eight-week old female CD1 mice were inoculated with diluted samples containing the indicated CFU by intravenous injection. Serial dilutions of the inoculums were plated on TH+1.5% agar, and incubated at 37° C. in 7% $CO_2$ to verify bacterial colony forming units (CFU/ml).

Figure 2:
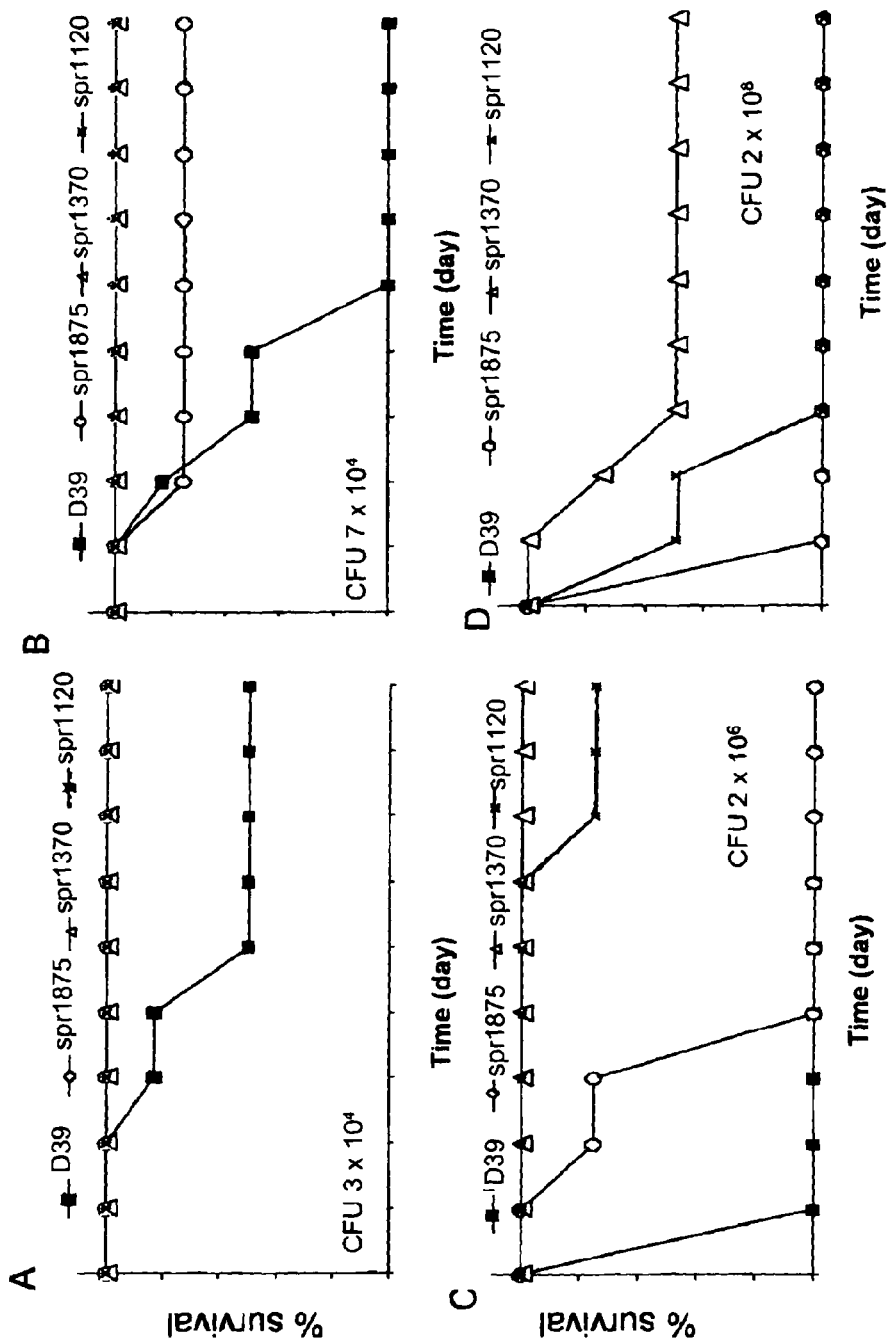
FIG. 2 shows the lethality induced by spr1370, spr1875 and spr1120 mutants.

FIG. 2 shows the virulence of TF137, TF187 and TF112 mutants compared to that of the D39 wild-type strain. Inoculation of $3 \times 10^4$ CFU of the wild-type strain resulted in rapid death of 50% of animals (panel A), while 7×10$^4$ CFU were sufficient to produce 100% lethality (panel B). In striking contrast the TF137 mutant, where the spr1370 gene was deleted, was totally impaired in causing lethality, even at doses of 2×10$^7$CFU. Only at doses of 2×10$^8$ half of the infected animals died (panel D). These data indicated that the virulence of the spr1370 mutant was approximately 4 orders of magnitude lower than that of the wild-type strain.

The figure also shows lethality of mice that were inoculated the TF187 and the TF112 strains, which were also considerably less virulent than the D39 wild-type strain. For example with the TF112 strain, in which the spr1120 gene was deleted, lethality was observed only at doses of 2×10$^6$ CFU or higher (panels C and D). The TF187 strain was also less virulent than the D39 mutant, although it did cause lethality at doses of 7×10$^4$ CFU or higher.

In further experiments (not shown) groups of mice were inoculated with 1×10$^7$ CFU of D39 or the TF137 mutant and sacrificed after 24 and 48 hours to examine the presence of bacteria in the blood and kidneys. While high bacterial counts were observed in mice inoculated with the D39 strain, no bacteria were observed in TF137-inoculated animals, confirming the inability of pneumococci to survive in vivo in the absence of the spr1370 gene.

Example 5

Gene Bank Sequence Comparison

The comparison with the sequences of other strains in the gene bank databases showed that spr1370 is conserved in *Streptococcus gordonii*, *Streptococcus sanguinis*, *Streptococcus mutans*, *Streptococcus thermophilus*, *Streptococcus suis*, and *Streptococcus agalactiae* (FIG. 3).

The comparison with the sequences of other strains in the gene bank databases showed that spr 1875 is conserved in *Streptococcus sanguinis*, *Streptococcus thermophilus*, *Streptococcus pyogenes*, *Streptococcus gordonii*, *Streptococcus agalactiae*, *Streptococcus suis* (FIG. 4).

The comparison with the sequences of other strains in the gene bank databases showed that spr 1120 is conserved in *Streptococcus sanguinis*, *Streptococcus mutans*, *Streptococcus suis*, *Streptococcus agalactiae*, *Streptococcus pyogenes*, *Streptococcus thermophilus*, *Lactococcus lactis*, *Streptococcus gordonii*, *Enterococcus faecalis*, *Enterococcus faecium*, *Rhodococcus sp* (FIG. 5).

Example 6

Immunoprotective Activities of the R4 Antigenic Polypeptide Encoded by spr1875

Figure 6:
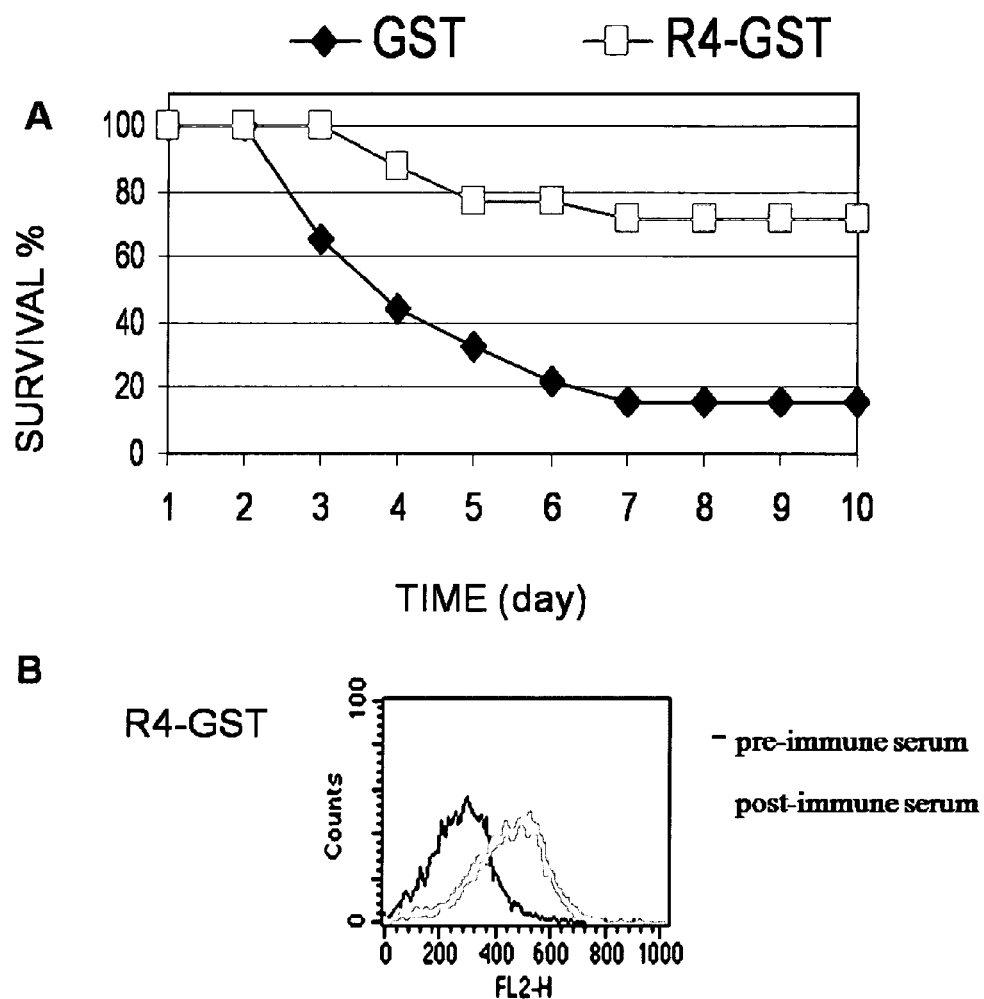
FIG. 6 shows the strong immunoprotective activities of R4, a polypeptide encoded by spr1875.

FIG. 6 shows the ability of a polypeptide (designated as R4 and encoded by spr1875) to protect, after immunization, mice against lethal pneumococcal infection. The R4 sequence was cloned into an expression vector and R4 was produced recombinantly fused to glutathione S transferase (GST), as previously described (Beghetto et al, FEMS Microbiol Lett, 2006; 262:1421). Mice were immunized with R4-GST for 3 times at days intervals in Freund's adjuvant and challenged intravenously with a lethal dose of the D39 *S. pneumoniae* strain. Control animals received GST only. While 13 out of 18 (72%) of the latter mice died, only 5 of the 18 mice immunized with R4-GST succumbed to infection (p<0.02 by Fisher exact test; FIG. 6A). Moreover, it has been shown that the R4 polypeptide is expressed on the surface of *S. pneumoniae*, i.e. it is in a position to be targeted by protective antibodies. This is evidenced in FIG. 6B by the ability of sera from R4-GST immunized animals to stain the D39 surface by indirect immunofluorescence, according to a previously described flow cytometry protocol (Grifantini R., et al., Nat. Biotechnol., 2002; 20(9):914-21). This example demonstrates that spr1875 and its products, with special reference to R4, are suitable candidates for vaccines against *S. pneumoniae* and other gram positive bacteria. It is of particular interest, in this context, that spr1875 is present in all of the pneumococcal strains whose genome has been sequenced. Moreover, as mentioned above, spr1875 is conserved in *Streptococcus sanguinis*, *Streptococcus thermophiles*, *Streptococcus pyogenes*, *Streptococcus gordonii*, *Streptococcus agalactiae* and *Streptococcus suis*. Therefore spr1875 (and homologous genes and gene products present in streptococci different from *S. pneumoniae*) could be used in the formulation of vaccines directed against the said and, possibly, additional bacterial pathogens.

Results

The data clearly established that the spr1370, spr1120 and the spr1875, encode for products that are required for in vivo growth of *Streptococcus pneumoniae* and for its ability to cause disease. Therefore these genes and their products are novel and important targets for the prevention or the therapy of pneumococcal diseases. Since at least portions of spr1120 and spr1875 are also present in other bacteria, these antigens may, in addition, be useful in the control of infections caused by bacteria different from pneumococci.

A pneumococcal strain devoid of the 1370 gene was almost completely unable to replicate in vivo. This mutant did not cause any lethality and no bacteria were detected at any time point in the blood or the organs of infected mice when using inocula lower than 2×10$^8$, i.e. at an extremely high dose. These striking results indicate that most likely the 1370 gene encodes of an important virulence factor, enabling *S. pneumoniae* to resist to antibacterial host defenses. Alternatively the 1370 gene product may be required for the synthesis of an essential nutritional factor, which is available in vitro cultures but not in vivo.

Similar considerations also apply to the products of the other discovered genes (spr1875, spr1120) that were shown here to play essential or important roles in *S. pneumoniae* virulence.

For example, the spr1875-encoded polypeptide R4 was capable of markedly protecting, after immunization, experimental animals against infection by *S. pneumoniae*. This underscores the utility of the genes and gene products described here, e.g. in the form of vaccines, for the control of infections by pathogenic bacteria expressing said genes, including *S. pneumoniae*.

The invention claimed is:

1. An isolated polypeptide consisting of amino acids 34-194 of SEQ ID NO: 6.

2. A vaccine composition comprising an isolated polypeptide consisting of amino acids 34-194 of SEQ ID NO: 6 and pharmaceutically acceptable carriers, or excipients and optionally adjuvants.

3. A kit comprising an isolated polypeptide consisting of amino acids 34-194 of SEQ ID NO: 6.

* * * * *

SEQUENCE LISTING

<160> NUMBER OF SEQ ID NOS: 44

<210> SEQ ID NO 1
<211> LENGTH: 199

```
<212> TYPE: PRT
<213> ORGANISM: Streptococcus pneumoniae

<400> SEQUENCE: 1

Phe Ile Ser Gln Ala Val Ala Lys Tyr Pro Thr Leu Leu Glu Ser Leu
 1               5                  10                  15

Pro Val Lys Asp Ser Gly Ala Arg Tyr Arg Leu Glu Gly Tyr Leu Phe
             20                  25                  30

Pro Ala Thr Tyr Ser Ile Lys Glu Ser Thr Thr Ile Glu Ser Leu Ile
         35                  40                  45

Asp Glu Met Leu Ala Ala Met Asp Lys Asn Leu Ser Leu Tyr Tyr Ser
     50                  55                  60

Thr Ile Lys Ser Lys Asn Leu Thr Val Asn Glu Leu Leu Thr Ile Ala
 65                  70                  75                  80

Ser Leu Val Glu Lys Glu Gly Ala Lys Thr Glu Asp Arg Lys Leu Ile
                 85                  90                  95

Ala Gly Val Phe Tyr Asn Arg Leu Asn Arg Asp Met Pro Leu Gln Ser
            100                 105                 110

Asn Ile Ala Ile Leu Tyr Ala Gln Gly Lys Leu Gly Gln Asn Ile Ser
        115                 120                 125

Leu Ala Glu Asp Val Ala Ile Asp Thr Asn Ile Asp Ser Pro Tyr Asn
    130                 135                 140

Val Tyr Lys Asn Val Gly Leu Met Pro Gly Val Asp Ser Pro Ser
145                 150                 155                 160

Leu Asp Ala Ile Glu Ser Ser Ile Asn Gln Thr Lys Ser Asp Asn Leu
                165                 170                 175

Tyr Phe Val Ala Asp Val Thr Glu Gly Lys Val Tyr Tyr Ala Asn Asn
            180                 185                 190

Gln Glu Asp His Asp Arg Asn
        195

<210> SEQ ID NO 2
<211> LENGTH: 551
<212> TYPE: PRT
<213> ORGANISM: Streptococcus pneumoniae

<400> SEQUENCE: 2

Met Ser Glu Lys Ser Arg Glu Glu Lys Leu Ser Phe Lys Glu Gln
 1               5                  10                  15

Ile Leu Arg Asp Leu Glu Lys Val Lys Gly Tyr Asp Glu Val Leu Lys
             20                  25                  30

Glu Asp Glu Ala Val Val Arg Thr Pro Ala Asn Glu Pro Ser Ala Glu
         35                  40                  45

Glu Leu Met Ala Asp Ser Leu Ser Thr Val Glu Ile Met Arg Lys
     50                  55                  60

Ala Pro Thr Val Pro Thr His Pro Ser Gln Gly Val Pro Ala Ser Pro
 65                  70                  75                  80

Ala Asp Glu Ile Gln Arg Glu Thr Pro Gly Val Pro Ser His Pro Ser
                 85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
```

```
             145                 150                 155                 160
Ile Arg Asp Thr Ser Arg Arg Ser Arg Glu Gly Ala Lys Pro Ala
                 165                 170                 175
Lys Pro Lys Lys Glu Lys Lys Ser His Val Lys Ala Phe Val Ile Ser
             180                 185                 190
Phe Leu Val Phe Leu Ala Leu Leu Ser Ala Gly Gly Tyr Phe Gly Tyr
             195                 200                 205
Gln Tyr Val Leu Asp Ser Leu Pro Ile Asp Ala Asn Ser Lys Lys
         210                 215                 220
Tyr Val Thr Val Gly Ile Pro Glu Gly Ser Asn Val Gln Glu Ile Gly
225                 230                 235                 240
Thr Thr Leu Glu Lys Ala Gly Leu Val Lys His Gly Leu Ile Phe Ser
                 245                 250                 255
Phe Tyr Ala Lys Tyr Lys Asn Tyr Thr Asp Leu Lys Ala Gly Tyr Tyr
             260                 265                 270
Asn Leu Gln Lys Ser Met Ser Thr Glu Asp Leu Leu Lys Glu Leu Gln
             275                 280                 285
Lys Gly Gly Thr Asp Glu Pro Gln Glu Pro Val Leu Ala Thr Leu Thr
    290                 295                 300
Ile Pro Glu Gly Tyr Thr Leu Asp Gln Ile Ala Gln Thr Val Gly Gln
305                 310                 315                 320
Leu Gln Gly Asp Phe Lys Glu Ser Leu Thr Ala Glu Ala Phe Leu Ala
                 325                 330                 335
Lys Val Gln Asp Glu Thr Phe Ile Ser Gln Ala Val Ala Lys Tyr Pro
             340                 345                 350
Thr Leu Leu Glu Ser Leu Pro Val Lys Asp Ser Gly Ala Arg Tyr Arg
             355                 360                 365
Leu Glu Gly Tyr Leu Phe Pro Ala Thr Tyr Ser Ile Lys Glu Ser Thr
         370                 375                 380
Thr Ile Glu Ser Leu Ile Asp Glu Met Leu Ala Ala Met Asp Lys Asn
385                 390                 395                 400
Leu Ser Leu Tyr Tyr Ser Thr Ile Lys Ser Lys Asn Leu Thr Val Asn
                 405                 410                 415
Glu Leu Leu Thr Ile Ala Ser Leu Val Glu Lys Glu Gly Ala Lys Thr
             420                 425                 430
Glu Asp Arg Lys Leu Ile Ala Gly Val Phe Tyr Asn Arg Leu Asn Arg
         435                 440                 445
Asp Met Pro Leu Gln Ser Asn Ile Ala Ile Leu Tyr Ala Gln Gly Lys
    450                 455                 460
Leu Gly Gln Asn Ile Ser Leu Ala Glu Asp Val Ala Ile Asp Thr Asn
465                 470                 475                 480
Ile Asp Ser Pro Tyr Asn Val Tyr Lys Asn Val Gly Leu Met Pro Gly
                 485                 490                 495
Pro Val Asp Ser Pro Ser Leu Asp Ala Ile Glu Ser Ser Ile Asn Gln
             500                 505                 510
Thr Lys Ser Asp Asn Leu Tyr Phe Val Ala Asp Val Thr Glu Gly Lys
         515                 520                 525
Val Tyr Tyr Ala Asn Asn Gln Glu Asp His Asp Arg Asn Val Ala Glu
    530                 535                 540
His Val Asn Ser Lys Leu Asn
545                 550

<210> SEQ ID NO 3
<211> LENGTH: 108
```

```
<212> TYPE: PRT
<213> ORGANISM: Streptococcus pneumoniae

<400> SEQUENCE: 3

Gly Val Lys Glu Ser Ser Asn Ile Ala Ser Tyr Glu Asp Leu Lys Gly
 1               5                  10                  15

Lys Thr Val Gly Val Lys Asn Gly Thr Ala Ser Gln Thr Phe Leu Thr
                20                  25                  30

Glu Asn Gln Ser Lys Tyr Gly Tyr Lys Ile Lys Thr Phe Ala Asp Gly
            35                  40                  45

Ser Ser Met Asp Asp Ser Leu Asn Thr Gly Ala Ile Asp Ala Val Met
        50                  55                  60

Asp Asp Glu Pro Val Leu Lys Tyr Ser Ile Ser Gln Gly Gln Lys Leu
65                  70                  75                  80

Lys Thr Pro Ile Ser Gly Thr Pro Ile Gly Glu Thr Ala Phe Ala Val
                85                  90                  95

Lys Lys Gly Ala Asn Pro Glu Leu Ile Glu Met Phe
            100                 105

<210> SEQ ID NO 4
<211> LENGTH: 721
<212> TYPE: PRT
<213> ORGANISM: Streptococcus pneumoniae

<400> SEQUENCE: 4

Met Lys Lys Lys Phe Leu Ala Phe Leu Leu Ile Leu Phe Pro Ile Phe
 1               5                  10                  15

Ser Leu Gly Ile Ala Lys Ala Glu Thr Ile Lys Ile Val Ser Asp Thr
                20                  25                  30

Ala Tyr Ala Pro Phe Glu Phe Lys Asp Ser Asp Gln Thr Tyr Lys Gly
            35                  40                  45

Ile Asp Val Asp Ile Ile Asn Lys Val Ala Glu Ile Lys Gly Trp Asn
        50                  55                  60

Ile Gln Met Ser Tyr Pro Gly Phe Asp Ala Ala Val Asn Ala Val Gln
65                  70                  75                  80

Ala Gly Gln Ala Asp Ala Ile Met Ala Gly Met Thr Lys Thr Lys Glu
                85                  90                  95

Arg Glu Lys Ser Val Phe Thr Met Ser Asp Thr Tyr Tyr Asp Thr Lys Val
            100                 105                 110

Val Ile Ala Thr Thr Lys Ser His Lys Ile Ser Lys Tyr Asp Gln Leu
        115                 120                 125

Thr Gly Lys Thr Val Gly Val Lys Asn Gly Thr Ala Ala Gln Arg Phe
130                 135                 140

Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
                165                 170                 175

Met Met Asp Asp Lys Pro Val Ile Glu Tyr Ala Ile Asn Gln Gly Gln
            180                 185                 190

Asp Leu His Ile Glu Met Asp Gly Glu Ala Val Gly Ser Phe Ala Phe
        195                 200                 205

Gly Val Lys Lys Gly Ser Lys Tyr Glu His Leu Val Thr Glu Phe Asn
    210                 215                 220

Gln Ala Leu Ser Glu Met Lys Lys Asp Gly Ser Leu Asp Lys Ile Ile
225                 230                 235                 240

Lys Lys Trp Thr Ala Ser Ser Ser Ser Ala Val Pro Thr Thr Thr Thr
```

```
            245                 250                 255
Leu Ala Gly Leu Lys Ala Ile Pro Val Lys Ala Lys Tyr Ile Ile Ala
            260                 265                 270
Ser Asp Ser Ser Phe Ala Pro Phe Val Phe Gln Asn Ser Ser Asn Gln
            275                 280                 285
Tyr Thr Gly Ile Asp Met Glu Leu Ile Lys Ala Ile Ala Lys Asp Gln
            290                 295                 300
Gly Phe Glu Ile Glu Ile Thr Asn Pro Gly Phe Asp Ala Ala Ile Ser
305                 310                 315                 320
Ala Val Gln Ala Gly Gln Ala Asp Gly Ile Ile Ala Gly Met Ser Val
            325                 330                 335
Thr Asp Ala Arg Lys Ala Thr Phe Asp Phe Ser Glu Ser Tyr Tyr Thr
            340                 345                 350
Ala Asn Thr Ile Leu Gly Val Lys Glu Ser Ser Asn Ile Ala Ser Tyr
            355                 360                 365
Glu Asp Leu Lys Gly Lys Thr Val Gly Val Lys Asn Gly Thr Ala Ser
            370                 375                 380
Gln Thr Phe Leu Thr Glu Asn Gln Ser Lys Tyr Gly Tyr Lys Ile Lys
385                 390                 395                 400
Thr Phe Ala Asp Gly Ser Ser Met Asp Asp Ser Leu Asn Thr Gly Ala
            405                 410                 415
Ile Asp Ala Val Met Asp Glu Pro Val Leu Lys Tyr Ser Ile Ser
            420                 425                 430
Gln Gly Gln Lys Leu Lys Thr Pro Ile Ser Gly Thr Pro Ile Gly Glu
            435                 440                 445
Thr Ala Phe Ala Val Lys Lys Gly Ala Asn Pro Glu Leu Ile Glu Met
            450                 455                 460
Phe Asn Asn Gly Leu Ala Asn Leu Lys Ala Asn Gly Glu Phe Gln Lys
465                 470                 475                 480
Ile Leu Asp Lys Tyr Leu Ala Ser Glu Ser Thr Ala Ser Thr Ser
            485                 490                 495
Thr Val Asp Glu Thr Thr Leu Trp Gly Leu Leu Gln Asn Asn Tyr Lys
            500                 505                 510
Gln Leu Leu Ser Gly Leu Gly Ile Thr Leu Ala Leu Ala Leu Ile Ser
            515                 520                 525
Phe Ala Ile Ala Ile Val Ile Gly Ile Ile Phe Gly Met Phe Ser Val
            530                 535                 540
Ser Pro Tyr Lys Ser Leu Arg Val Ile Ser Glu Ile Phe Val Asp Val
545                 550                 555                 560
Ile Arg Gly Ile Pro Leu Met Ile Leu Ala Ala Phe Ile Phe Trp Gly
            565                 570                 575
Ile Pro Asn Phe Ile Glu Ser Ile Thr Gly Gln Gln Ser Pro Ile Asn
            580                 585                 590
Asp Phe Val Ala Gly Thr Ile Ala Leu Ser Leu Asn Ala Ala Ala Tyr
            595                 600                 605
Ile Ala Glu Ile Val Arg Gly Gly Ile Gln Ala Val Pro Val Gly Gln
            610                 615                 620
Met Glu Ala Ser Arg Ser Leu Gly Ile Ser Tyr Gly Lys Thr Met Arg
625                 630                 635                 640
Lys Ile Ile Leu Pro Gln Val Thr Lys Leu Met Leu Pro Asn Phe Val
            645                 650                 655
Asn Gln Phe Val Ile Ala Leu Lys Asp Thr Thr Ile Val Ser Ala Ile
            660                 665                 670
```

```
Gly Leu Val Glu Leu Phe Gln Thr Gly Lys Ile Ile Ile Ala Arg Asn
        675                 680                 685

Tyr Gln Ser Phe Lys Met Tyr Ala Ile Leu Ala Ile Phe Tyr Leu Val
    690                 695                 700

Ile Ile Thr Leu Leu Thr Arg Leu Ala Lys Arg Leu Glu Lys Arg Ile
705                 710                 715                 720

Arg

<210> SEQ ID NO 5
<211> LENGTH: 161
<212> TYPE: PRT
<213> ORGANISM: Streptococcus pneumoniae

<400> SEQUENCE: 5

Glu Gln Ile Gln Asn Asp Leu Thr Lys Thr Asp Asn Lys Thr Ser Tyr
1               5                   10                  15

Thr Val Gln Tyr Gly Asp Thr Leu Ser Thr Ile Ala Glu Ala Leu Gly
            20                  25                  30

Val Asp Val Thr Val Leu Ala Asn Leu Asn Lys Ile Thr Asn Met Asp
        35                  40                  45

Leu Ile Phe Pro Glu Thr Val Leu Thr Thr Val Asn Glu Ala Glu
    50                  55                  60

Glu Val Thr Glu Val Glu Ile Gln Thr Pro Gln Ala Asp Ser Ser Glu
65                  70                  75                  80

Glu Val Thr Thr Ala Thr Ala Asp Leu Thr Thr Asn Gln Val Thr Val
                85                  90                  95

Asp Asp Gln Thr Val Gln Val Ala Asp Leu Ser Gln Pro Ile Ala Glu
            100                 105                 110

Ala Pro Lys Glu Val Ala Ser Ser Ser Glu Val Thr Lys Thr Val Ile
        115                 120                 125

Ala Ser Glu Glu Val Ala Pro Ser Thr Gly Thr Ser Val Pro Glu Glu
    130                 135                 140

Gln Thr Ala Glu Thr Ser Ser Ala Val Ala Glu Glu Ala Pro Gln Glu
145                 150                 155                 160

Thr

<210> SEQ ID NO 6
<211> LENGTH: 380
<212> TYPE: PRT
<213> ORGANISM: Streptococcus pneumoniae

<400> SEQUENCE: 6

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45

Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Val Asn Glu Ala
                85                  90                  95

Glu Glu Val Thr Glu Val Glu Ile Gln Thr Pro Gln Ala Asp Ser Ser
            100                 105                 110
```

```
Glu Glu Val Thr Thr Ala Thr Ala Asp Leu Thr Thr Asn Gln Val Thr
        115                 120                 125
Val Asp Asp Gln Thr Val Gln Val Ala Asp Leu Ser Gln Pro Ile Ala
130                 135                 140
Glu Ala Pro Lys Glu Val Ala Ser Ser Glu Val Thr Lys Thr Val
145                 150                 155                 160
Ile Ala Ser Glu Glu Val Ala Pro Ser Thr Gly Thr Ser Val Pro Glu
                165                 170                 175
Glu Gln Thr Ala Glu Thr Ser Ser Ala Val Ala Glu Glu Ala Pro Gln
            180                 185                 190
Glu Thr Thr Pro Ala Glu Lys Gln Glu Thr Gln Thr Ser Pro Gln Ala
        195                 200                 205
Ala Ser Ala Val Glu Ala Thr Thr Thr Ser Ser Glu Ala Lys Glu Val
210                 215                 220
Ala Ser Ser Asn Gly Ala Thr Ala Ala Val Ser Thr Tyr Gln Pro Glu
225                 230                 235                 240
Glu Thr Lys Ile Ile Ser Thr Thr Tyr Glu Ala Pro Ala Ala Pro Asp
                245                 250                 255
Tyr Ala Gly Leu Ala Val Ala Lys Ser Glu Asn Ala Gly Leu Gln Pro
            260                 265                 270
Gln Thr Ala Ala Phe Lys Glu Glu Ile Ala Asn Leu Phe Gly Ile Thr
        275                 280                 285
Ser Phe Ser Gly Tyr Arg Pro Gly Asp Ser Gly Asp His Gly Lys Gly
        290                 295                 300
Leu Ala Ile Asp Phe Met Val Pro Glu Arg Ser Glu Leu Gly Asp Lys
305                 310                 315                 320
Ile Ala Glu Tyr Ala Ile Gln Asn Met Ala Ser Arg Gly Ile Ser Tyr
                325                 330                 335
Ile Ile Trp Lys Gln Arg Phe Tyr Ala Pro Phe Asp Ser Lys Tyr Gly
            340                 345                 350
Pro Ala Asn Thr Trp Asn Pro Met Pro Asp Arg Gly Ser Val Thr Glu
        355                 360                 365
Asn His Tyr Asp His Val His Val Ser Met Asn Gly
        370                 375                 380

<210> SEQ ID NO 7
<211> LENGTH: 595
<212> TYPE: DNA
<213> ORGANISM: Streptococcus pneumoniae

<400> SEQUENCE: 7
tttatcagtc aagcagtagc gaaatatcct actttactgg aaagtttgcc tgtaaaagac      60
agcggtgcgc gttatcgttt ggaaggatac cttttcccag ctacatactc tatcaaggaa     120
agcacaacta ttgagagctt gattgatgag atgttagctg ctatggataa gaacctatct     180
ctttactata gtactatcaa atctaaaaac ttgactgtca atgagttgtt gaccattgct     240
tccttggtcg aaaagaagg tgccaagaca gaagatcgta agctcattgc aggtgtattc      300
tacaatcgtt tgaatcgtga tatgccactt caaagtaata ttgcaatctt gtatgcccaa     360
ggaaaactgg ggcaaaatat cagtctagct gaggatgttg cgattgatac caacattgat     420
tcaccttata tgtttataaa aatgtaggt ctcatgcctg tccagtcga tagtccaagt      480
ctggatgcga ttgagtcaag catcaatcaa actaagagcg ataacctcta ctttgtagca     540
gatgtcacag aaggcaaggt ctactatgct aacaatcaag aagaccacga ccgca          595
```

```
<210> SEQ ID NO 8
<211> LENGTH: 324
<212> TYPE: DNA
<213> ORGANISM: Streptococcus pneumoniae

<400> SEQUENCE: 8
ggtgtcaaag aatcaagtaa tattgcttct tatgaagatc taaaaggaaa gacagtcggt      60
gttaaaaacg gaactgcttc tcaaaccttc ctaacagaaa atcaaagcaa atacggctac     120
aaaatcaaaa cctttgctga tggttcttca atggatgaca gtttaaacac tggtgccatt     180
gatgccgtta tggatgatga acctgttctc aaatattcta tcagccaagg tcaaaaattg     240
aaaactccaa tctctggaac tccaatcggt gaaacagcct ttgccgttaa aaaggagca     300 aatccagaac tgattgaaat gttc                                           324

<210> SEQ ID NO 9
<211> LENGTH: 483
<212> TYPE: DNA
<213> ORGANISM: Streptococcus pneumoniae

<400> SEQUENCE: 9
gagcaaatcc aaaacgattt gactaaaacg gacaacaaaa caagttatac cgtacagtat      60
ggtgatactt tgagcaccat tgcagaagcc ttgggtgtag atgtcacagt gcttgcgaat     120
ctgaacaaaa tcactaatat ggacttgatt ttcccagaaa ctgttttgac aacgactgtc     180
aatgaagcag aagaagtaac agaagttgaa atccaaacac ctcaagcaga ctctagtgaa     240
gaagtgacaa ctgcgacagc agatttgacc actaatcaag tgaccgttga tgatcaaact     300
gttcaggttg cagacctttc tcaaccaatt gcagaagctc caaagaagt agcatcaagt     360 tcagaagtta caaagacagt gattgcttct gaagaagtgg caccatctac gggcacttct     420
gtcccagagg agcaaacggc cgaaacaagc agtgcagttg cagaagaagc tcctcaggaa     480
acg                                                                  483

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagtcaagag aagaagagaa                                                 20

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcatcaaca atcacaaatc actttaggct tagcgggttt tgct                      44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 12
agcttccaag gagctaaaga ggttctatca aggaaagcac aact                    44

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttgattgtta gcatagtaga cc                                            22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagtgatttg tgattgttga tg                                            22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acctctttag ctccttggaa g                                             21

<210> SEQ ID NO 16
<211> LENGTH: 551
<212> TYPE: PRT
<213> ORGANISM: Streptococcus pneumoniae

<400> SEQUENCE: 16
```

Met Ser Glu Lys Ser Arg Glu Glu Lys Leu Ser Phe Lys Glu Gln
1               5                   10                  15

Ile Leu Arg Asp Leu Glu Lys Val Lys Gly Tyr Asp Glu Val Leu Lys
            20                  25                  30

Glu Asp Glu Ala Val Val Arg Thr Pro Ala Asn Glu Pro Ser Ala Glu
        35                  40                  45

Glu Leu Met Ala Asp Ser Leu Ser Thr Val Glu Ile Met Arg Lys
    50                  55                  60

Ala Pro Thr Val Pro Thr His Pro Ser Gln Gly Val Pro Ala Ser Pro
65                  70                  75                  80

Ala Asp Glu Ile Gln Arg Glu Thr Pro Gly Val Pro Ser His Pro Ser
                85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Ala
            165                 170                 175

Lys Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
            195                 200                 205

Gln Tyr Val Leu Asp Ser Leu Leu Pro Ile Asp Ala Asn Ser Lys Lys
    210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Val Lys His Gly Leu Ile Phe Ser
            245                 250                 255

Phe Tyr Ala Lys Tyr Lys Asn Tyr Thr Asp Leu Lys Ala Gly Tyr Tyr
            260                 265                 270

Asn Leu Gln Lys Ser Met Ser Thr Glu Asp Leu Leu Lys Glu Leu Gln
            275                 280                 285

Lys Gly Gly Thr Asp Glu Pro Gln Glu Pro Val Leu Ala Thr Leu Thr
            290                 295                 300

Ile Pro Glu Gly Tyr Thr Leu Asp Gln Ile Ala Gln Thr Val Gly Gln
305                 310                 315                 320

Leu Gln Gly Asp Phe Lys Glu Ser Leu Thr Ala Glu Ala Phe Leu Ala
            325                 330                 335

Lys Val Gln Asp Glu Thr Phe Ile Ser Gln Ala Val Ala Lys Tyr Pro
            340                 345                 350

Thr Leu Leu Glu Ser Leu Pro Val Lys Asp Ser Gly Ala Arg Tyr Arg
            355                 360                 365

Leu Glu Gly Tyr Leu Phe Pro Ala Thr Tyr Ser Ile Lys Glu Ser Thr
            370                 375                 380

Thr Ile Glu Ser Leu Ile Asp Glu Met Leu Ala Ala Met Asp Lys Asn
385                 390                 395                 400

Leu Ser Leu Tyr Tyr Ser Thr Ile Lys Ser Lys Asn Leu Thr Val Asn
            405                 410                 415

Glu Leu Leu Thr Ile Ala Ser Leu Val Glu Lys Glu Gly Ala Lys Thr
            420                 425                 430

Glu Asp Arg Lys Leu Ile Ala Gly Val Phe Tyr Asn Arg Leu Asn Arg
            435                 440                 445

Asp Met Pro Leu Gln Ser Asn Ile Ala Ile Leu Tyr Ala Gln Gly Lys
450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
            485                 490                 495

Pro Val Asp Ser Pro Ser Leu Asp Ala Ile Glu Ser Ser Ile Asn Gln
            500                 505                 510

Thr Lys Ser Asp Asn Leu Tyr Phe Val Ala Asp Val Thr Glu Gly Lys
            515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 17
<211> LENGTH: 551
<212> TYPE: PRT

<213> ORGANISM: Streptococcus pneumoniae

<400> SEQUENCE: 17

```
Met Ser Glu Lys Ser Arg Glu Glu Lys Leu Ser Phe Lys Glu Gln
  1               5                  10                  15

Ile Leu Arg Asp Leu Glu Lys Val Lys Gly Tyr Asp Glu Val Leu Lys
             20                  25                  30

Glu Asp Glu Ala Val Val Arg Thr Pro Ala Asn Glu Pro Ser Ala Glu
         35                  40                  45

Glu Leu Met Ala Asp Ser Leu Ser Thr Val Glu Glu Ile Met Arg Lys
     50                  55                  60

Ala Pro Thr Val Pro Thr His Pro Ser Gln Gly Val Pro Ala Ser Pro
 65                  70                  75                  80

Ala Asp Glu Ile Gln Arg Glu Thr Pro Gly Val Pro Ser His Pro Ser
                 85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Ala
                165                 170                 175

Lys Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
        195                 200                 205

Gln Tyr Val Leu Asp Ser Leu Leu Pro Ile Asp Ala Asn Ser Lys Lys
    210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Val Lys His Gly Leu Ile Phe Ser
                245                 250                 255

Phe Tyr Ala Lys Tyr Lys Asn Tyr Thr Asp Leu Lys Ala Gly Tyr Tyr
            260                 265                 270

Asn Leu Gln Lys Ser Met Ser Thr Glu Asp Leu Leu Lys Glu Leu Gln
        275                 280                 285

Lys Gly Gly Thr Asp Glu Pro Gln Glu Pro Val Leu Ala Thr Leu Thr
    290                 295                 300

Ile Pro Glu Gly Tyr Thr Leu Asp Gln Ile Ala Gln Thr Val Gly Gln
305                 310                 315                 320

Leu Gln Gly Asp Phe Lys Glu Ser Leu Thr Ala Glu Ala Phe Leu Ala
                325                 330                 335

Lys Val Gln Asp Glu Thr Phe Ile Ser Gln Ala Val Ala Lys Tyr Pro
            340                 345                 350

Thr Leu Leu Glu Ser Leu Pro Val Lys Asp Ser Gly Ala Arg Tyr Arg
        355                 360                 365

Leu Glu Gly Tyr Leu Phe Pro Ala Thr Tyr Ser Ile Lys Glu Ser Thr
    370                 375                 380

Thr Ile Glu Ser Leu Ile Asp Glu Met Leu Ala Ala Met Asp Lys Asn
385                 390                 395                 400

Leu Ser Leu Tyr Tyr Ser Thr Ile Lys Ser Lys Asn Leu Thr Val Asn
```

```
                    405                 410                 415
Glu Leu Leu Thr Ile Ala Ser Leu Val Glu Lys Glu Gly Ala Lys Thr
                420                 425                 430

Glu Asp Arg Lys Leu Ile Ala Gly Val Phe Tyr Asn Arg Leu Asn Arg
            435                 440                 445

Asp Met Pro Leu Gln Ser Asn Ile Ala Ile Leu Tyr Ala Gln Gly Lys
        450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
                485                 490                 495

Pro Val Asp Ser Pro Ser Leu Asp Ala Ile Glu Ser Ile Asn Gln
            500                 505                 510

Thr Lys Ser Asp Asn Leu Tyr Phe Val Ala Asp Val Thr Glu Gly Lys
        515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 18
<211> LENGTH: 551
<212> TYPE: PRT
<213> ORGANISM: Streptococcus pneumoniae

<400> SEQUENCE: 18

Met Ser Glu Lys Ser Arg Glu Glu Lys Leu Ser Phe Lys Glu Gln
 1               5                  10                  15

Ile Leu Arg Asp Leu Glu Lys Val Lys Gly Tyr Asp Glu Val Leu Lys
                20                  25                  30

Glu Asp Glu Ala Val Val Arg Thr Pro Ala Asn Glu Pro Ser Thr Glu
            35                  40                  45

Glu Leu Met Ala Asp Ser Leu Ser Thr Val Glu Glu Ile Met Arg Lys
        50                  55                  60

Ala Pro Thr Val Pro Thr His Pro Ser Gln Gly Val Pro Ala Ser Pro
65                  70                  75                  80

Ala Asp Glu Ile Gln Arg Glu Thr Pro Gly Val Pro Ser His Pro Ser
                85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Val
                165                 170                 175

Lys Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
        195                 200                 205

Gln Tyr Val Leu Asp Ser Leu Leu Pro Ile Asp Ala Asn Ser Lys Lys
    210                 215                 220

Tyr Val Thr Val Gly Ile Pro Glu Gly Ser Asn Val Gln Glu Ile Gly
```

```
                225                 230                 235                 240
Thr Thr Leu Glu Lys Ala Gly Leu Val Lys His Gly Leu Ile Phe Ser
                245                 250                 255

Phe Tyr Ala Lys Tyr Lys Asn Tyr Thr Asp Leu Lys Ala Gly Tyr Tyr
                260                 265                 270

Asn Leu Gln Lys Ser Met Ser Thr Glu Asp Leu Leu Lys Glu Leu Gln
                275                 280                 285

Lys Gly Gly Thr Asp Glu Pro Gln Glu Pro Val Leu Ala Thr Leu Thr
            290                 295                 300

Ile Pro Glu Gly Tyr Thr Leu Asp Gln Ile Ala Gln Thr Val Gly Gln
305                 310                 315                 320

Leu Gln Gly Asp Phe Lys Glu Ser Leu Thr Ala Glu Ala Phe Leu Ala
                325                 330                 335

Lys Val Gln Asp Glu Thr Phe Ile Ser Gln Ala Val Ala Lys Tyr Pro
                340                 345                 350

Thr Leu Leu Glu Ser Leu Pro Val Lys Asp Ser Gly Ala Arg Tyr Arg
                355                 360                 365

Leu Glu Gly Tyr Leu Phe Pro Ala Thr Tyr Ser Ile Lys Glu Ser Thr
            370                 375                 380

Thr Ile Glu Ser Leu Ile Asp Glu Met Leu Ala Ala Met Asp Lys Asn
385                 390                 395                 400

Leu Ser Pro Tyr Tyr Ser Thr Ile Lys Ser Lys Asn Leu Thr Val Asn
                405                 410                 415

Glu Leu Leu Thr Ile Ala Ser Leu Val Glu Lys Glu Gly Ala Lys Thr
                420                 425                 430

Glu Asp Arg Lys Leu Ile Ala Gly Val Phe Tyr Asn Arg Leu Asn Arg
                435                 440                 445

Asp Met Pro Leu Gln Ser Asn Ile Ala Ile Leu Tyr Ala Gln Gly Lys
            450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
                485                 490                 495

Pro Val Asp Ser Pro Ser Leu Asp Ala Ile Glu Ser Ser Ile Asn Gln
                500                 505                 510

Thr Lys Ser Asp Asn Leu Tyr Phe Val Ala Asp Val Thr Glu Gly Lys
            515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 19
<211> LENGTH: 551
<212> TYPE: PRT
<213> ORGANISM: Streptococcus pneumoniae

<400> SEQUENCE: 19

Met Ser Glu Lys Ser Arg Glu Glu Lys Leu Ser Phe Lys Glu Gln
 1               5                  10                  15

Ile Leu Arg Asp Leu Glu Lys Val Lys Gly Tyr Asp Glu Val Leu Lys
                20                  25                  30

Glu Asp Glu Ala Val Val Arg Thr Pro Ala Asn Glu Pro Ser Ala Glu
            35                  40                  45

Glu Leu Met Ala Asp Ser Leu Ser Thr Val Glu Glu Ile Met Arg Lys
```

```
                50                      55                      60
Ala Pro Thr Val Pro Thr His Pro Ser Gln Gly Val Pro Ala Ser Pro
 65                      70                      75                      80

Ala Asp Glu Ile Gln Arg Glu Thr Pro Gly Val Pro Ser His Pro Ser
                         85                      90                      95

Gln Asp Val Pro Ser Pro Ala Glu Glu Ser Gly Ser Arg Pro Gly
                        100                     105                     110

Pro Gly Pro Val Arg Pro Lys Lys Leu Glu Arg Glu Tyr Asn Glu Thr
                        115                     120                     125

Pro Thr Arg Val Ala Val Ser Tyr Thr Thr Ala Glu Lys Lys Ala Glu
130                     135                     140

Gln Ala Gly Pro Glu Thr Pro Thr Pro Ala Thr Glu Thr Val Asp Ile
145                     150                     155                     160

Ile Arg Asp Thr Ser Arg Arg Ser Arg Arg Glu Gly Ala Lys Pro Val
                        165                     170                     175

Lys Pro Lys Lys Glu Lys Lys Ser His Val Lys Ala Phe Val Ile Ser
                        180                     185                     190

Phe Leu Val Phe Leu Ala Leu Leu Ser Ala Gly Gly Tyr Phe Gly Tyr
                        195                     200                     205

Gln Tyr Val Leu Asp Ser Leu Leu Pro Ile Asp Ala Asn Ser Lys Lys
                        210                     215                     220

Tyr Val Thr Val Gly Ile Pro Glu Gly Ser Asn Val Gln Glu Ile Gly
225                     230                     235                     240

Thr Thr Leu Glu Lys Ala Gly Leu Val Lys His Gly Leu Ile Phe Ser
                        245                     250                     255

Phe Tyr Ala Lys Tyr Lys Asn Tyr Thr Asp Leu Lys Ala Gly Tyr Tyr
                        260                     265                     270

Asn Leu Gln Lys Ser Met Ser Thr Glu Asp Leu Leu Lys Glu Leu Gln
                        275                     280                     285

Lys Gly Gly Thr Asp Glu Pro Gln Glu Pro Val Leu Ala Thr Leu Thr
                        290                     295                     300

Ile Pro Glu Gly Tyr Thr Leu Asp Gln Ile Ala Gln Thr Val Gly Gln
305                     310                     315                     320

Leu Gln Gly Asp Phe Lys Glu Ser Leu Thr Ala Glu Ala Phe Leu Ala
                        325                     330                     335

Lys Val Gln Asp Glu Thr Phe Ile Ser Gln Ala Val Ala Lys Tyr Pro
                        340                     345                     350

Thr Leu Leu Glu Ser Leu Pro Val Lys Asp Ser Gly Ala Arg Tyr Arg
                        355                     360                     365

Leu Glu Gly Tyr Leu Phe Pro Ala Thr Tyr Ser Ile Lys Glu Ser Thr
                        370                     375                     380

Thr Ile Glu Ser Leu Ile Asp Glu Met Leu Ala Ala Met Asp Lys Asn
385                     390                     395                     400

Leu Ser Pro Tyr Tyr Ser Thr Ile Lys Ser Lys Asn Leu Thr Val Asn
                        405                     410                     415

Glu Leu Leu Thr Ile Ala Ser Leu Val Glu Lys Glu Gly Ala Lys Thr
                        420                     425                     430

Glu Asp Arg Lys Leu Ile Ala Gly Val Phe Tyr Asn Arg Leu Asn Arg
                        435                     440                     445

Asp Met Pro Leu Gln Ser Asn Ile Ala Ile Leu Tyr Ala Gln Gly Lys
                        450                     455                     460

Leu Gly Gln Asn Ile Ser Leu Ala Glu Asp Val Ala Ile Asp Thr Asn
465                     470                     475                     480
```

Ile Asp Ser Pro Tyr Asn Val Tyr Lys Asn Val Gly Leu Met Pro Gly
            485                 490                 495

Pro Val Asp Ser Pro Ser Leu Asp Ala Ile Glu Ser Ser Ile Asn Gln
        500                 505                 510

Thr Lys Ser Asp Asn Leu Tyr Phe Val Ala Asp Val Thr Glu Gly Lys
        515                 520                 525

Val Tyr Tyr Ala Asn Asn Gln Glu Asp His Asp Arg Asn Val Ala Glu
    530                 535                 540

His Val Asn Ser Lys Leu Asn
545                 550

<210> SEQ ID NO 20
<211> LENGTH: 551
<212> TYPE: PRT
<213> ORGANISM: Streptococcus pneumoniae

<400> SEQUENCE: 20

Met Ser Glu Lys Ser Arg Glu Glu Lys Leu Ser Phe Lys Glu Gln
1               5                   10                  15

Ile Leu Arg Asp Leu Glu Lys Val Lys Gly Tyr Asp Glu Val Leu Lys
            20                  25                  30

Glu Asp Glu Ala Val Val Arg Thr Pro Ala Asn Glu Pro Ser Thr Glu
        35                  40                  45

Glu Leu Met Ala Asp Ser Leu Ser Thr Val Glu Ile Met Arg Lys
    50                  55                  60

Ala Pro Thr Val Pro Thr His Pro Ser Gln Gly Val Pro Ala Ser Pro
65                  70                  75                  80

Ala Asp Glu Ile Gln Arg Glu Thr Pro Gly Val Pro Ser His Pro Ser
            85                  90                  95

Gln Asp Val Pro Ser Ser Pro Ala Glu Glu Ser Gly Ser Arg Pro Gly
        100                 105                 110

Pro Gly Pro Val Arg Pro Lys Lys Leu Glu Arg Glu Tyr Asn Glu Thr
    115                 120                 125

Pro Thr Arg Val Ala Val Ser Tyr Thr Thr Ala Glu Lys Lys Ala Glu
130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Val
            165                 170                 175

Lys Pro Lys Lys Glu Lys Lys Ser His Val Lys Ala Phe Val Ile Ser
        180                 185                 190

Phe Leu Val Phe Leu Ala Leu Leu Ser Ala Gly Gly Tyr Phe Gly Tyr
    195                 200                 205

Gln Tyr Val Leu Asp Ser Leu Leu Pro Ile Asp Ala Asn Ser Lys Lys
210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Val Lys His Gly Leu Ile Phe Ser
            245                 250                 255

Phe Tyr Ala Lys Tyr Lys Asn Tyr Thr Asp Leu Lys Ala Gly Tyr Tyr
        260                 265                 270

Asn Leu Gln Lys Ser Met Ser Thr Glu Asp Leu Leu Lys Glu Leu Gln
    275                 280                 285

Lys Gly Gly Thr Asp Glu Pro Gln Glu Pro Val Leu Ala Thr Leu Thr
290                 295                 300

```
Ile Pro Glu Gly Tyr Thr Leu Asp Gln Ile Ala Gln Ala Val Gly Gln
305                 310                 315                 320

Leu Gln Gly Asp Phe Lys Glu Ser Leu Thr Ala Glu Ala Phe Leu Ala
            325                 330                 335

Lys Val Gln Asp Glu Thr Phe Ile Ser Gln Ala Val Ala Lys Tyr Pro
        340                 345                 350

Thr Leu Leu Glu Ser Leu Pro Val Lys Asp Ser Gly Ala Arg Tyr Arg
    355                 360                 365

Leu Glu Gly Tyr Leu Phe Pro Ala Thr Tyr Ser Ile Lys Glu Ser Thr
370                 375                 380

Thr Ile Glu Ser Leu Ile Asp Glu Met Leu Ala Ala Met Asp Lys Asn
385                 390                 395                 400

Leu Ser Pro Tyr Tyr Ser Thr Ile Lys Ser Lys Asn Leu Thr Val Asn
            405                 410                 415

Glu Leu Leu Thr Ile Ala Ser Leu Val Glu Lys Glu Gly Ala Lys Thr
        420                 425                 430

Glu Asp Arg Lys Leu Ile Ala Gly Val Phe Tyr Asn Arg Leu Asn Arg
    435                 440                 445

Asp Met Pro Leu Gln Ser Asn Ile Ala Ile Leu Tyr Ala Gln Gly Lys
450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
            485                 490                 495

Pro Val Asp Ser Pro Ser Leu Asp Ala Ile Glu Ser Ser Ile Asn Gln
        500                 505                 510

Thr Lys Ser Asp Asn Leu Tyr Phe Val Ala Asp Val Thr Glu Gly Lys
    515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 21
<211> LENGTH: 551
<212> TYPE: PRT
<213> ORGANISM: Streptococcus pneumoniae

<400> SEQUENCE: 21

Met Ser Glu Lys Ser Arg Glu Glu Lys Leu Ser Phe Lys Glu Gln
1               5                   10                  15

Ile Leu Arg Asp Leu Glu Lys Val Lys Gly Tyr Asp Glu Val Leu Lys
                20                  25                  30

Glu Asp Glu Ala Val Val Arg Thr Pro Ala Asn Glu Pro Ser Thr Glu
            35                  40                  45

Glu Leu Met Ala Asp Ser Leu Ser Thr Val Glu Ile Met Arg Lys
        50                  55                  60

Ala Pro Thr Val Pro Thr His Pro Ser Gln Gly Val Pro Ala Ser Pro
65                  70                  75                  80

Ala Asp Glu Ile Gln Arg Glu Thr Pro Gly Val Pro Ser His Pro Ser
                85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125
```

-continued

```
Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Val
                165                 170                 175

Lys Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
        195                 200                 205

Gln Tyr Val Leu Asp Ser Leu Pro Ile Asp Ala Asn Ser Lys Lys
    210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Val Lys His Gly Leu Ile Phe Ser
                245                 250                 255

Phe Tyr Ala Lys Tyr Lys Asn Tyr Thr Asp Leu Lys Ala Gly Tyr Tyr
            260                 265                 270

Asn Leu Gln Lys Ser Met Ser Thr Glu Asp Leu Leu Lys Glu Leu Gln
        275                 280                 285

Lys Gly Gly Thr Asp Glu Pro Gln Glu Pro Val Leu Ala Thr Leu Thr
    290                 295                 300

Ile Pro Glu Gly Tyr Thr Leu Asp Gln Ile Ala Gln Thr Val Gly Gln
305                 310                 315                 320

Leu Gln Gly Asp Phe Lys Glu Ser Leu Thr Ala Glu Ala Phe Leu Ala
                325                 330                 335

Lys Val Gln Asp Glu Thr Phe Ile Ser Gln Ala Val Ala Lys Tyr Pro
            340                 345                 350

Thr Leu Leu Glu Ser Leu Pro Val Lys Asp Ser Gly Ala Arg Tyr Arg
        355                 360                 365

Leu Glu Gly Tyr Leu Phe Pro Ala Thr Tyr Ser Ile Lys Glu Ser Thr
    370                 375                 380

Thr Ile Glu Ser Leu Ile Asp Glu Met Leu Ala Ala Met Asp Lys Asn
385                 390                 395                 400

Leu Ser Pro Tyr Tyr Ser Thr Ile Lys Ser Lys Asn Leu Thr Ile Asn
                405                 410                 415

Glu Leu Leu Thr Ile Ala Ser Leu Val Glu Lys Glu Gly Ala Lys Thr
            420                 425                 430

Glu Asp Arg Lys Leu Ile Ala Gly Val Phe Tyr Asn Arg Leu Asn Arg
        435                 440                 445

Asp Met Pro Leu Gln Ser Asn Ile Ala Ile Leu Tyr Ala Gln Gly Lys
    450                 455                 460

Leu Gly Gln Asn Ile Ser Leu Ala Glu Asp Val Ala Ile Asp Thr Asp
465                 470                 475                 480

Ile Asp Ser Pro Tyr Asn Val Tyr Lys Asn Val Gly Leu Met Pro Gly
                485                 490                 495

Pro Val Asp Ser Pro Ser Leu Asp Ala Ile Glu Ser Ser Ile Asn Gln
            500                 505                 510

Thr Lys Ser Asp Asn Leu Tyr Phe Val Ala Asp Val Thr Glu Gly Lys
        515                 520                 525

Val Tyr Tyr Ala Asn Asn Gln Glu Asp His Asp Arg Asn Val Ala Glu
    530                 535                 540

His Val Asn Ser Lys Leu Asn
545                 550
```

<210> SEQ ID NO 22
<211> LENGTH: 551
<212> TYPE: PRT
<213> ORGANISM: Streptococcus pneumoniae

<400> SEQUENCE: 22

| | | | | | | | | | | | | | | |
|---|---|---|---|---|---|---|---|---|---|---|---|---|---|---|
| Met | Ser | Glu | Lys | Ser | Arg | Glu | Glu | Lys | Leu | Ser | Phe | Lys | Glu | Gln |
| 1 | | | | 5 | | | | | 10 | | | | | 15 |
| Ile | Leu | Arg | Asp | Leu | Glu | Lys | Val | Lys | Gly | Tyr | Asp | Glu | Val | Leu | Lys |
| | | | 20 | | | | | 25 | | | | | 30 | | |
| Glu | Asp | Glu | Ala | Val | Val | Arg | Thr | Pro | Ala | Asn | Glu | Pro | Ser | Ala | Glu |
| | | 35 | | | | | 40 | | | | | 45 | | | |
| Glu | Leu | Met | Ala | Asp | Ser | Leu | Ser | Thr | Val | Glu | Glu | Ile | Met | Arg | Lys |
| | 50 | | | | | 55 | | | | | 60 | | | | |
| Ala | Pro | Thr | Val | Pro | Thr | His | Pro | Ser | Gln | Gly | Val | Pro | Ala | Ser | Pro |
| 65 | | | | | 70 | | | | | 75 | | | | | 80 |
| Ala | Asp | Glu | Ile | Gln | Arg | Glu | Thr | Pro | Gly | Val | Pro | Ser | His | Pro | Ser |
| | | | | 85 | | | | | 90 | | | | | 95 | |
| Gln | Asp | Val | Pro | Ser | Ser | Pro | Ala | Glu | Glu | Ser | Gly | Ser | Arg | Pro | Gly |
| | | | 100 | | | | | 105 | | | | | 110 | | |
| Pro | Gly | Pro | Val | Arg | Pro | Lys | Lys | Leu | Glu | Arg | Glu | Tyr | Asn | Glu | Thr |
| | | 115 | | | | | 120 | | | | | 125 | | | |
| Pro | Thr | Arg | Val | Ala | Val | Ser | Tyr | Thr | Thr | Ala | Glu | Lys | Lys | Ala | Glu |
| | 130 | | | | | 135 | | | | | 140 | | | | |
| Gln | Ala | Gly | Pro | Ala | Thr | Pro | Thr | Pro | Ala | Thr | Glu | Thr | Val | Asp | Ile |
| 145 | | | | | 150 | | | | | 155 | | | | | 160 |
| Ile | Ser | Asp | Thr | Ser | Arg | Arg | Ser | Arg | Arg | Glu | Gly | Ala | Lys | Pro | Val |
| | | | | 165 | | | | | 170 | | | | | 175 | |
| Lys | Pro | Lys | Lys | Glu | Lys | Lys | Ser | His | Val | Lys | Ala | Phe | Val | Ile | Ser |
| | | | 180 | | | | | 185 | | | | | 190 | | |
| Phe | Leu | Val | Phe | Leu | Ala | Leu | Leu | Ser | Ala | Gly | Gly | Tyr | Phe | Gly | Tyr |
| | | 195 | | | | | 200 | | | | | 205 | | | |
| Gln | Tyr | Val | Leu | Asp | Ser | Leu | Leu | Pro | Ile | Asp | Ala | Asn | Ser | Lys | Lys |
| | 210 | | | | | 215 | | | | | 220 | | | | |
| Tyr | Val | Thr | Val | Gly | Ile | Pro | Glu | Gly | Ser | Asn | Val | Gln | Glu | Ile | Gly |
| 225 | | | | | 230 | | | | | 235 | | | | | 240 |
| Thr | Thr | Leu | Glu | Lys | Ala | Gly | Leu | Val | Lys | His | Gly | Leu | Ile | Phe | Ser |
| | | | | 245 | | | | | 250 | | | | | 255 | |
| Phe | Tyr | Ala | Lys | Tyr | Lys | Asn | Tyr | Thr | Asp | Leu | Lys | Ala | Gly | Tyr | Tyr |
| | | | 260 | | | | | 265 | | | | | 270 | | |
| Asn | Leu | Gln | Lys | Ser | Met | Ser | Thr | Glu | Asp | Leu | Leu | Lys | Glu | Leu | Gln |
| | | 275 | | | | | 280 | | | | | 285 | | | |
| Lys | Gly | Gly | Thr | Asp | Glu | Pro | Gln | Glu | Pro | Val | Leu | Ala | Thr | Leu | Thr |
| | 290 | | | | | 295 | | | | | 300 | | | | |
| Ile | Pro | Glu | Gly | Tyr | Thr | Leu | Asp | Gln | Ile | Ala | Gln | Ala | Val | Gly | Gln |
| 305 | | | | | 310 | | | | | 315 | | | | | 320 |
| Leu | Gln | Gly | Asp | Phe | Lys | Glu | Ser | Leu | Thr | Ala | Glu | Thr | Phe | Leu | Ala |
| | | | | 325 | | | | | 330 | | | | | 335 | |
| Lys | Val | Gln | Asp | Glu | Thr | Phe | Ile | Ser | Gln | Ala | Val | Ala | Lys | Tyr | Pro |
| | | | 340 | | | | | 345 | | | | | 350 | | |
| Thr | Leu | Leu | Glu | Ser | Leu | Pro | Val | Lys | Asp | Ser | Gly | Ala | Arg | Tyr | Arg |
| | | 355 | | | | | 360 | | | | | 365 | | | |
| Leu | Glu | Gly | Tyr | Leu | Phe | Pro | Ala | Thr | Tyr | Ser | Ile | Lys | Glu | Ser | Thr |
| | 370 | | | | | 375 | | | | | 380 | | | | |

```
Thr Ile Glu Ser Leu Ile Asp Glu Met Leu Ala Ala Met Asp Lys Asn
385                 390                 395                 400

Leu Ser Pro Tyr Tyr Ser Thr Ile Lys Ser Lys Asn Leu Thr Val Asn
            405                 410                 415

Glu Leu Leu Thr Ile Ala Ser Leu Val Glu Lys Glu Gly Ala Lys Thr
        420                 425                 430

Glu Asp Arg Lys Leu Ile Ala Gly Val Phe Tyr Asn Arg Leu Asn Arg
    435                 440                 445

Asp Met Pro Leu Gln Ser Asn Ile Ala Ile Leu Tyr Ala Gln Gly Lys
    450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
            485                 490                 495

Pro Val Asp Ser Pro Ser Leu Asp Ala Ile Glu Ser Ser Ile Asn Gln
            500                 505                 510

Thr Lys Ser Asp Asn Leu Tyr Phe Val Ala Asp Val Thr Glu Gly Lys
        515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 23
<211> LENGTH: 551
<212> TYPE: PRT
<213> ORGANISM: Streptococcus pneumoniae

<400> SEQUENCE: 23

Met Ser Glu Lys Ser Arg Glu Glu Lys Leu Ser Phe Lys Glu Gln
1               5                   10                  15

Ile Leu Arg Asp Leu Glu Lys Val Lys Gly Tyr Asp Glu Val Leu Lys
            20                  25                  30

Glu Asp Glu Ala Val Val Arg Thr Pro Ala Asn Glu Pro Ser Ala Glu
        35                  40                  45

Glu Leu Met Ala Asp Ser Leu Ser Thr Val Glu Glu Ile Met Arg Lys
    50                  55                  60

Ala Pro Thr Val Ser Thr His Pro Ser Gln Gly Val Pro Ala Ser Pro
65                  70                  75                  80

Ala Asp Glu Ile Gln Arg Glu Thr Pro Gly Val Pro Ser His Pro Ser
                85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Ser Asp Thr Ser Arg Arg Ser Arg Arg Glu Gly Ala Lys Pro Val
                165                 170                 175

Asn Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
        195                 200                 205
```

```
Gln Tyr Val Leu Asp Ser Leu Leu Pro Ile Asp Ala Asn Ser Lys Lys
    210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Val Lys His Gly Leu Ile Phe Ser
                245                 250                 255

Phe Tyr Ala Lys Tyr Lys Asn Tyr Thr Asp Leu Lys Ala Gly Tyr Tyr
            260                 265                 270

Asn Leu Gln Lys Ser Met Ser Thr Glu Asp Leu Leu Lys Glu Leu Gln
        275                 280                 285

Lys Gly Gly Thr Asp Glu Pro Gln Glu Pro Val Leu Ala Thr Leu Thr
290                 295                 300

Ile Pro Glu Gly Tyr Thr Leu Asp Gln Ile Ala Gln Ala Val Gly Gln
305                 310                 315                 320

Leu Gln Gly Asp Phe Lys Glu Ser Leu Thr Ala Glu Ala Phe Leu Ala
                325                 330                 335

Lys Val Gln Asp Glu Thr Phe Ile Ser Gln Ala Val Ala Lys Tyr Pro
            340                 345                 350

Thr Leu Leu Glu Ser Leu Pro Val Lys Asp Ser Gly Ala Arg Tyr Arg
        355                 360                 365

Leu Glu Gly Tyr Leu Phe Pro Ala Thr Tyr Ser Ile Lys Glu Ser Thr
370                 375                 380

Thr Ile Glu Ser Leu Ile Asp Glu Met Leu Ala Ala Met Asp Lys Asn
385                 390                 395                 400

Leu Ser Pro Tyr Tyr Ser Thr Ile Lys Ser Lys Asn Leu Thr Val Asn
                405                 410                 415

Glu Leu Leu Thr Ile Ala Ser Leu Val Glu Lys Glu Gly Ala Lys Thr
            420                 425                 430

Glu Asp Arg Lys Leu Ile Ala Gly Val Phe Tyr Asn Arg Leu Asn Arg
        435                 440                 445

Asp Met Pro Leu Gln Ser Asn Ile Ala Ile Leu Tyr Ala Gln Gly Lys
450                 455                 460

Leu Gly Gln Asn Ile Ser Leu Ala Glu Asp Val Ala Ile Asp Thr Asn
465                 470                 475                 480

Ile Asp Ser Pro Tyr Asn Val Tyr Lys Asn Val Gly Leu Met Pro Gly
                485                 490                 495

Pro Val Asp Ser Pro Ser Leu Asp Ala Ile Glu Ser Ser Ile Asn Gln
            500                 505                 510

Thr Lys Ser Asp Asn Leu Tyr Phe Val Ala Asp Val Thr Glu Gly Lys
        515                 520                 525

Val Tyr Tyr Ala Asn Asn Gln Glu Asp His Asp Arg Asn Val Ala Glu
530                 535                 540

His Val Asn Ser Lys Leu Asn
545                 550

<210> SEQ ID NO 24
<211> LENGTH: 554
<212> TYPE: PRT
<213> ORGANISM: Streptococcus pneumoniae

<400> SEQUENCE: 24

Met Ser Glu Lys Ser Arg Glu Glu Lys Leu Ser Phe Lys Glu Gln
1               5                   10                  15

Ile Leu Arg Asp Leu Glu Lys Val Lys Gly Tyr Asp Glu Val Leu Lys
            20                  25                  30
```

```
Glu Asp Glu Ala Val Val Arg Thr Pro Ala Asn Glu Pro Ser Ala Glu
             35                  40                  45

Glu Leu Met Thr Asp Ser Leu Ser Thr Val Glu Glu Ile Met Arg Lys
         50                  55                  60

Ala Pro Thr Val Pro Thr His Pro Ser Gln Gly Val Pro Ala Ser Pro
 65                  70                  75                  80

Ala Asp Glu Ile Gln Arg Glu Thr Pro Gly Val Pro Ser His Pro Ser
                 85                  90                  95

His Pro Ser Gln Asp Val Pro Ser Ser Pro Ala Glu Glu Ser Gly Ser
            100                 105                 110

Arg Pro Gly Pro Gly Pro Val Arg Pro Lys Lys Leu Glu Arg Glu Tyr
            115                 120                 125

Asn Glu Thr Pro Thr Arg Val Ala Val Ser Tyr Thr Thr Ala Glu Lys
            130                 135                 140

Lys Ala Glu Gln Ala Gly Pro Glu Thr Pro Thr Pro Ala Thr Glu Thr
145                 150                 155                 160

Val Asp Ile Ile Ser Asp Thr Ser Arg Arg Ser Arg Arg Glu Gly Ala
                165                 170                 175

Lys Pro Val Asn Pro Lys Lys Glu Lys Lys Ser His Val Lys Ala Phe
            180                 185                 190

Val Ile Ser Phe Leu Val Phe Leu Ala Leu Leu Ser Ala Gly Gly Tyr
            195                 200                 205

Phe Gly Tyr Gln Tyr Val Leu Asp Ser Leu Leu Pro Ile Asp Ala Asn
            210                 215                 220

Ser Lys Lys Tyr Val Thr Val Gly Ile Pro Glu Gly Ser Asn Val Gln
225                 230                 235                 240

Glu Ile Gly Thr Thr Leu Glu Lys Ala Gly Leu Val Lys His Gly Leu
                245                 250                 255

Ile Phe Ser Phe Tyr Ala Lys Tyr Lys Asn Tyr Thr Asp Leu Lys Ala
            260                 265                 270

Gly Tyr Tyr Asn Leu Gln Lys Ser Met Ser Thr Glu Asp Leu Leu Lys
            275                 280                 285

Glu Leu Gln Lys Gly Gly Thr Asp Glu Pro Gln Glu Pro Val Leu Ala
            290                 295                 300

Thr Leu Thr Ile Pro Glu Gly Tyr Thr Leu Asp Gln Ile Ala Gln Ala
305                 310                 315                 320

Val Gly Gln Leu Gln Gly Asp Phe Lys Glu Ser Leu Thr Ala Glu Ala
                325                 330                 335

Phe Leu Ala Lys Val Gln Asp Glu Thr Phe Ile Ser Gln Ala Val Ala
            340                 345                 350

Lys Tyr Pro Thr Leu Leu Glu Ser Leu Pro Val Lys Asp Ser Gly Ala
            355                 360                 365

Arg Tyr Arg Leu Glu Gly Tyr Leu Phe Pro Ala Thr Tyr Ser Ile Lys
            370                 375                 380

Glu Ser Thr Thr Ile Glu Ser Leu Ile Asp Glu Met Leu Ala Ala Met
385                 390                 395                 400

Asp Lys Asn Leu Ser Pro Tyr Tyr Ser Thr Ile Lys Ser Lys Asn Leu
                405                 410                 415

Thr Val Asn Glu Leu Leu Thr Ile Ala Ser Leu Val Glu Lys Glu Gly
            420                 425                 430

Ala Lys Thr Glu Asp Arg Lys Leu Ile Ala Gly Val Phe Tyr Asn Arg
            435                 440                 445

Leu Asn Arg Asp Met Pro Leu Gln Ser Asn Ile Ala Ile Leu Tyr Ala
```

```
                 450              455              460
Gln Gly Lys Leu Gly Gln Asn Ile Ser Leu Ala Glu Asp Val Ala Ile
465                 470                 475                 480

Asp Thr Asn Ile Asp Ser Pro Tyr Asn Val Tyr Lys Asn Val Gly Leu
                485                 490                 495

Met Pro Gly Pro Val Asp Ser Pro Ser Leu Asp Ala Ile Glu Ser Ser
            500                 505                 510

Ile Asn Gln Thr Lys Ser Asp Asn Leu Tyr Phe Val Ala Asp Val Thr
            515                 520                 525

Glu Gly Lys Val Tyr Tyr Ala Asn Asn Gln Glu Asp His Asp Arg Asn
        530                 535                 540

Val Ala Glu His Val Asn Ser Lys Leu Asn
545                 550

<210> SEQ ID NO 25
<211> LENGTH: 531
<212> TYPE: PRT
<213> ORGANISM: Streptococcus pneumoniae

<400> SEQUENCE: 25

Met Ser Glu Lys Ser Arg Glu Glu Lys Leu Ser Phe Lys Glu Gln
  1               5                  10                  15

Ile Leu Arg Asp Leu Glu Lys Val Lys Gly Tyr Asp Glu Val Leu Lys
             20                  25                  30

Glu Asp Glu Ala Val Val Arg Thr Pro Ala Asn Glu Pro Ser Ala Glu
         35                  40                  45

Glu Leu Met Ala Asp Ser Leu Ser Thr Val Glu Glu Ile Met Arg Lys
     50                  55                  60

Ala Pro Thr Val Pro Thr His Pro Ser Gln Gly Val Pro Ala Ser Pro
 65                  70                  75                  80

Ala Asp Glu Ile Gln Arg Glu Thr Pro Gly Val Pro Ser His Pro Ser
                 85                  90                  95

Gln Asp Val Pro Ser Ser Pro Ala Glu Glu Ser Gly Ser Arg Pro Gly
            100                 105                 110

Pro Gly Pro Val Arg Pro Lys Lys Leu Glu Arg Glu Tyr Asn Glu Thr
        115                 120                 125

Pro Thr Arg Val Ala Val Ser Tyr Thr Thr Ala Glu Lys Lys Ala Glu
    130                 135                 140

Gln Ala Gly Pro Glu Thr Pro Thr Pro Ala Thr Glu Thr Val Asp Ile
145                 150                 155                 160

Ile Arg Asp Thr Ser Arg Arg Ser Arg Arg Glu Gly Ala Lys Pro Val
                165                 170                 175

Lys Pro Lys Lys Glu Lys Lys Ser His Val Lys Ala Phe Val Ile Ser
            180                 185                 190

Phe Leu Val Phe Leu Ala Leu Leu Ser Ala Gly Gly Tyr Phe Gly Tyr
        195                 200                 205

Gln Tyr Val Leu Asp Ser Leu Leu Pro Ile Asp Ala Asn Ser Lys Lys
    210                 215                 220

Tyr Val Thr Val Gly Ile Pro Glu Gly Ser Asn Val Gln Glu Ile Gly
225                 230                 235                 240

Thr Thr Leu Glu Lys Ala Gly Leu Ile Lys His Gly Leu Ile Phe Ser
                245                 250                 255

Phe Tyr Ala Lys Tyr Lys Asn Tyr Thr Asp Leu Lys Ala Gly Tyr Tyr
            260                 265                 270

Asn Leu Gln Lys Ser Met Ser Thr Glu Asp Leu Leu Lys Glu Leu Gln
```

```
                275                 280                 285
Lys Gly Gly Thr Asp Glu Pro Gln Glu Pro Val Leu Ala Thr Leu Thr
            290                 295                 300
Ile Pro Glu Gly Tyr Thr Leu Asp Gln Ile Ala Gln Thr Val Gly Gln
305                 310                 315                 320
Leu Gln Gly Asp Phe Lys Glu Ser Leu Thr Ala Glu Ala Phe Leu Ala
                325                 330                 335
Lys Val Gln Asp Glu Thr Phe Ile Ser Gln Ala Val Ala Lys Tyr Pro
            340                 345                 350
Thr Leu Leu Glu Ser Leu Pro Val Lys Asp Ser Gly Ala Arg Tyr Arg
                355                 360                 365
Leu Glu Gly Tyr Leu Phe Pro Ala Thr Tyr Ser Ile Lys Glu Ser Thr
            370                 375                 380
Thr Ile Glu Ser Leu Ile Asp Glu Met Leu Ala Ala Met Asp Lys Asn
385                 390                 395                 400
Leu Ser Pro Tyr Tyr Ser Thr Ile Lys Ser Lys Asn Leu Thr Val Asn
                405                 410                 415
Glu Leu Leu Thr Ile Ala Ser Leu Val Glu Lys Glu Gly Ala Lys Thr
            420                 425                 430
Glu Asp Arg Lys Leu Ile Ala Gly Val Phe Tyr Asn Arg Leu Asn Arg
                435                 440                 445
Asp Met Pro Leu Gln Ser Asn Ile Ala Ile Leu Tyr Ala Gln Gly Lys
            450                 455                 460
Leu Gly Gln Asn Ile Ser Leu Ala Glu Asp Val Ala Ile Asp Thr Asn
465                 470                 475                 480
Ile Asp Ser Pro Tyr Asn Val Tyr Lys Asn Val Gly Leu Met Pro Gly
                485                 490                 495
Pro Val Asp Ser Pro Ser Leu Asp Ala Ile Glu Ser Ser Ile Asn Gln
            500                 505                 510
Thr Lys Ser Asp Thr Leu Leu Cys Ser Arg Cys His Arg Arg Gln Gly
                515                 520                 525
Leu Leu Cys
    530

<210> SEQ ID NO 26
<211> LENGTH: 380
<212> TYPE: PRT
<213> ORGANISM: Streptococcus pneumoniae

<400> SEQUENCE: 26

Met Lys Lys Arg Met Leu Leu Ala Ser Thr Val Ala Leu Ser Phe Ala
1               5                   10                  15
Pro Val Leu Ala Thr Gln Ala Glu Glu Val Leu Trp Thr Ala Arg Ser
            20                  25                  30
Val Glu Gln Ile Gln Asn Asp Leu Thr Lys Thr Asp Asn Lys Thr Ser
        35                  40                  45
Tyr Thr Val Gln Tyr Gly Asp Thr Leu Ser Thr Ile Ala Glu Ala Leu
    50                  55                  60
Gly Val Asp Val Thr Val Leu Ala Asn Leu Asn Lys Ile Thr Asn Met
65                  70                  75                  80
Asp Leu Ile Phe Pro Glu Thr Val Leu Thr Thr Val Asn Glu Ala
                85                  90                  95
Glu Glu Val Thr Glu Val Glu Ile Gln Thr Pro Gln Ala Asp Ser Ser
            100                 105                 110
Glu Glu Val Thr Thr Ala Thr Ala Asp Leu Thr Thr Asn Gln Val Thr
```

```
                 115                 120                 125
Val Asp Asp Gln Thr Val Gln Val Ala Asp Leu Ser Gln Pro Ile Ala
130                 135                 140

Glu Ala Pro Lys Glu Val Ala Ser Ser Glu Val Thr Lys Thr Val
145                 150                 155                 160

Ile Ala Ser Glu Glu Val Ala Pro Ser Thr Gly Thr Ser Val Pro Glu
                165                 170                 175

Glu Gln Thr Ala Glu Thr Ser Ser Ala Val Ala Glu Glu Ala Pro Gln
                180                 185                 190

Glu Thr Thr Pro Ala Glu Lys Gln Glu Thr Gln Thr Ser Pro Gln Ala
                195                 200                 205

Ala Ser Ala Val Glu Ala Thr Thr Thr Ser Ser Glu Ala Lys Glu Val
    210                 215                 220

Ala Ser Ser Asn Gly Ala Thr Ala Ala Val Ser Thr Tyr Gln Pro Glu
    225                 230                 235                 240

Glu Thr Lys Ile Ile Ser Thr Thr Tyr Glu Ala Pro Ala Ala Pro Asp
                245                 250                 255

Tyr Ala Gly Leu Ala Val Ala Lys Ser Glu Asn Ala Gly Leu Gln Pro
                260                 265                 270

Gln Thr Ala Ala Phe Lys Glu Glu Ile Ala Asn Leu Phe Gly Ile Thr
    275                 280                 285

Ser Phe Ser Gly Tyr Arg Pro Gly Asp Ser Gly Asp His Gly Lys Gly
    290                 295                 300

Leu Ala Ile Asp Phe Met Val Pro Glu Arg Ser Glu Leu Gly Asp Lys
305                 310                 315                 320

Ile Ala Glu Tyr Ala Ile Gln Asn Met Ala Ser Arg Gly Ile Ser Tyr
                325                 330                 335

Ile Ile Trp Lys Gln Arg Phe Tyr Ala Pro Phe Asp Ser Lys Tyr Gly
                340                 345                 350

Pro Ala Asn Thr Trp Asn Pro Met Pro Asp Arg Gly Ser Val Thr Glu
                355                 360                 365

Asn His Tyr Asp His Val His Val Ser Met Asn Gly
    370                 375                 380

<210> SEQ ID NO 27
<211> LENGTH: 380
<212> TYPE: PRT
<213> ORGANISM: Streptococcus pneumoniae

<400> SEQUENCE: 27

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
                20                  25                  30

Val Glu Gln Ile Gln Asn Asp Leu Thr Lys Thr Asp Asn Lys Thr Ser
            35                  40                  45

Tyr Thr Val Gln Tyr Gly Asp Thr Leu Ser Thr Ile Ala Glu Ala Leu
        50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Val Asn Glu Ala
                85                  90                  95

Glu Glu Val Thr Glu Val Glu Ile Gln Thr Pro Gln Ala Asp Ser Ser
            100                 105                 110

Glu Glu Val Thr Thr Ala Thr Ala Asp Leu Thr Thr Asn Gln Val Thr
```

```
                   115                 120                 125
Val Asp Asp Gln Thr Val Gln Val Ala Asp Leu Ser Gln Pro Ile Ala
            130                 135                 140
Glu Ala Pro Lys Glu Val Ala Ser Ser Glu Val Thr Lys Thr Val
145                 150                 155                 160
Ile Ala Ser Glu Glu Val Ala Pro Ser Thr Gly Thr Ser Val Pro Glu
                165                 170                 175
Glu Gln Thr Ala Glu Thr Ser Ser Ala Val Ala Glu Glu Ala Pro Gln
            180                 185                 190
Glu Thr Thr Pro Ala Glu Lys Gln Thr Gln Thr Ser Pro Gln Ala
195                 200                 205
Ala Ser Ala Val Glu Ala Thr Thr Ser Ser Glu Ala Lys Glu Val
            210                 215                 220
Ala Ser Ser Asn Gly Ala Thr Ala Ala Val Ser Thr Tyr Gln Pro Glu
225                 230                 235                 240
Glu Thr Lys Ile Ile Ser Thr Thr Tyr Glu Ala Pro Ala Ala Pro Asp
                245                 250                 255
Tyr Ala Gly Leu Ala Val Ala Lys Ser Glu Asn Ala Gly Leu Gln Pro
            260                 265                 270
Gln Thr Ala Ala Phe Lys Glu Glu Ile Ala Asn Leu Phe Gly Ile Thr
        275                 280                 285
Ser Phe Ser Gly Tyr Arg Pro Gly Asp Ser Gly Asp His Gly Lys Gly
290                 295                 300
Leu Ala Ile Asp Phe Met Val Pro Glu Arg Ser Glu Leu Gly Asp Lys
305                 310                 315                 320
Ile Ala Glu Tyr Ala Ile Gln Asn Met Ala Ser Arg Gly Ile Ser Tyr
                325                 330                 335
Ile Ile Trp Lys Gln Arg Phe Tyr Ala Pro Phe Asp Ser Lys Tyr Gly
            340                 345                 350
Pro Ala Asn Thr Trp Asn Pro Met Pro Asp Arg Gly Ser Val Thr Glu
        355                 360                 365
Asn His Tyr Asp His Val His Val Ser Met Asn Gly
370                 375                 380

<210> SEQ ID NO 28
<211> LENGTH: 380
<212> TYPE: PRT
<213> ORGANISM: Streptococcus pneumoniae

<400> SEQUENCE: 28

Met Lys Lys Arg Met Leu Leu Ala Ser Thr Val Ala Leu Ser Phe Ala
1               5                   10                  15
Pro Val Leu Ala Thr Gln Ala Glu Glu Val Leu Trp Thr Ala Arg Ser
                20                  25                  30
Val Glu Gln Ile Gln Asn Asp Leu Thr Lys Thr Asp Asn Lys Thr Ser
            35                  40                  45
Tyr Thr Val Gln Tyr Gly Asp Thr Leu Ser Thr Ile Ala Glu Ala Leu
        50                  55                  60
Gly Val Asp Val Thr Val Leu Ala Asn Leu Asn Lys Ile Thr Asn Met
65                  70                  75                  80
Asp Leu Ile Phe Pro Glu Thr Val Leu Thr Thr Val Asn Glu Ala
                85                  90                  95
Glu Glu Val Thr Glu Val Glu Ile Gln Thr Pro Gln Ala Asp Ser Ser
            100                 105                 110
Glu Glu Val Thr Thr Ala Thr Ala Asp Leu Thr Thr Asn Gln Val Thr
```

```
               115                 120                 125
Val Asp Asp Gln Thr Val Gln Val Ala Asp Leu Ser Gln Pro Ile Ala
130                 135                 140
Glu Ala Pro Lys Glu Val Ala Ser Ser Ser Glu Val Thr Lys Thr Val
145                 150                 155                 160
Ile Ala Ser Glu Glu Val Ala Pro Ser Thr Gly Thr Ser Val Pro Glu
                165                 170                 175
Glu Gln Thr Ala Glu Thr Ser Ser Ala Val Ala Glu Glu Ala Pro Gln
            180                 185                 190
Glu Thr Thr Pro Gly Glu Lys Gln Glu Thr Gln Ala Ser Pro Gln Ala
        195                 200                 205
Ala Ser Ala Val Glu Ala Thr Thr Thr Ser Ser Glu Ala Lys Glu Val
    210                 215                 220
Ala Ser Ser Asn Gly Ala Thr Ala Ala Val Ser Thr Tyr Gln Pro Glu
225                 230                 235                 240
Glu Thr Lys Ile Ile Ser Thr Thr Tyr Glu Ala Pro Ala Ala Pro Asp
                245                 250                 255
Tyr Ala Gly Leu Ala Val Ala Lys Ser Glu Asn Ala Gly Leu Gln Pro
            260                 265                 270
Gln Thr Ala Ala Phe Lys Glu Glu Ile Ala Asn Leu Phe Gly Ile Thr
        275                 280                 285
Ser Phe Ser Gly Tyr Arg Pro Gly Asp Ser Gly Asp His Gly Lys Gly
    290                 295                 300
Leu Ala Ile Asp Phe Met Val Pro Glu Ser Ser Glu Leu Gly Asp Lys
305                 310                 315                 320
Ile Ala Glu Tyr Ala Ile Gln Asn Met Ala Ser Arg Gly Ile Ser Tyr
                325                 330                 335
Ile Ile Trp Lys Gln Arg Phe Tyr Ala Pro Phe Asp Ser Lys Tyr Gly
            340                 345                 350
Pro Ala Asn Thr Trp Asn Pro Met Pro Asp Arg Gly Ser Val Thr Glu
        355                 360                 365
Asn His Tyr Asp His Val His Val Ser Met Asn Gly
    370                 375                 380

<210> SEQ ID NO 29
<211> LENGTH: 380
<212> TYPE: PRT
<213> ORGANISM: Streptococcus pneumoniae

<400> SEQUENCE: 29

Met Lys Lys Arg Met Leu Leu Ala Ser Thr Val Ala Leu Ser Phe Ala
1               5                   10                  15
Pro Val Leu Ala Thr Gln Ala Glu Glu Val Leu Trp Thr Ala Arg Ser
            20                  25                  30
Val Glu Gln Ile Gln Asn Asp Leu Thr Lys Thr Asp Asn Lys Thr Ser
        35                  40                  45
Tyr Thr Val Gln Tyr Gly Asp Thr Leu Ser Thr Ile Ala Glu Ala Leu
    50                  55                  60
Gly Val Asp Val Thr Val Leu Ala Asn Leu Asn Lys Ile Thr Asn Met
65                  70                  75                  80
Asp Leu Ile Phe Pro Glu Thr Val Leu Thr Thr Val Asn Glu Ala
                85                  90                  95
Glu Glu Val Thr Glu Val Glu Ile Gln Thr Pro Gln Ala Asp Ser Ser
            100                 105                 110
Glu Glu Val Thr Thr Ala Thr Ala Asp Leu Thr Thr Asn Gln Val Thr
```

```
                115                 120                 125
Val Asp Asp Gln Thr Val Gln Val Ala Asp Leu Ser Gln Pro Ile Ala
130                 135                 140

Glu Ala Pro Lys Glu Val Ala Ser Ser Glu Val Thr Lys Thr Val
145                 150                 155                 160

Ile Ala Ser Glu Glu Val Ala Pro Ser Thr Gly Thr Ser Val Pro Glu
                165                 170                 175

Glu Gln Thr Thr Glu Thr Thr Arg Pro Val Glu Ala Thr Pro Gln
                180                 185                 190

Glu Thr Thr Pro Ala Glu Lys Gln Glu Thr Gln Ala Ser Pro Gln Ala
                195                 200                 205

Ala Ser Ala Val Glu Val Thr Thr Thr Ser Ser Glu Ala Lys Glu Val
            210                 215                 220

Ala Ser Ser Asn Gly Ala Thr Ala Ala Val Ser Thr Tyr Gln Pro Glu
225                 230                 235                 240

Glu Thr Lys Ile Ile Ser Thr Thr Tyr Glu Ala Pro Ala Ala Pro Asp
                245                 250                 255

Tyr Ala Gly Leu Ala Val Ala Lys Ser Glu Asn Ala Gly Leu Gln Pro
            260                 265                 270

Gln Thr Ala Ala Phe Lys Glu Glu Ile Ala Asn Leu Phe Gly Ile Thr
            275                 280                 285

Ser Phe Ser Gly Tyr Arg Pro Gly Asp Ser Gly Asp His Gly Lys Gly
290                 295                 300

Leu Ala Ile Asp Phe Met Val Pro Glu His Ser Glu Leu Gly Asp Lys
305                 310                 315                 320

Ile Ala Glu Tyr Ala Ile Gln Asn Met Ala Ser Arg Gly Ile Ser Tyr
                325                 330                 335

Ile Ile Trp Lys Gln Arg Phe Tyr Ala Pro Phe Asp Ser Lys Tyr Gly
            340                 345                 350

Pro Ala Asn Thr Trp Asn Pro Met Pro Asp Arg Gly Ser Val Thr Glu
            355                 360                 365

Asn His Tyr Asp His Val His Val Ser Met Asn Gly
        370                 375                 380

<210> SEQ ID NO 30
<211> LENGTH: 392
<212> TYPE: PRT
<213> ORGANISM: Streptococcus pneumoniae

<400> SEQUENCE: 30

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45

Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Val Asn Glu Ala
                85                  90                  95

Glu Glu Val Thr Glu Val Glu Ile Gln Thr Pro Gln Ala Asp Ser Ser
            100                 105                 110

Glu Glu Val Thr Thr Ala Thr Ala Asp Leu Thr Thr Asn Gln Val Thr
```

```
                     115                 120                 125
Val Asp Asp Gln Thr Val Gln Val Ala Asp Leu Ser Gln Pro Ile Ala
130                 135                 140

Glu Ala Pro Lys Glu Val Ala Ser Ser Glu Val Thr Lys Thr Val
145                 150                 155                 160

Ile Ala Ser Glu Glu Val Ala Pro Ser Thr Gly Thr Ser Val Pro Glu
                165                 170                 175

Glu Gln Thr Ala Glu Thr Ser Ser Ala Val Ala Glu Glu Ala Pro Gln
                180                 185                 190

Glu Thr Thr Pro Ala Glu Lys Gln Thr Gln Val Ser Ser Gln Thr
                195                 200                 205

Glu Ser Ala Val Glu Ala Thr Thr Met Pro Val Glu Glu Lys Ala Thr
210                 215                 220

Glu Thr Thr Ala Thr Ser Ser Glu Ala Lys Glu Val Ala Ser Ser Asn
225                 230                 235                 240

Gly Ala Thr Ala Ala Val Ser Thr Tyr Gln Pro Glu Glu Thr Lys Thr
                245                 250                 255

Ile Ser Thr Thr Tyr Glu Ala Pro Ala Ala Pro Asp Tyr Ala Gly Leu
                260                 265                 270

Ala Val Ala Lys Ser Glu Asn Ala Gly Leu Gln Pro Gln Thr Ala Ala
                275                 280                 285

Phe Lys Glu Glu Ile Ala Asn Leu Phe Gly Ile Thr Ser Phe Ser Gly
290                 295                 300

Tyr Arg Pro Gly Asp Ser Gly Asp His Gly Lys Gly Leu Ala Ile Asp
305                 310                 315                 320

Phe Met Val Pro Glu Ser Ser Glu Leu Gly Asp Lys Ile Ala Glu Tyr
                325                 330                 335

Ala Ile Gln Asn Met Ala Ser Arg Gly Ile Ser Tyr Ile Ile Trp Lys
                340                 345                 350

Gln Arg Phe Tyr Ala Pro Phe Asp Ser Lys Tyr Gly Pro Ala Asn Thr
                355                 360                 365

Trp Asn Pro Met Pro Asp Arg Gly Ser Val Thr Glu Asn His Tyr Asp
370                 375                 380

His Val His Val Ser Met Asn Gly
385                 390

<210> SEQ ID NO 31
<211> LENGTH: 376
<212> TYPE: PRT
<213> ORGANISM: Streptococcus pneumoniae

<400> SEQUENCE: 31

Met Leu Leu Ala Ser Thr Val Ala Leu Ser Phe Ala Pro Val Leu Ala
  1               5                  10                  15

Thr Gln Ala Glu Glu Val Leu Trp Thr Ala Arg Ser Val Glu Gln Ile
                 20                  25                  30

Gln Asn Asp Leu Thr Lys Thr Asp Asn Lys Thr Ser Tyr Thr Val Gln
                 35                  40                  45

Tyr Gly Asp Thr Leu Ser Thr Ile Ala Glu Ala Leu Gly Val Asp Val
             50                  55                  60

Thr Val Leu Ala Asn Leu Asn Lys Ile Thr Asn Met Asp Leu Ile Phe
 65                  70                  75                  80

Pro Glu Thr Val Leu Thr Thr Val Asn Glu Ala Glu Glu Val Thr
                 85                  90                  95

Glu Val Glu Ile Gln Thr Pro Gln Ala Asp Ser Ser Glu Glu Val Thr
```

```
                    100                 105                 110
Thr Ala Thr Ala Asp Leu Thr Thr Asn Gln Val Thr Val Asp Asp Gln
                115                 120                 125
Thr Val Gln Val Ala Asp Leu Ser Gln Pro Ile Ala Glu Ala Pro Lys
            130                 135                 140
Glu Val Ala Ser Ser Glu Val Thr Lys Thr Val Ile Ala Ser Glu
145                 150                 155                 160
Glu Val Ala Pro Ser Thr Gly Thr Ser Val Pro Glu Glu Gln Thr Ala
                165                 170                 175
Glu Thr Thr Arg Pro Val Glu Glu Ala Thr Pro Gln Glu Thr Thr Pro
            180                 185                 190
Ala Glu Lys Gln Glu Thr Gln Ala Ser Pro Gln Ala Ala Leu Ala Val
                195                 200                 205
Glu Ala Thr Thr Thr Ser Ser Glu Ala Lys Glu Val Ala Ser Ser Asn
            210                 215                 220
Gly Ala Thr Ala Val Ser Thr Tyr Gln Ser Glu Glu Thr Lys Val
225                 230                 235                 240
Ile Ser Thr Thr Tyr Glu Ala Pro Ala Ala Pro Asp Tyr Ala Gly Leu
                245                 250                 255
Ala Val Ala Lys Ser Glu Asn Ala Gly Leu Gln Pro Gln Thr Ala Ala
            260                 265                 270
Phe Lys Glu Glu Ile Ala Asn Leu Phe Gly Ile Thr Ser Phe Ser Gly
                275                 280                 285
Tyr Arg Pro Gly Asp Ser Gly Asp His Gly Lys Gly Leu Ala Ile Asp
            290                 295                 300
Phe Met Val Pro Glu Arg Ser Glu Leu Gly Asp Lys Ile Ala Glu Tyr
305                 310                 315                 320
Ala Ile Gln Asn Met Ala Ser Arg Gly Ile Ser Tyr Ile Ile Trp Lys
                325                 330                 335
Gln Arg Phe Tyr Ala Pro Phe Asp Ser Lys Tyr Gly Pro Ala Asn Thr
            340                 345                 350
Trp Asn Pro Met Pro Asp Arg Gly Ser Val Thr Glu Asn His Tyr Asp
                355                 360                 365
His Val His Val Ser Met Asn Gly
            370                 375

<210> SEQ ID NO 32
<211> LENGTH: 370
<212> TYPE: PRT
<213> ORGANISM: Streptococcus pneumoniae

<400> SEQUENCE: 32

Met Lys Lys Arg Met Leu Leu Ala Ser Thr Val Ala Leu Ser Phe Ala
 1               5                  10                  15
Pro Val Leu Ala Thr Gln Ala Glu Glu Val Leu Trp Thr Ala Arg Ser
                20                  25                  30
Val Glu Gln Ile Gln Asn Asp Leu Thr Lys Thr Asp Asn Lys Thr Ser
            35                  40                  45
Tyr Thr Val Gln Tyr Gly Asp Thr Leu Ser Thr Ile Ala Glu Ala Leu
        50                  55                  60
Gly Val Asp Val Thr Val Leu Ala Asn Leu Asn Lys Ile Thr Asn Met
65                  70                  75                  80
Asp Leu Ile Phe Pro Glu Thr Val Leu Thr Thr Val Asn Glu Ala
                85                  90                  95
Glu Glu Val Thr Glu Val Glu Ile Gln Thr Pro Gln Ala Asp Ser Ser
```

```
                    100                 105                 110
Glu Glu Val Thr Thr Ala Thr Ala Asp Leu Thr Thr Asn Gln Val Thr
            115                 120                 125

Val Asp Asp Gln Thr Val Gln Val Ala Asp Leu Ser Gln Pro Ile Ala
        130                 135                 140

Glu Val Thr Lys Thr Val Ile Ala Ser Glu Glu Val Ala Pro Ser Thr
145                 150                 155                 160

Gly Thr Ser Val Pro Glu Glu Gln Thr Thr Glu Thr Arg Pro Val
            165                 170                 175

Glu Glu Ala Thr Pro Gln Glu Thr Thr Pro Ala Glu Lys Gln Glu Thr
            180                 185                 190

Gln Ala Ser Pro Gln Ala Ala Ser Ala Val Glu Val Thr Thr Thr Ser
            195                 200                 205

Ser Glu Ala Lys Glu Val Ala Ser Ser Asn Gly Ala Thr Ala Ala Val
            210                 215                 220

Ser Thr Tyr Gln Pro Glu Glu Thr Lys Ile Ile Ser Thr Thr Tyr Glu
225                 230                 235                 240

Ala Pro Ala Ala Pro Asp Tyr Ala Gly Leu Ala Val Ala Lys Ser Glu
                245                 250                 255

Asn Ala Gly Leu Gln Pro Gln Thr Ala Ala Phe Lys Glu Glu Ile Ala
            260                 265                 270

Asn Leu Phe Gly Ile Thr Ser Phe Ser Gly Tyr Arg Pro Gly Asp Ser
            275                 280                 285

Gly Asp His Gly Lys Gly Leu Ala Ile Asp Phe Met Val Pro Glu Arg
        290                 295                 300

Ser Glu Leu Gly Asp Lys Ile Ala Glu Tyr Ala Ile Gln Asn Met Ala
305                 310                 315                 320

Ser Arg Gly Ile Ser Tyr Ile Trp Lys Gln Arg Phe Tyr Ala Pro
            325                 330                 335

Phe Asp Ser Lys Tyr Gly Pro Ala Asn Thr Trp Asn Pro Met Pro Asp
            340                 345                 350

Arg Gly Ser Val Thr Glu Asn His Tyr Asp His Val His Val Ser Met
            355                 360                 365

Asn Gly
    370

<210> SEQ ID NO 33
<211> LENGTH: 370
<212> TYPE: PRT
<213> ORGANISM: Streptococcus pneumoniae

<400> SEQUENCE: 33

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45

Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Thr Val Asn Glu Ala
                85                  90                  95

Glu Glu Val Thr Glu Val Glu Ile Gln Thr Pro Gln Ala Asp Ser Ser
```

```
                100             105             110
Glu Glu Val Thr Thr Ala Thr Ala Asp Leu Thr Thr Asn Gln Val Thr
            115                 120                 125
Val Asp Asp Gln Thr Val Gln Val Ala Asp Leu Ser Gln Pro Ile Ala
        130                 135                 140
Glu Val Thr Lys Thr Val Ile Ala Ser Glu Glu Val Ala Pro Ser Thr
145                 150                 155                 160
Gly Thr Ser Val Pro Glu Glu Gln Thr Thr Glu Thr Thr Arg Pro Val
                165                 170                 175
Glu Glu Ala Thr Pro Gln Glu Thr Thr Pro Ala Glu Lys Gln Glu Thr
            180                 185                 190
Gln Ala Ser Pro Gln Ala Ala Ser Ala Val Glu Val Thr Thr Thr Ser
        195                 200                 205
Ser Glu Ala Lys Glu Val Ala Ser Ser Asn Gly Ala Thr Ala Ala Val
        210                 215                 220
Ser Thr Tyr Gln Pro Glu Glu Thr Lys Ile Ile Ser Thr Thr Tyr Glu
225                 230                 235                 240
Ala Pro Ala Ala Pro Asp Tyr Ala Gly Leu Ala Val Ala Lys Ser Glu
                245                 250                 255
Asn Ala Gly Leu Gln Pro Gln Thr Ala Ala Phe Lys Glu Glu Ile Ala
            260                 265                 270
Asn Leu Phe Gly Ile Thr Ser Phe Ser Gly Tyr Arg Pro Gly Asp Ser
        275                 280                 285
Gly Asp His Gly Lys Gly Leu Ala Ile Asp Phe Met Val Pro Glu Arg
        290                 295                 300
Ser Glu Leu Gly Asp Lys Ile Ala Glu Tyr Ala Ile Gln Asn Met Ala
305                 310                 315                 320
Ser Arg Gly Ile Ser Tyr Ile Ile Trp Lys Gln Arg Phe Tyr Ala Pro
                325                 330                 335
Phe Asp Ser Lys Tyr Gly Pro Ala Asn Thr Trp Asn Pro Met Pro Asp
            340                 345                 350
Arg Gly Ser Val Thr Glu Asn His Tyr Asp His Val His Val Ser Met
        355                 360                 365
Asn Gly
    370

<210> SEQ ID NO 34
<211> LENGTH: 370
<212> TYPE: PRT
<213> ORGANISM: Streptococcus pneumoniae

<400> SEQUENCE: 34

Met Lys Lys Arg Met Leu Leu Ala Ser Thr Val Ala Leu Ser Phe Ala
1               5                   10                  15
Pro Val Leu Ala Thr Gln Ala Glu Glu Val Leu Trp Thr Ala Arg Ser
            20                  25                  30
Val Glu Gln Ile Gln Asn Asp Leu Thr Lys Thr Asp Asn Lys Thr Ser
        35                  40                  45
Tyr Thr Val Gln Tyr Gly Asp Thr Leu Ser Thr Ile Ala Glu Ala Leu
    50                  55                  60
Gly Val Asp Val Thr Val Leu Ala Asn Leu Asn Lys Ile Thr Asn Met
65                  70                  75                  80
Asp Leu Ile Phe Pro Glu Thr Val Leu Thr Thr Thr Val Asn Glu Ala
                85                  90                  95
Glu Glu Val Thr Glu Val Glu Ile Gln Thr Pro Gln Ala Asp Ser Ser
```

```
                  100                 105                 110
Glu Glu Val Thr Thr Ala Thr Ala Asp Leu Thr Thr Asn Gln Val Thr
            115                 120                 125

Val Asp Asp Gln Thr Val Gln Val Ala Asp Leu Ser Gln Pro Ile Ala
        130                 135                 140

Glu Val Thr Lys Thr Val Ile Ala Ser Glu Glu Val Ala Pro Ser Thr
145                 150                 155                 160

Gly Thr Ser Val Pro Glu Glu Gln Thr Thr Glu Thr Thr Arg Pro Val
                165                 170                 175

Glu Glu Ala Thr Pro Gln Glu Thr Thr Pro Ala Glu Lys Gln Glu Thr
            180                 185                 190

Gln Ala Ser Pro Gln Ala Ala Ser Ala Val Glu Val Thr Thr Thr Ser
        195                 200                 205

Ser Glu Ala Lys Glu Val Ala Ser Ser Asn Gly Ala Thr Ala Ala Val
210                 215                 220

Ser Thr Tyr Gln Pro Glu Glu Thr Lys Val Ile Ser Thr Thr Tyr Glu
225                 230                 235                 240

Ala Pro Ala Ala Pro Asp Tyr Ala Gly Leu Ala Val Ala Lys Ser Glu
                245                 250                 255

Asn Ala Gly Leu Gln Pro Gln Thr Ala Ala Phe Lys Glu Glu Ile Ala
            260                 265                 270

Asn Leu Phe Gly Ile Thr Ser Phe Ser Gly Tyr Arg Pro Gly Asp Ser
        275                 280                 285

Gly Asp His Gly Lys Gly Leu Ala Ile Asp Phe Met Val Pro Glu Arg
        290                 295                 300

Ser Glu Leu Gly Asp Lys Ile Ala Glu Tyr Ala Ile Gln Asn Met Ala
305                 310                 315                 320

Ser Arg Gly Ile Ser Tyr Ile Ile Trp Lys Gln Arg Phe Tyr Ala Pro
                325                 330                 335

Phe Asp Ser Lys Tyr Gly Pro Ala Asn Thr Trp Asn Pro Met Pro Asp
            340                 345                 350

Arg Gly Ser Val Thr Glu Asn His Tyr Asp His Val His Val Ser Met
        355                 360                 365

Asn Gly
    370

<210> SEQ ID NO 35
<211> LENGTH: 380
<212> TYPE: PRT
<213> ORGANISM: Streptococcus pneumoniae

<400> SEQUENCE: 35

Met Lys Lys Arg Met Leu Leu Ala Ser Thr Val Ala Leu Ser Phe Ala
 1               5                  10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45

Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Val Asn Glu Ala
                85                  90                  95

Glu Glu Val Thr Glu Val Glu Ile Gln Thr Pro Gln Ala Asp Ser Ser
```

```
                  100                 105                 110
Glu Glu Val Thr Thr Ala Thr Ala Asp Leu Thr Thr Asn Gln Val Thr
            115                 120                 125

Val Asp Val Gln Thr Val Gln Val Ala Asp Leu Ser Gln Pro Ile Ala
        130                 135                 140

Glu Ala Pro Lys Glu Val Ala Ser Ser Ser Glu Val Thr Lys Thr Val
145                 150                 155                 160

Ile Ala Ser Glu Glu Val Ala Pro Ser Thr Gly Thr Ser Val Pro Glu
                165                 170                 175

Glu Gln Thr Ala Glu Thr Thr Arg Pro Val Glu Glu Ala Thr Pro Gln
            180                 185                 190

Glu Thr Thr Pro Ala Lys Lys Gln Glu Thr Gln Ala Ser Pro Gln Ala
        195                 200                 205

Ala Ser Ala Val Glu Ala Thr Thr Ser Ser Glu Ala Lys Glu Val
        210                 215                 220

Ala Ser Ser Asn Gly Ala Thr Ala Ala Val Ser Thr Tyr Gln Pro Glu
225                 230                 235                 240

Glu Thr Lys Val Ile Ser Thr Thr Tyr Glu Ala Pro Ala Ala Pro Asp
                245                 250                 255

Tyr Ala Gly Leu Ala Val Ala Lys Ser Glu Asn Ala Gly Leu Gln Pro
            260                 265                 270

Gln Thr Ala Ala Phe Lys Glu Ile Ala Asn Leu Phe Gly Ile Thr
        275                 280                 285

Ser Phe Ser Gly Tyr Arg Pro Gly Asp Ser Gly Asp His Gly Lys Gly
        290                 295                 300

Leu Ala Ile Asp Phe Met Val Ala Glu Arg Ser Glu Leu Gly Asp Lys
305                 310                 315                 320

Ile Ala Glu Tyr Ala Ile Gln Asn Met Ala Ser Arg Gly Ile Ser Tyr
                325                 330                 335

Ile Ile Trp Lys Gln Arg Phe Tyr Ala Pro Phe Asp Ser Lys Tyr Gly
            340                 345                 350

Pro Ala Asn Thr Trp Asn Pro Met Pro Asp Arg Gly Ser Val Thr Glu
        355                 360                 365

Asn His Tyr Asp His Val His Val Ser Met Asn Gly
        370                 375                 380

<210> SEQ ID NO 36
<211> LENGTH: 388
<212> TYPE: PRT
<213> ORGANISM: Streptococcus pneumoniae

<400> SEQUENCE: 36

Met Leu Leu Ala Ser Thr Val Ala Leu Ser Phe Ala Pro Val Leu Ala
  1               5                  10                  15

Thr Gln Ala Glu Glu Val Leu Trp Thr Ala Arg Ser Val Glu Gln Ile
             20                  25                  30

Gln Asn Asp Leu Thr Lys Thr Asp Asn Lys Thr Ser Tyr Thr Val Gln
         35                  40                  45

Tyr Gly Asp Thr Leu Ser Thr Ile Ala Glu Ala Leu Asp Val Asp Val
     50                  55                  60

Thr Val Leu Ala Asn Leu Asn Lys Ile Thr Asn Met Asp Leu Ile Phe
 65                  70                  75                  80

Pro Glu Thr Val Leu Thr Thr Val Asn Glu Ala Glu Glu Val Thr
                 85                  90                  95

Glu Val Glu Ile Gln Thr Pro Gln Ala Asp Ser Ser Glu Glu Val Thr
```

```
            100                 105                 110
Thr Ala Thr Ala Asp Leu Thr Thr Asn Gln Val Thr Val Asp Asp Gln
        115                 120                 125

Thr Val Gln Val Ala Asp Leu Ser Gln Pro Ile Ala Glu Ala Pro Lys
        130                 135             140

Glu Val Ala Ser Asn Ser Glu Val Ala Glu Thr Val Thr Ala Ala Glu
145                 150                 155                 160

Glu Val Ala Leu Ser Thr Asp Ser Thr Thr Pro Glu Gly Gln Pro Ala
            165                 170                 175

Glu Thr Thr Ser Pro Val Glu Glu Val Ala Pro Gln Ala Thr Thr Leu
        180                 185                 190

Ala Glu Lys Gln Glu Thr Gln Val Ser Ser Gln Thr Glu Ser Ala Val
        195                 200                 205

Glu Ala Thr Thr Met Pro Val Glu Glu Lys Ala Thr Glu Thr Thr Ala
        210                 215                 220

Thr Ser Ser Glu Ala Lys Glu Val Ala Ser Ser Asn Gly Ala Thr Ala
225                 230                 235                 240

Ala Val Ser Thr Tyr Gln Pro Glu Glu Thr Lys Thr Ile Ser Thr Thr
            245                 250                 255

Tyr Glu Ala Pro Ala Ala Pro Asp Tyr Ala Gly Leu Ala Val Ala Lys
        260                 265                 270

Ser Glu Asn Ala Gly Leu Gln Pro Gln Thr Ala Ala Phe Lys Glu Glu
        275                 280                 285

Ile Ala Asn Leu Phe Gly Ile Thr Ser Phe Ser Gly Tyr Arg Pro Gly
        290                 295                 300

Asp Ser Gly Asp His Gly Lys Gly Leu Ala Ile Asp Phe Met Val Pro
305                 310                 315                 320

Glu Ser Ser Glu Leu Gly Asp Lys Ile Ala Glu Tyr Ala Ile Gln Asn
            325                 330                 335

Met Ala Ser Arg Gly Ile Ser Tyr Ile Ile Trp Lys Gln Arg Phe Tyr
        340                 345                 350

Ala Pro Phe Asp Ser Lys Tyr Gly Pro Ala Asn Thr Trp Asn Pro Met
        355                 360                 365

Pro Asp Arg Gly Ser Val Thr Glu Asn His Tyr Asp His Val His Val
370                 375                 380

Ser Met Asn Gly
385

<210> SEQ ID NO 37
<211> LENGTH: 721
<212> TYPE: PRT
<213> ORGANISM: Streptococcus pneumoniae

<400> SEQUENCE: 37

Met Lys Lys Lys Phe Leu Ala Phe Leu Leu Ile Leu Phe Pro Ile Phe
1               5                   10                  15

Ser Leu Gly Ile Ala Lys Ala Glu Thr Ile Lys Ile Val Ser Asp Thr
            20                  25                  30

Ala Tyr Ala Pro Phe Glu Phe Lys Asp Ser Asp Gln Thr Tyr Lys Gly
        35                  40                  45

Ile Asp Val Asp Ile Ile Asn Lys Val Ala Glu Ile Lys Gly Trp Asn
    50                  55                  60

Ile Gln Met Ser Tyr Pro Gly Phe Asp Ala Ala Val Asn Ala Val Gln
65                  70                  75                  80

Ala Gly Gln Ala Asp Ala Ile Met Ala Gly Met Thr Lys Thr Lys Glu
```

-continued

```
                85                  90                  95
Arg Glu Lys Val Phe Thr Met Ser Asp Thr Tyr Tyr Asp Thr Lys Val
                100                 105                 110
Val Ile Ala Thr Thr Lys Ser His Lys Ile Ser Lys Tyr Asp Gln Leu
                115                 120                 125
Thr Gly Lys Thr Val Gly Val Lys Asn Gly Thr Ala Ala Gln Arg Phe
                130                 135                 140
Leu Glu Thr Ile Lys Asp Lys Tyr Gly Phe Thr Ile Lys Thr Phe Asp
145                 150                 155                 160
Thr Gly Asp Leu Met Asn Asn Ser Leu Ser Ala Gly Ala Ile Asp Ala
                165                 170                 175
Met Met Asp Asp Lys Pro Val Ile Glu Tyr Ala Ile Asn Gln Gly Gln
                180                 185                 190
Asp Leu His Ile Glu Met Asp Gly Glu Ala Val Gly Ser Phe Ala Phe
                195                 200                 205
Gly Val Lys Lys Gly Ser Lys Tyr Glu His Leu Val Thr Glu Phe Asn
                210                 215                 220
Gln Ala Leu Ser Glu Met Lys Lys Asp Gly Ser Leu Asp Lys Ile Ile
225                 230                 235                 240
Lys Lys Trp Thr Ala Ser Ser Ser Ala Val Pro Thr Thr Thr Thr
                245                 250                 255
Leu Ala Gly Leu Lys Ala Ile Pro Val Lys Ala Lys Tyr Ile Ile Ala
                260                 265                 270
Ser Asp Ser Ser Phe Ala Pro Phe Val Phe Gln Asn Ser Ser Asn Gln
                275                 280                 285
Tyr Thr Gly Ile Asp Met Glu Leu Ile Lys Ala Ile Ala Lys Asp Gln
                290                 295                 300
Gly Phe Glu Ile Glu Ile Thr Asn Pro Gly Phe Asp Ala Ala Ile Ser
305                 310                 315                 320
Ala Val Gln Ala Gly Gln Ala Asp Gly Ile Ile Ala Gly Met Ser Val
                325                 330                 335
Thr Asp Ala Arg Lys Ala Thr Phe Asp Phe Ser Glu Ser Tyr Tyr Thr
                340                 345                 350
Ala Asn Thr Ile Leu Gly Val Lys Glu Ser Ser Asn Ile Ala Ser Tyr
                355                 360                 365
Glu Asp Leu Lys Gly Lys Thr Val Gly Val Lys Asn Gly Thr Ala Ser
                370                 375                 380
Gln Thr Phe Leu Thr Glu Asn Gln Ser Lys Tyr Gly Tyr Lys Ile Lys
385                 390                 395                 400
Thr Phe Ala Asp Gly Ser Ser Met Asp Ser Leu Asn Thr Gly Ala
                405                 410                 415
Ile Asp Ala Val Met Asp Asp Glu Pro Val Leu Lys Tyr Ser Ile Ser
                420                 425                 430
Gln Gly Gln Lys Leu Lys Thr Pro Ile Ser Gly Thr Pro Ile Gly Glu
                435                 440                 445
Thr Ala Phe Ala Val Lys Lys Gly Ala Asn Pro Glu Leu Ile Glu Met
                450                 455                 460
Phe Asn Asn Gly Leu Ala Asn Leu Lys Ala Asn Gly Glu Phe Gln Lys
465                 470                 475                 480
Ile Leu Asp Lys Tyr Leu Ala Ser Glu Ser Thr Ala Ser Thr Ser
                485                 490                 495
Thr Val Asp Glu Thr Thr Leu Trp Gly Leu Leu Gln Asn Asn Tyr Lys
                500                 505                 510
```

```
Gln Leu Leu Ser Gly Leu Gly Ile Thr Leu Ala Leu Ala Leu Ile Ser
        515                 520                 525

Phe Ala Ile Ala Ile Val Ile Gly Ile Ile Phe Gly Met Phe Ser Val
        530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
                565                 570                 575

Ile Pro Asn Phe Ile Glu Ser Ile Thr Gly Gln Gln Ser Pro Ile Asn
                580                 585                 590

Asp Phe Val Ala Gly Thr Ile Ala Leu Ser Leu Asn Ala Ala Ala Tyr
                595                 600                 605

Ile Ala Glu Ile Val Arg Gly Gly Ile Gln Ala Val Pro Val Gly Gln
                610                 615                 620

Met Glu Ala Ser Arg Ser Leu Gly Ile Ser Tyr Gly Lys Thr Met Arg
625                 630                 635                 640

Lys Ile Ile Leu Pro Gln Val Thr Lys Leu Met Leu Pro Asn Phe Val
                645                 650                 655

Asn Gln Phe Val Ile Ala Leu Lys Asp Thr Thr Ile Val Ser Ala Ile
                660                 665                 670

Gly Leu Val Glu Leu Phe Gln Thr Gly Lys Ile Ile Ile Ala Arg Asn
                675                 680                 685

Tyr Gln Ser Phe Lys Met Tyr Ala Ile Leu Ala Ile Phe Tyr Leu Val
                690                 695                 700

Ile Ile Thr Leu Leu Thr Arg Leu Ala Lys Arg Leu Glu Lys Arg Ile
705                 710                 715                 720

Arg

<210> SEQ ID NO 38
<211> LENGTH: 721
<212> TYPE: PRT
<213> ORGANISM: Streptococcus pneumoniae

<400> SEQUENCE: 38

Met Lys Lys Lys Phe Leu Ala Phe Leu Leu Ile Leu Phe Pro Ile Phe
  1                 5                  10                 15

Ser Leu Gly Ile Ala Lys Ala Glu Thr Ile Lys Ile Val Ser Asp Thr
                20                 25                  30

Ala Tyr Ala Pro Phe Glu Phe Lys Asp Ser Asp Gln Thr Tyr Lys Gly
            35                  40                  45

Ile Asp Val Asp Ile Ile Asn Lys Val Ala Glu Ile Lys Gly Trp Asn
 50                  55                  60

Ile Gln Met Ser Tyr Pro Gly Phe Asp Ala Ala Val Asn Ala Val Gln
 65                  70                  75                  80

Ala Gly Gln Ala Asp Ala Ile Met Ala Gly Met Thr Lys Thr Lys Glu
                85                  90                  95

Arg Glu Lys Val Phe Thr Met Ser Asp Thr Tyr Tyr Asp Thr Lys Val
                100                 105                 110

Val Ile Ala Thr Thr Lys Ser His Lys Ile Ser Lys Tyr Asp Gln Leu
            115                 120                 125

Thr Gly Lys Thr Val Gly Val Lys Asn Gly Thr Ala Ala Gln Arg Phe
        130                 135                 140

Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
```

-continued

```
                165                 170                 175
Met Met Asp Asp Lys Pro Val Ile Glu Tyr Ala Ile Asn Gln Gly Gln
            180                 185                 190

Asp Leu His Ile Glu Met Asp Gly Glu Ala Val Gly Ser Phe Ala Phe
        195                 200                 205

Gly Val Lys Lys Gly Ser Lys Tyr Glu His Leu Val Thr Glu Phe Asn
    210                 215                 220

Gln Ala Leu Ser Glu Met Lys Lys Asp Gly Ser Leu Asp Lys Ile Ile
225                 230                 235                 240

Lys Lys Trp Thr Ala Ser Ser Ser Ala Val Pro Thr Thr Thr
                245                 250                 255

Leu Ala Gly Leu Lys Ala Ile Pro Val Lys Ala Lys Tyr Ile Ile Ala
            260                 265                 270

Ser Asp Ser Ser Phe Ala Pro Phe Val Phe Gln Asn Ser Ser Asn Gln
        275                 280                 285

Tyr Thr Gly Ile Asp Met Glu Leu Ile Lys Ala Ile Ala Lys Asp Gln
    290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
                325                 330                 335

Thr Asp Ala Arg Lys Ala Thr Phe Asp Phe Ser Glu Ser Tyr Tyr Thr
            340                 345                 350

Ala Asn Thr Ile Leu Gly Val Lys Glu Ser Ser Asn Ile Ala Ser Tyr
        355                 360                 365

Glu Asp Leu Lys Gly Lys Thr Val Gly Val Lys Asn Gly Thr Ala Ser
    370                 375                 380

Gln Thr Phe Leu Thr Glu Asn Gln Ser Lys Tyr Gly Tyr Lys Ile Lys
385                 390                 395                 400

Thr Phe Ala Asp Gly Ser Ser Met Asp Asp Ser Leu Asn Thr Gly Ala
                405                 410                 415

Ile Asp Ala Val Met Asp Asp Glu Pro Val Leu Lys Tyr Ser Ile Ser
            420                 425                 430

Gln Gly Gln Lys Leu Lys Thr Pro Ile Ser Gly Thr Pro Ile Gly Glu
        435                 440                 445

Thr Ala Phe Ala Val Lys Lys Gly Ala Asn Pro Glu Leu Ile Glu Met
    450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Thr Ala Ser Thr Ser
                485                 490                 495

Thr Val Asp Glu Thr Thr Leu Trp Gly Leu Leu Gln Asn Asn Tyr Lys
            500                 505                 510

Gln Leu Leu Ser Gly Leu Gly Ile Thr Leu Ala Leu Ala Leu Ile Ser
        515                 520                 525

Phe Ala Ile Ala Ile Val Ile Gly Ile Ile Phe Gly Met Phe Ser Val
    530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
                565                 570                 575

Ile Pro Asn Phe Ile Glu Ser Ile Thr Gly Gln Gln Ser Pro Ile Asn
            580                 585                 590
```

```
Asp Phe Val Ala Gly Thr Ile Ala Leu Ser Leu Asn Ala Ala Ala Tyr
            595                 600                 605

Ile Ala Glu Ile Val Arg Gly Ile Gln Ala Val Pro Val Gly Gln
    610                 615                 620

Met Glu Ala Ser Arg Ser Leu Gly Ile Ser Tyr Gly Lys Thr Met Arg
625                 630                 635                 640

Lys Ile Ile Leu Pro Gln Val Thr Lys Leu Met Leu Pro Asn Phe Val
                645                 650                 655

Asn Gln Phe Val Ile Ala Leu Lys Asp Thr Thr Ile Val Ser Ala Ile
            660                 665                 670

Gly Leu Val Glu Leu Phe Gln Thr Gly Lys Ile Ile Ala Arg Asn
    675                 680                 685

Tyr Gln Ser Phe Lys Met Tyr Ala Ile Leu Ala Ile Phe Tyr Leu Val
690                 695                 700

Ile Ile Thr Leu Leu Thr Arg Leu Ala Lys Arg Leu Glu Lys Arg Ile
705                 710                 715                 720

Arg

<210> SEQ ID NO 39
<211> LENGTH: 721
<212> TYPE: PRT
<213> ORGANISM: Streptococcus pneumoniae

<400> SEQUENCE: 39

Met Lys Lys Lys Phe Leu Ala Phe Leu Leu Ile Leu Phe Pro Ile Phe
1               5                   10                  15

Ser Leu Gly Ile Ala Lys Ala Glu Thr Ile Lys Ile Val Ser Asp Thr
                20                  25                  30

Ala Tyr Ala Pro Phe Glu Phe Lys Asp Ser Asp Gln Thr Tyr Lys Gly
            35                  40                  45

Ile Asp Val Asp Ile Ile Asn Lys Val Ala Glu Ile Lys Gly Trp Asn
    50                  55                  60

Ile Gln Met Ser Tyr Pro Gly Phe Asp Ala Ala Val Asn Ala Val Gln
65                  70                  75                  80

Ala Gly Gln Ala Asp Ala Ile Met Ala Gly Met Thr Lys Thr Lys Glu
                85                  90                  95

Arg Glu Lys Val Phe Thr Met Ser Asp Thr Tyr Tyr Asp Thr Lys Val
            100                 105                 110

Val Ile Ala Thr Thr Lys Ser His Lys Ile Ser Lys Tyr Asp Gln Leu
    115                 120                 125

Thr Gly Lys Thr Val Gly Val Lys Asn Gly Thr Ala Ala Gln Arg Phe
130                 135                 140

Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
                165                 170                 175

Met Met Asp Asp Lys Pro Val Ile Glu Tyr Ala Ile Asn Gln Gly Gln
            180                 185                 190

Asp Leu His Ile Glu Met Asp Gly Glu Ala Val Gly Ser Phe Ala Phe
    195                 200                 205

Gly Val Lys Lys Gly Ser Lys Tyr Glu His Leu Val Thr Glu Phe Asn
210                 215                 220

Gln Ala Leu Ser Glu Met Lys Lys Asp Gly Ser Leu Asp Lys Ile Ile
225                 230                 235                 240

Lys Lys Trp Thr Ala Ser Ser Ser Ser Ala Val Pro Thr Thr Thr Thr
```

-continued

```
                        245                 250                 255
Leu Ala Gly Leu Lys Ala Ile Pro Val Lys Ala Lys Tyr Ile Ile Ala
                260                 265                 270

Ser Asp Ser Ser Phe Ala Pro Phe Val Phe Gln Asn Ser Ser Asn Gln
            275                 280                 285

Tyr Thr Gly Ile Asp Met Glu Leu Ile Lys Ala Ile Ala Lys Asp Gln
        290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
                325                 330                 335

Thr Asp Ala Arg Lys Ala Thr Phe Asp Phe Ser Glu Ser Tyr Tyr Thr
            340                 345                 350

Ala Asn Thr Ile Leu Gly Val Lys Glu Ser Ser Asn Ile Ala Ser Tyr
        355                 360                 365

Glu Asp Leu Lys Gly Lys Thr Val Gly Val Lys Asn Gly Thr Ala Ser
370                 375                 380

Gln Thr Phe Leu Thr Glu Asn Gln Ser Lys Tyr Gly Tyr Lys Ile Lys
385                 390                 395                 400

Thr Phe Ala Asp Gly Ser Ser Met Tyr Asp Ser Leu Asn Thr Gly Ala
            405                 410                 415

Ile Asp Ala Val Met Asp Glu Pro Val Leu Lys Tyr Ser Ile Ser
        420                 425                 430

Gln Gly Gln Lys Leu Lys Thr Pro Ile Ser Gly Thr Pro Ile Gly Glu
            435                 440                 445

Thr Ala Phe Ala Val Lys Lys Gly Ala Asn Pro Glu Leu Ile Glu Met
        450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Ser Thr Ala Ser Thr Ser
            485                 490                 495

Thr Val Asp Glu Thr Thr Leu Trp Gly Leu Leu Gln Asn Asn Tyr Lys
        500                 505                 510

Gln Leu Leu Ser Gly Leu Gly Ile Thr Leu Ala Leu Ala Leu Ile Ser
            515                 520                 525

Phe Ala Ile Ala Ile Val Ile Gly Ile Ile Phe Gly Met Phe Ser Val
        530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
            565                 570                 575

Ile Pro Asn Phe Ile Glu Ser Ile Thr Gly Gln Gln Ser Pro Ile Asn
        580                 585                 590

Asp Phe Val Ala Gly Thr Ile Ala Leu Ser Leu Asn Ala Ala Ala Tyr
            595                 600                 605

Ile Ala Glu Ile Val Arg Gly Gly Ile Gln Ala Val Pro Val Gly Gln
        610                 615                 620

Met Glu Ala Ser Arg Ser Leu Gly Ile Ser Tyr Gly Lys Thr Met Arg
625                 630                 635                 640

Lys Ile Ile Leu Pro Gln Ala Thr Lys Leu Met Leu Pro Asn Phe Val
            645                 650                 655

Asn Gln Phe Val Ile Ala Leu Lys Asp Thr Thr Ile Val Ser Ala Ile
        660                 665                 670
```

-continued

```
Gly Leu Val Glu Leu Phe Gln Thr Gly Lys Ile Ile Ala Arg Asn
        675                 680                 685

Tyr Gln Ser Phe Lys Met Tyr Ala Ile Leu Ala Ile Phe Tyr Leu Val
690                 695                 700

Ile Ile Thr Leu Leu Thr Arg Leu Ala Lys Arg Leu Glu Lys Arg Ile
705                 710                 715                 720

Arg

<210> SEQ ID NO 40
<211> LENGTH: 721
<212> TYPE: PRT
<213> ORGANISM: Streptococcus pneumoniae

<400> SEQUENCE: 40

Met Lys Lys Phe Leu Ala Phe Leu Leu Ile Leu Phe Pro Ile Phe
1               5                   10                  15

Ser Leu Gly Ile Ala Lys Ala Glu Thr Ile Lys Ile Val Ser Asp Thr
                20                  25                  30

Ala Tyr Ala Pro Phe Glu Phe Lys Asp Ser Asp Gln Thr Tyr Lys Gly
            35                  40                  45

Ile Asp Val Asp Ile Ile Asn Lys Val Ala Glu Ile Lys Gly Trp Asn
50                  55                  60

Ile Gln Met Ser Tyr Pro Gly Phe Asp Ala Ala Val Asn Ala Val Gln
65                  70                  75                  80

Ala Gly Gln Ala Asp Ala Ile Met Ala Gly Met Thr Lys Thr Lys Glu
                85                  90                  95

Arg Glu Lys Val Phe Thr Met Ser Asp Thr Tyr Tyr Asp Thr Lys Val
            100                 105                 110

Val Ile Ala Thr Thr Lys Ser His Lys Ile Ser Lys Tyr Asp Gln Leu
            115                 120                 125

Thr Gly Lys Thr Val Gly Val Lys Asn Gly Thr Ala Ala Gln Arg Phe
    130                 135                 140

Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
                165                 170                 175

Met Met Asp Asp Lys Pro Val Ile Glu Tyr Ala Ile Asn Gln Gly Gln
            180                 185                 190

Asp Leu His Ile Glu Met Asp Gly Glu Ala Val Gly Ser Phe Ala Phe
        195                 200                 205

Gly Val Lys Lys Gly Ser Lys Tyr Glu His Leu Val Thr Glu Phe Asn
    210                 215                 220

Gln Ala Leu Ala Glu Met Lys Lys Asp Gly Ser Leu Asp Lys Ile Ile
225                 230                 235                 240

Lys Lys Trp Thr Ala Ser Ser Ser Ala Val Pro Thr Thr Thr
                245                 250                 255

Leu Ala Gly Leu Lys Ala Ile Pro Val Lys Ala Lys Tyr Ile Ile Ala
            260                 265                 270

Ser Asp Ser Ser Phe Ala Pro Phe Val Phe Gln Asn Ser Asn Gln
        275                 280                 285

Tyr Thr Gly Ile Asp Met Glu Leu Ile Lys Ala Ile Ala Lys Asp Gln
    290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
```

```
                325                 330                 335
Thr Asp Ala Arg Lys Ala Thr Phe Asp Phe Ser Glu Ser Tyr Tyr Thr
            340                 345                 350
Ala Asn Thr Ile Leu Gly Val Lys Glu Ser Ser Asn Ile Ala Ser Tyr
        355                 360                 365
Glu Asp Leu Lys Gly Lys Thr Val Gly Val Lys Asn Gly Thr Ala Ser
    370                 375                 380
Gln Thr Phe Leu Thr Glu Asn Gln Ser Lys Tyr Gly Tyr Lys Ile Lys
385                 390                 395                 400
Thr Phe Ala Asp Gly Ser Ser Met Tyr Asp Ser Leu Asn Thr Gly Ala
            405                 410                 415
Ile Asp Ala Val Met Asp Asp Glu Pro Val Leu Lys Tyr Ser Ile Ser
        420                 425                 430
Gln Gly Gln Lys Leu Lys Thr Pro Ile Ser Gly Thr Pro Ile Gly Glu
    435                 440                 445
Thr Ala Phe Ala Val Lys Lys Gly Ala Asn Pro Glu Leu Ile Glu Met
450                 455                 460
Phe Asn Asn Gly Leu Ala Asn Leu Lys Ala Asn Gly Glu Phe Gln Lys
465                 470                 475                 480
Ile Leu Asp Lys Tyr Leu Ala Ser Glu Ser Ser Thr Ala Ser Thr Ser
            485                 490                 495
Thr Val Asp Glu Thr Thr Leu Trp Gly Leu Leu Gln Asn Asn Tyr Lys
        500                 505                 510
Gln Leu Leu Ser Gly Leu Gly Ile Thr Leu Ala Leu Ala Leu Ile Ser
    515                 520                 525
Phe Ala Ile Ala Ile Val Ile Gly Ile Ile Phe Gly Met Phe Ser Val
530                 535                 540
Ser Pro Tyr Lys Ser Leu Arg Val Ile Ser Glu Ile Phe Val Asp Val
545                 550                 555                 560
Ile Arg Gly Ile Pro Leu Met Ile Leu Ala Ala Phe Ile Phe Trp Gly
            565                 570                 575
Ile Pro Asn Phe Ile Glu Ser Ile Thr Gly Gln Gln Ser Pro Ile Asn
        580                 585                 590
Asp Phe Val Ala Gly Thr Ile Ala Leu Ser Leu Asn Ala Ala Ala Tyr
    595                 600                 605
Ile Ala Glu Ile Val Arg Gly Gly Ile Gln Ala Val Pro Val Gly Gln
    610                 615                 620
Met Glu Ala Ser Arg Ser Leu Gly Ile Ser Tyr Gly Lys Thr Met Arg
625                 630                 635                 640
Lys Ile Ile Leu Pro Gln Ala Thr Lys Leu Met Leu Pro Asn Phe Val
            645                 650                 655
Asn Gln Phe Val Ile Ala Leu Lys Asp Thr Thr Ile Val Ser Ala Ile
        660                 665                 670
Gly Leu Val Glu Leu Phe Gln Thr Gly Lys Ile Ile Ala Arg Asn
    675                 680                 685
Tyr Gln Ser Phe Lys Met Tyr Ala Ile Leu Ala Ile Phe Tyr Leu Val
    690                 695                 700
Ile Ile Thr Leu Leu Thr Arg Leu Ala Lys Arg Leu Glu Lys Arg Ile
705                 710                 715                 720
Arg

<210> SEQ ID NO 41
<211> LENGTH: 721
<212> TYPE: PRT
```

<213> ORGANISM: Streptococcus pneumoniae

<400> SEQUENCE: 41

```
Met Lys Lys Lys Phe Leu Ala Phe Leu Leu Ile Leu Phe Pro Ile Phe
 1               5                  10                  15
Ser Leu Gly Ile Ala Lys Ala Glu Thr Ile Lys Ile Val Ser Asp Thr
                20                  25                  30
Ala Tyr Ala Pro Phe Glu Phe Lys Asp Ser Asp Gln Thr Tyr Lys Gly
            35                  40                  45
Ile Asp Val Asp Ile Ile Asn Lys Val Ala Glu Ile Lys Gly Trp Asn
        50                  55                  60
Ile Gln Met Ser Tyr Pro Gly Phe Asp Ala Ala Val Asn Ala Val Gln
65                  70                  75                  80
Ala Gly Gln Ala Asp Ala Ile Met Ala Gly Met Thr Lys Thr Lys Glu
                85                  90                  95
Arg Glu Lys Val Phe Thr Met Ser Asp Thr Tyr Tyr Asp Thr Lys Val
            100                 105                 110
Val Ile Ala Thr Thr Lys Ser His Lys Ile Ser Lys Tyr Asp Gln Leu
        115                 120                 125
Thr Gly Lys Thr Val Gly Val Lys Asn Gly Thr Ala Ala Gln Arg Phe
130                 135                 140
Leu Glu Thr Ile Lys Asp Lys Tyr Gly Phe Thr Ile Lys Thr Phe Asp
145                 150                 155                 160
Thr Gly Asp Leu Met Asn Asn Ser Leu Ser Ala Gly Ala Ile Asp Ala
                165                 170                 175
Met Met Asp Asp Lys Pro Val Ile Glu Tyr Ala Ile Asn Gln Gly Gln
            180                 185                 190
Asp Leu His Ile Glu Met Asp Gly Glu Ala Val Gly Ser Phe Ala Phe
        195                 200                 205
Gly Val Lys Lys Gly Ser Lys Tyr Glu His Leu Val Thr Glu Phe Asn
    210                 215                 220
Gln Ala Leu Ala Glu Met Lys Lys Asp Gly Ser Leu Asp Lys Ile Ile
225                 230                 235                 240
Lys Lys Trp Thr Ala Ser Ser Ser Ala Val Pro Thr Thr Thr Thr
                245                 250                 255
Leu Ala Gly Leu Lys Ala Ile Pro Val Lys Ala Lys Tyr Ile Ile Ala
            260                 265                 270
Ser Asp Ser Ser Phe Ala Pro Phe Val Phe Gln Asn Ser Ser Asn Gln
        275                 280                 285
Tyr Thr Gly Ile Asp Met Glu Leu Ile Lys Ala Ile Ala Lys Asp Gln
    290                 295                 300
Gly Phe Glu Ile Glu Ile Thr Asn Pro Gly Phe Asp Ala Ala Ile Ser
305                 310                 315                 320
Ala Val Gln Ala Gly Gln Ala Asp Gly Ile Ile Ala Gly Met Ser Val
                325                 330                 335
Thr Asp Ala Arg Lys Ala Thr Phe Asp Phe Ser Glu Ser Tyr Tyr Thr
            340                 345                 350
Ala Asn Thr Ile Leu Gly Val Lys Glu Ser Ser Asn Ile Ala Ser Tyr
        355                 360                 365
Glu Asp Leu Lys Gly Lys Thr Val Gly Val Lys Asn Gly Thr Ala Ser
    370                 375                 380
Gln Thr Phe Leu Thr Glu Asn Gln Ser Lys Tyr Gly Tyr Lys Ile Lys
385                 390                 395                 400
Thr Phe Ala Asp Gly Ser Ser Met Tyr Asp Ser Leu Asn Thr Gly Ala
```

```
                405                 410                 415
Ile Asp Ala Val Met Asp Glu Pro Val Leu Lys Tyr Ser Ile Ser
            420                 425                 430

Gln Gly Gln Lys Leu Lys Thr Pro Ile Ser Gly Thr Pro Ile Gly Glu
            435                 440                 445

Thr Ala Phe Ala Val Lys Lys Gly Ala Asn Pro Glu Leu Ile Glu Met
450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Thr Ala Ser Thr Ser
            485                 490                 495

Thr Val Asp Glu Thr Thr Leu Trp Gly Leu Leu Gln Asn Asn Tyr Lys
            500                 505                 510

Gln Leu Leu Ser Gly Leu Gly Ile Thr Leu Ala Leu Ala Leu Ile Ser
            515                 520                 525

Phe Ala Ile Ala Ile Val Ile Gly Ile Ile Phe Gly Met Phe Ser Val
            530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
            565                 570                 575

Ile Pro Asn Phe Ile Glu Ser Ile Thr Gly Gln Gln Ser Pro Ile Asn
            580                 585                 590

Asp Phe Val Ala Gly Thr Ile Ala Leu Ser Leu Asn Ala Ala Ala Tyr
            595                 600                 605

Ile Ala Glu Ile Val Arg Gly Gly Ile Gln Ala Val Pro Val Gly Gln
            610                 615                 620

Met Glu Ala Ser Arg Ser Leu Gly Ile Ser Tyr Gly Lys Thr Met Arg
625                 630                 635                 640

Lys Ile Ile Leu Pro Gln Ala Thr Lys Leu Met Leu Pro Asn Phe Val
            645                 650                 655

Asn Gln Phe Val Ile Ala Leu Lys Asp Thr Thr Ile Val Ser Ala Ile
            660                 665                 670

Gly Leu Val Glu Leu Phe Gln Thr Gly Lys Ile Ile Ala Arg Asn
            675                 680                 685

Tyr Gln Ser Phe Lys Met Tyr Ala Ile Leu Ala Ile Phe Tyr Leu Val
            690                 695                 700

Ile Ile Thr Leu Leu Thr Arg Leu Ala Lys Arg Leu Glu Lys Arg Ile
705                 710                 715                 720

Arg

<210> SEQ ID NO 42
<211> LENGTH: 721
<212> TYPE: PRT
<213> ORGANISM: Streptococcus pneumoniae

<400> SEQUENCE: 42

Met Lys Lys Lys Phe Leu Ala Phe Leu Leu Ile Leu Phe Pro Ile Phe
1                 5                   10                  15

Ser Leu Gly Ile Ala Lys Ala Glu Thr Ile Lys Ile Val Ser Asp Thr
            20                  25                  30

Ala Tyr Ala Pro Phe Glu Phe Lys Asp Ser Asp Gln Thr Tyr Lys Gly
        35                  40                  45

Ile Asp Val Asp Ile Ile Asn Lys Val Ala Glu Ile Lys Gly Trp Asn
    50                  55                  60
```

```
Ile Gln Met Ser Tyr Pro Gly Phe Asp Ala Val Asn Ala Val Gln
 65                  70                  75                  80

Ala Gly Gln Ala Asp Ala Ile Met Ala Gly Met Thr Lys Thr Lys Glu
                 85                  90                  95

Arg Glu Lys Val Phe Thr Met Ser Asp Thr Tyr Asp Thr Lys Val
                100                 105                 110

Val Ile Ala Thr Thr Lys Ser His Lys Ile Ser Lys Tyr Asp Gln Leu
             115                 120                 125

Thr Gly Lys Thr Val Gly Val Lys Asn Gly Thr Ala Ala Gln Arg Phe
             130                 135                 140

Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
                 165                 170                 175

Met Met Asp Asp Lys Pro Val Ile Glu Tyr Ala Ile Asn Gln Gly Gln
                 180                 185                 190

Asp Leu His Ile Glu Met Asp Gly Glu Ala Val Gly Ser Phe Ala Phe
             195                 200                 205

Gly Val Lys Lys Gly Ser Lys Tyr Glu His Leu Val Thr Glu Phe Asn
             210                 215                 220

Gln Ala Leu Ala Glu Met Lys Lys Asp Gly Ser Leu Asp Lys Ile Ile
225                 230                 235                 240

Lys Lys Trp Thr Ala Ser Ser Ser Ala Val Pro Thr Thr Thr Thr
                 245                 250                 255

Leu Ala Gly Leu Lys Ala Ile Pro Val Lys Ala Lys Tyr Ile Ile Ala
                 260                 265                 270

Ser Asp Ser Ser Phe Ala Pro Phe Val Phe Gln Asn Ser Ser Asn Gln
             275                 280                 285

Tyr Thr Gly Ile Asp Met Glu Leu Ile Lys Ala Ile Ala Lys Asp Gln
             290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
                 325                 330                 335

Thr Asp Ala Arg Lys Ala Thr Phe Asp Phe Ser Glu Ser Tyr Tyr Thr
                 340                 345                 350

Ala Asn Thr Ile Leu Gly Val Lys Glu Ser Ser Asn Ile Ala Ser Tyr
             355                 360                 365

Glu Asp Leu Lys Gly Lys Thr Val Gly Val Lys Asn Gly Thr Ala Ser
             370                 375                 380

Gln Thr Phe Leu Thr Glu Asn Gln Ser Lys Tyr Gly Tyr Lys Ile Lys
385                 390                 395                 400

Thr Phe Ala Asp Gly Ser Ser Met Tyr Asp Ser Leu Asn Thr Gly Ala
                 405                 410                 415

Ile Asp Ala Val Met Asp Asp Glu Pro Val Leu Lys Tyr Ser Ile Ser
                 420                 425                 430

Gln Gly Gln Lys Leu Lys Thr Pro Ile Ser Gly Thr Pro Ile Gly Glu
             435                 440                 445

Thr Ala Phe Ala Val Lys Lys Gly Ala Asn Pro Glu Leu Ile Glu Met
             450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Ser Thr Ala Ser Thr Ser
```

```
                        485                 490                 495
Thr Val Asp Glu Thr Thr Leu Trp Gly Leu Leu Gln Asn Asn Tyr Lys
                500                 505                 510

Gln Leu Leu Ser Gly Leu Gly Ile Thr Leu Ala Leu Ala Leu Ile Ser
            515                 520                 525

Phe Ala Ile Ala Ile Val Ile Gly Ile Ile Phe Gly Met Phe Ser Val
        530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
                565                 570                 575

Ile Pro Asn Phe Ile Glu Ser Ile Thr Gly Gln Gln Ser Pro Ile Asn
                580                 585                 590

Asp Phe Val Ala Gly Thr Ile Ala Leu Ser Leu Asn Ala Ala Ala Tyr
                595                 600                 605

Ile Ala Glu Ile Val Arg Gly Gly Ile Gln Ala Val Pro Val Gly Gln
            610                 615                 620

Met Glu Ala Ser Arg Ser Leu Gly Ile Ser Tyr Gly Lys Thr Met Arg
625                 630                 635                 640

Lys Ile Ile Leu Pro Gln Ala Thr Lys Leu Met Leu Pro Asn Phe Val
                645                 650                 655

Asn Gln Phe Val Ile Ala Leu Lys Asp Thr Thr Ile Val Ser Ala Ile
                660                 665                 670

Gly Leu Val Glu Leu Phe Gln Thr Gly Lys Ile Ile Ile Ala Arg Asn
            675                 680                 685

Tyr Gln Ser Phe Lys Met Tyr Ala Ile Leu Ala Ile Phe Tyr Leu Val
        690                 695                 700

Ile Ile Thr Leu Leu Thr Arg Leu Ala Lys Arg Leu Glu Lys Arg Ile
705                 710                 715                 720

Arg

<210> SEQ ID NO 43
<211> LENGTH: 721
<212> TYPE: PRT
<213> ORGANISM: Streptococcus pneumoniae

<400> SEQUENCE: 43

Met Lys Lys Lys Phe Leu Ala Phe Leu Leu Ile Leu Phe Pro Ile Phe
1               5                   10                  15

Ser Leu Gly Ile Ala Lys Ala Glu Thr Ile Lys Ile Val Ser Asp Thr
            20                  25                  30

Ala Tyr Ala Pro Phe Glu Phe Lys Asp Ser Asp Gln Thr Tyr Lys Gly
        35                  40                  45

Ile Asp Val Asp Ile Ile Asn Lys Val Ala Glu Ile Lys Gly Trp Asn
    50                  55                  60

Ile Gln Met Ser Tyr Pro Gly Phe Asp Ala Ala Val Asn Ala Val Gln
65                  70                  75                  80

Ala Gly Gln Ala Asp Ala Ile Met Ala Gly Met Thr Lys Thr Lys Glu
                85                  90                  95

Arg Glu Lys Val Phe Thr Met Ser Asp Thr Tyr Tyr Asp Thr Lys Val
            100                 105                 110

Val Ile Ala Thr Thr Lys Ser His Lys Ile Ser Lys Tyr Asp Gln Leu
        115                 120                 125

Thr Gly Lys Thr Val Gly Val Lys Asn Gly Thr Ala Ala Gln Arg Phe
    130                 135                 140
```

```
Leu Glu Thr Ile Lys Asp Lys Tyr Gly Phe Thr Ile Lys Thr Phe Asp
145                 150                 155                 160

Thr Gly Asp Leu Met Asn Asn Ser Leu Ser Ala Gly Ala Ile Asp Ala
            165                 170                 175

Met Met Asp Asp Lys Pro Val Ile Glu Tyr Ala Ile Asn Gln Gly Gln
        180                 185                 190

Asp Leu His Ile Glu Met Asp Gly Glu Ala Val Gly Ser Phe Ala Phe
            195                 200                 205

Gly Val Lys Lys Gly Ser Lys Tyr Glu His Leu Val Thr Glu Phe Asn
        210                 215                 220

Gln Ala Leu Ala Glu Met Lys Lys Asp Gly Ser Leu Asp Lys Ile Ile
225                 230                 235                 240

Lys Lys Trp Thr Ala Ser Ser Ser Ala Val Pro Thr Thr Thr Thr Thr
                245                 250                 255

Leu Ala Gly Leu Lys Ala Ile Pro Val Lys Ala Lys Tyr Ile Ile Ala
            260                 265                 270

Ser Asp Ser Ser Phe Ala Pro Phe Val Phe Gln Asn Ser Ser Asn Gln
        275                 280                 285

Tyr Thr Gly Ile Asp Met Glu Leu Ile Lys Ala Ile Ala Lys Asp Gln
        290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
                325                 330                 335

Thr Asp Ala Arg Lys Ala Thr Phe Asp Phe Ser Glu Ser Tyr Tyr Thr
                340                 345                 350

Ala Asn Thr Ile Leu Gly Val Lys Glu Ser Ser Asn Ile Ala Ser Tyr
            355                 360                 365

Glu Asp Leu Lys Gly Lys Thr Val Gly Val Lys Asn Gly Thr Ala Ser
        370                 375                 380

Gln Thr Phe Leu Thr Glu Asn Gln Ser Lys Tyr Gly Tyr Lys Ile Lys
385                 390                 395                 400

Thr Phe Ala Asp Gly Ser Ser Met Tyr Asp Ser Leu Asn Thr Gly Ala
                405                 410                 415

Ile Asp Ala Val Met Asp Asp Glu Pro Val Leu Lys Tyr Ser Ile Ser
                420                 425                 430

Gln Gly Gln Lys Leu Lys Thr Pro Ile Ser Gly Thr Pro Ile Gly Glu
            435                 440                 445

Thr Ala Phe Ala Val Lys Lys Gly Ala Asn Pro Glu Leu Ile Glu Met
        450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Ser Thr Ala Ser Thr Ser
                485                 490                 495

Thr Val Asp Glu Thr Thr Leu Trp Gly Leu Leu Gln Asn Asn Tyr Lys
            500                 505                 510

Gln Leu Leu Ser Gly Leu Gly Ile Thr Leu Ala Leu Ala Leu Ile Ser
        515                 520                 525

Phe Ala Ile Ala Ile Val Ile Gly Ile Ile Phe Gly Met Phe Ser Val
        530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
```

-continued

```
                565                 570                 575
Ile Pro Asn Phe Ile Glu Ser Ile Thr Gly Gln Gln Ser Pro Ile Asn
            580                 585                 590

Asp Phe Val Ala Gly Thr Ile Ala Leu Ser Leu Asn Ala Ala Ala Tyr
            595                 600                 605

Ile Ala Glu Ile Val Arg Gly Ile Gln Ala Val Pro Val Gly Gln
            610                 615                 620

Met Glu Ala Ser Arg Ser Leu Gly Ile Ser Tyr Gly Lys Thr Met Arg
625                 630                 635                 640

Lys Ile Ile Leu Pro Gln Ser Thr Lys Leu Met Leu Pro Asn Phe Val
                645                 650                 655

Asn Gln Phe Val Ile Ala Leu Lys Asp Thr Thr Ile Val Ser Ala Ile
            660                 665                 670

Gly Leu Val Glu Leu Phe Gln Thr Gly Lys Ile Ile Ala Arg Asn
            675                 680                 685

Tyr Gln Ser Phe Lys Met Tyr Ala Ile Leu Ala Ile Phe Tyr Leu Val
            690                 695                 700

Ile Ile Thr Leu Leu Thr Arg Leu Ala Lys Arg Leu Glu Lys Arg Ile
705                 710                 715                 720

Arg

<210> SEQ ID NO 44
<211> LENGTH: 721
<212> TYPE: PRT
<213> ORGANISM: Streptococcus pneumoniae

<400> SEQUENCE: 44

Met Lys Lys Lys Phe Leu Ala Phe Leu Leu Ile Leu Phe Pro Ile Phe
1               5                   10                  15

Ser Leu Gly Ile Ala Lys Ala Glu Thr Ile Lys Ile Val Ser Asp Thr
            20                  25                  30

Ala Tyr Ala Pro Phe Glu Phe Lys Asp Ser Asp Gln Thr Tyr Lys Gly
            35                  40                  45

Ile Asp Val Asp Ile Ile Asn Lys Val Ala Glu Ile Lys Gly Trp Asn
        50                  55                  60

Ile Gln Met Ser Tyr Pro Gly Phe Asp Ala Ala Val Asn Ala Val Gln
65              70                  75                  80

Ala Gly Gln Ala Asp Ala Ile Met Ala Gly Met Thr Lys Thr Lys Glu
                85                  90                  95

Arg Glu Lys Val Phe Thr Met Ser Asp Thr Tyr Tyr Asp Thr Lys Val
            100                 105                 110

Val Ile Ala Thr Thr Lys Ser His Lys Ile Ser Lys Tyr Asp Gln Leu
            115                 120                 125

Thr Gly Lys Thr Val Gly Val Lys Asn Gly Thr Ala Ala Gln Arg Phe
        130                 135                 140

Leu Glu Thr Ile Lys Asp Lys Tyr Gly Phe Thr Ile Lys Thr Phe Asp
145             150                 155                 160

Thr Gly Asp Leu Met Asn Asn Ser Leu Ser Ala Gly Ala Ile Asp Ala
                165                 170                 175

Met Met Asp Asp Lys Pro Val Ile Glu Tyr Ala Ile Asn Gln Gly Gln
            180                 185                 190

Asp Leu His Ile Glu Met Asp Gly Glu Ala Val Gly Ser Phe Ala Phe
            195                 200                 205

Gly Val Lys Lys Gly Ser Lys Tyr Glu His Leu Val Thr Glu Phe Asn
        210                 215                 220
```

-continued

```
Gln Ala Leu Ala Glu Met Lys Lys Asp Gly Ser Leu Asp Lys Ile Ile
225                 230                 235                 240

Lys Lys Trp Thr Ala Ser Ser Ser Ala Val Pro Thr Thr Thr Thr Thr
            245                 250                 255

Leu Ala Gly Leu Lys Ala Ile Pro Val Lys Ala Lys Tyr Ile Ile Ala
        260                 265                 270

Ser Asp Ser Ser Phe Ala Pro Phe Val Phe Gln Asn Ser Ser Asn Gln
    275                 280                 285

Tyr Thr Gly Ile Asp Met Glu Leu Ile Lys Ala Ile Ala Lys Asp Gln
290                 295                 300

Gly Phe Glu Ile Glu Ile Thr Asn Pro Gly Phe Asp Ala Ala Ile Ser
305                 310                 315                 320

Ala Val Gln Ala Gly Gln Ala Asp Gly Ile Ile Ala Gly Met Ser Val
                325                 330                 335

Thr Asp Ala Arg Lys Ala Thr Phe Asp Phe Ser Glu Ser Tyr Tyr Thr
            340                 345                 350

Ala Asn Thr Ile Leu Gly Val Lys Glu Ser Ser Asn Ile Ala Ser Tyr
        355                 360                 365

Glu Asp Leu Lys Gly Lys Thr Val Gly Val Lys Asn Gly Thr Ala Ser
    370                 375                 380

Gln Thr Phe Leu Thr Glu Asn Gln Ser Lys Tyr Gly Tyr Lys Ile Lys
385                 390                 395                 400

Thr Phe Ala Asp Gly Ser Ser Met Tyr Asp Ser Leu Asn Thr Gly Ala
                405                 410                 415

Ile Asp Ala Val Met Asp Asp Glu Pro Val Leu Lys Tyr Ser Ile Ser
            420                 425                 430

Gln Gly Gln Lys Leu Lys Thr Pro Ile Ser Gly Thr Pro Ile Gly Glu
        435                 440                 445

Thr Ala Phe Ala Val Lys Lys Gly Ala Asn Pro Glu Leu Ile Glu Met
    450                 455                 460

Phe Asn Asn Gly Leu Ala Asn Leu Lys Ala Asn Gly Glu Phe Gln Lys
465                 470                 475                 480

Ile Leu Asp Lys Tyr Leu Ala Ser Glu Ser Ser Thr Ala Ser Thr Ser
                485                 490                 495

Thr Val Asp Glu Thr Thr Leu Trp Gly Leu Leu Gln Asn Asn Tyr Lys
            500                 505                 510

Gln Leu Leu Ser Gly Leu Gly Ile Thr Leu Ala Leu Ala Leu Ile Ser
        515                 520                 525

Phe Ala Ile Ala Ile Val Ile Gly Ile Ile Phe Gly Met Phe Ser Val
    530                 535                 540

Ser Pro Tyr Lys Ser Leu Arg Val Ile Ser Glu Ile Phe Val Asp Val
545                 550                 555                 560

Ile Arg Gly Ile Pro Leu Met Ile Leu Ala Ala Phe Ile Phe Trp Gly
                565                 570                 575

Ile Pro Asn Phe Ile Glu Ser Ile Thr Gly Gln Gln Ser Pro Ile Asn
            580                 585                 590

Asp Phe Val Ala Gly Thr Ile Ala Leu Ser Leu Asn Ala Ala Ala Tyr
        595                 600                 605

Ile Ala Glu Ile Val Arg Gly Gly Ile Gln Ala Val Pro Val Gly Gln
    610                 615                 620

Met Glu Ala Ser Arg Ser Leu Gly Ile Ser Tyr Gly Lys Thr Met Arg
625                 630                 635                 640

Lys Ile Ile Leu Pro Gln Ala Thr Lys Leu Met Leu Pro Asn Phe Val
```

-continued

```
                        645                 650                 655
Asn Gln Phe Val Ile Ala Leu Lys Asp Thr Thr Ile Val Ser Ala Ile
                660                 665                 670

Gly Leu Val Glu Leu Phe Gln Thr Gly Lys Ile Ile Ile Ala Arg Asn
            675                 680                 685

Tyr Gln Ser Phe Lys Met Tyr Ala Ile Leu Ala Ile Phe Tyr Leu Val
        690                 695                 700

Ile Ile Thr Leu Leu Thr Arg Leu Ala Lys Arg Leu Glu Lys Arg Ile
705                 710                 715                 720

Ser
```